US008673551B2

(12) United States Patent
Rimsky et al.

(10) Patent No.: US 8,673,551 B2
(45) Date of Patent: Mar. 18, 2014

(54) METHODS, PLASMID VECTORS AND PRIMERS FOR ASSESSING HIV VIRAL FITNESS

(75) Inventors: Laurence Tatiana Rimsky, Kapellen (BE); Inky Paul Madeleine De Baere, Temse (BE); Bart Anna Julien Maes, Rumst (BE); Marie-Pierre T. M. M. G. De Bethune, Everberg (BE); Guenter Kraus, Sint-Katelijne-Waver (BE); Elisa Mokany, Kirrawee (AU); Alison Velyian Todd, Glebe (AU)

(73) Assignees: Speedx Pty Ltd., Eveleigh (AU); Janssen R&D Ireland, Little Island, Co. Cork (IE)

( * ) Notice: Subject to any disclaimer, the term of this patent is extended or adjusted under 35 U.S.C. 154(b) by 770 days.

(21) Appl. No.: 12/094,708

(22) PCT Filed: Dec. 7, 2006

(86) PCT No.: PCT/EP2006/069422

§ 371 (c)(1),
(2), (4) Date: May 22, 2008

(87) PCT Pub. No.: WO2007/065926

PCT Pub. Date: Jun. 14, 2007

(65) Prior Publication Data

US 2010/0035229 A1 Feb. 11, 2010

(30) Foreign Application Priority Data

Dec. 7, 2005 (EP) ...................................... 05111802

(51) Int. Cl.
*C12Q 1/68* (2006.01)
*C12Q 1/70* (2006.01)
*C12N 1/11* (2006.01)
*A61K 39/21* (2006.01)

(52) U.S. Cl.
USPC ......... 435/5; 435/6.11; 435/235.1; 424/188.1

(58) Field of Classification Search
USPC ............................................................ 435/6
See application file for complete search history.

(56) References Cited

U.S. PATENT DOCUMENTS

| 4,000,159 | A | 12/1976 | Scoggins et al. | |
|---|---|---|---|---|
| 4,683,195 | A | 7/1987 | Mullis et al. | |
| 4,683,202 | A | 7/1987 | Mullis | |
| 4,965,188 | A | 10/1990 | Mullis et al. | |
| 5,176,995 | A | 1/1993 | Sninsky et al. | |
| 6,140,055 | A | 10/2000 | Todd et al. | |
| 2004/0202999 | A1* | 10/2004 | Dropulic et al. | 435/5 |
| 2005/0244818 | A1 | 11/2005 | Siliciano et al. | |
| 2006/0292553 | A1 | 12/2006 | Lebel-Binay et al. | |
| 2008/0113335 | A1 | 5/2008 | Alcami Pertejo et al. | |

FOREIGN PATENT DOCUMENTS

| EP | 1 283 272 | 2/2003 |
|---|---|---|
| EP | 1 285 971 | 2/2003 |
| FR | 2 869 045 | 10/2006 |
| WO | WO 97/27480 | 7/1997 |
| WO | WO 99/66071 | 12/1999 |
| WO | WO 00/29611 | 5/2000 |
| WO | WO 00/68436 | * 11/2000 |
| WO | WO 02/20571 | 3/2002 |
| WO | WO 03/011334 | 2/2003 |
| WO | WO 03/020878 | * 3/2003 |
| WO | WO 2005/108588 | 11/2005 |
| WO | WO 2007/041774 | 4/2007 |

OTHER PUBLICATIONS

Markringiorgos GM. et al. "A PCR-based amplification method retaining the quantitative differenc between two complex genomes" (Nature Biotechnology; 10:936-989; 2002.*
Buck "Design strategies and performance of custom DNA sequencing primers" Biotechniques 27(30:528-536, 1999.*
Kalaydjieva et al., Silent mutations in the phenylalanine hydroxylase gene as an aid to the diagnosis of phenylketonuria, 1991, Journal of Medical Genetics, 28:686-690.*
Aldea et al., "Rapid Detection of Herpes Simplex Virus DNA in Genital Ulcers by Real-Time PCR Using SYBR Green I Dye as the Detection Signal," *Journal of Clinical Microbiology*, 2002; 40(3):1060-1062.
Boom et al., "Rapid and Simple Method for Purification of Nucleic Acids," *Journal of Clinical Microbiology*, 1990; 28(3):495-503.
Chomczynski et al., "Single-Step Method of RNA Isolation by Acid Guanidinium Thiocyanate-Phenol-Chloroform Extraction," *Analytical Biochemistry*, 1987; 162:156-159.
Croteau et al., "Impaired Fitness of Human Immunodeficiency Virus Type 1 Variants with High-Level Resistance to Protease Inhibitors," *Journal of Virology*, 1997; 71(2):1089-1096.
Deeks et al., "Virologic and Immunologic Consequences of Discontinuing Combination Antiretroviral-Drug Therapy in HIV-Infected Patients with Detectable Viremia," *New England Journal of Medicine*, 2001; 344(7):472-480.
Dehee et al., "Quantitation of HTLV-1 Proviral Load by a TaqMan Real-Time PCR Assay," *Journal of Virology Methods*, 2002; 102:37-51.
Devereux et al., "Rapid Decline in Detectability of HIV-1 Drug Resistance Mutations after Stopping Therapy," *AIDS*, 1999; 13:F123-F127.
Eastman et al., "Nonisotopic Hybridization Assay for Determination of Relative Amounts of Genotypic Human Immunodeficiency Virus Type 1 Zidovudine Resistance," *Journal of Clinical Microbiology*, 1995; 33(10):2777-2780.

(Continued)

Primary Examiner — Stacy B. Chen
Assistant Examiner — Barry A. Chestnut
(74) Attorney, Agent, or Firm — Baker & Hostetler LLP

(57) ABSTRACT

The present invention relates to methods and means for the evaluation of HIV replicative capacity in a given environment. In particular, the invention provides a growth competition assay that can determine relative viral fitness using a recombinant tagged HIV-1 virus system. The methods rely on plasmid vectors, amplicons, primers and probes, and the generation of replication-competent viruses therefrom. Said methods and materials may find use in multiple fields including diagnostics, drug screening, pharmacogenetics and drug development.

10 Claims, 22 Drawing Sheets

(56) References Cited

OTHER PUBLICATIONS

Emilsson et al., "Deoxyribozymes: New Activities and New Applications," *Cellular and Molecular Life Sciences*, 2002; 59:596-607.

Harrigan et al., "Relative Replicative Fitness of Zidovudine-Resistant Human Immunodeficiency Virus Type 1 Isolates In Vitro," *Journal of Virology*, 1998; 72(5):3773-3778.

Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents and Chemotherapy*, 1998; 42(2):269-276.

Kellam et al., "Recombinant Virus Assay: A Rapid, Phenotypic Assay for Assessment of Drug Susceptibility of Human Immunodeficiency Virus Type 1 Isolates," *Antimicrobial Agents and Chemotherapy*, 1994; 38(1):23-30.

Kosalaraksa et al., "Comparative Fitness of Multi-Dideoxynucleoside-Resistant Human Immunodeficiency Virus Type 1 (HIV-1) in an In Vitro Competitive HIV-1 Replication Assay," *Journal of Virology*, 1999; 73(7):5356-5363.

Larder et al., "Potential Mechanism for Sustained Antiretroviral Efficacy of AZT-3TC Combination Therapy," *Science*, 1995; 269:696-699.

Lu et al., "A Novel Recombinant Marker Virus Assay for Comparing the Relative Fitness of HIV-1 Reverse Transcriptase Variants," *Journal of Acquired Immune Deficiency Syndromes*, 2001; 27:7-13.

Martinez-Picado et al., "Replicative Fitness of Protease Inhibitor-Resistant Mutants of Human Immunodeficiency Virus Type 1," *Journal of Virology*, 1999; 73(5):3744-3752.

Maschera et al., "Analysis of Resistance to Human Immunodeficiency Virus Type 1 Protease Inhibitors by Using Matched Bacterial Expression and Proviral Infection Vectors," *Journal of Virology*, 1995; 69(9):5431-5436.

Miller et al., "Virological and Immunological Effects of Treatment Interruptions in HIV-1 Infected Patients with Treatment Failure," *AIDS*, 2000; 14:2857-2867.

Nijhuis et al., "Increased Fitness of Drug Resistant HIV-1 Protease as a Result of Acquisition of Compensatory Mutations During Suboptimal Therapy," *AIDS*, 1999; 13:2349-2359.

Ratner et al., "Complete Nucleotide Sequences of Functional Clones of the AIDS Virus," *AIDS Research and Human Retroviruses*, 1987; 3(1):57-69.

Robinson et al., "HIV Type 1 Protease Cleavage Site Mutations and Viral Fitness: Implications for Drug Susceptibility Phenotyping Assays," *AIDS Research and Human Retroviruses*, 2000; 16(12):1149-1156.

Robinson et al., "Inclusion of Full Length Human Immunodeficiency Virus Type 1 (HIV-1) *Gag* Sequences in Viral Recombinants Applied to Drug Susceptibility Phenotyping," *Journal of Virological Methods*, 2002; 104:147-160.

Santoro et al., "A General Purpose RNA Cleaving DNA Enzyme," *Proc. Natl. Acad. Sci.*, 1997; 94:4262-4266.

Schweitzer et al., "Combining Nucleic Acid Amplification and Detection," *Current Opinion in Biotechnology*, 2001; 12:21-27.

Tyagi et al., "Multicolor Molecular Beacons for Allele Discrimination," *Nature Biotechnology*, 1998; 16:49-53.

Van Maarseveen et al., "A Novel Real-Time PCR Assay to Determine Relative Replication Capacity for HIV-1 Protease Variants and/or Reverse Transcriptase Variants," *Journal of Virological Methods*, 2006; 133:185-194.

Verhofstede et al., "Interruption of Reverse Transcriptase Inhibitors or a Switch from Reverse Transcriptase to Protease Inhibitors Resulted in a Fast Reappearance of Virus Strains with a Reverse Transcriptase Inhibitor-Sensitive Genotype," *AIDS*, 1999; 13:2541-2546.

Weber et al., "A Novel TaqMan Real-Time PCR Assay to Estimate Ex Vivo Human Immunodeficiency Virus Type 1 Fitness in the Era of Multi-Target (*pol* and *env*) Antiretroviral Therapy," *Journal of General Virology*, 2003; 84:2217-2228.

Whitcombe et al., "Detection of PCR Products Using Self-Probing Amplicons and Fluorescence," *Nature Biotechnology*, 1999; 17:804-807.

Wild et al., "A Synthetic Peptide Inhibitor of Human Immunodeficiency Virus Replication: Correlation Between Solution Structure and Viral Inhibition," *Proc. Natl. Acad. Sci.*, 1992; 89:10537-10541.

Wrin et al., "Measuring the Replicative Fitness of Recombinant HIV-1 Vectors Expressing Protease and Reverse Transcriptase Derived from Patient Viruses," *7th Conference on Retroviruses and Opportunistic Infections*, San Francisco, CA, 2000; Abstract 233.

\* cited by examiner

SEQUENCE LISTING

<160> NUMBER OF SEQ ID NOS: 29

<210> SEQ ID NO 1
<211> LENGTH: 48
<212> TYPE: DNA
<213> ORGANISM: Human immunodeficiency virus

<400> SEQUENCE: 1
tcgggtttat tacagggact cacgtaatcc actttggaaa ggaccagc          48

<210> SEQ ID NO 2
<211> LENGTH: 48
<212> TYPE: DNA
<213> ORGANISM: Human immunodeficiency virus

<400> SEQUENCE: 2
gctggtcctt tccaaagtgg attacgtgag tccctgtaat aaacccga          48

<210> SEQ ID NO 3
<211> LENGTH: 43
<212> TYPE: DNA
<213> ORGANISM: Human immunodeficiency virus

<400> SEQUENCE: 3
ccgagatctt caggcccgga ggaggtgaca tgagggacaa ttg               43

<210> SEQ ID NO 4
<211> LENGTH: 43
<212> TYPE: DNA
<213> ORGANISM: Human immunodeficiency virus

<400> SEQUENCE: 4
caattgtccc tcatgtcacc tcctccgggc tgaagatct cgg                43

<210> SEQ ID NO 5
<211> LENGTH: 18
<212> TYPE: DNA
<213> ORGANISM: Human immunodeficiency virus

<400> SEQUENCE: 5
atgtcacctc ctccgggc                                          18

<210> SEQ ID NO 6
<211> LENGTH: 18
<212> TYPE: DNA
<213> ORGANISM: Human immunodeficiency virus

<400> SEQUENCE: 6
caggaatgct tgctgctg                                          18

<210> SEQ ID NO 7
<211> LENGTH: 18
<212> TYPE: DNA
<213> ORGANISM: Human immunodeficiency virus

<400> SEQUENCE: 7
atatctcctc ctccaggt                                          18

<210> SEQ ID NO 8
<211> LENGTH: 22
<212> TYPE: DNA
<213> ORGANISM: Human immunodeficiency virus

```
<400> SEQUENCE: 8
acaggcaact tggcaaatca aa                                              22

<210> SEQ ID NO 9
<211> LENGTH: 23
<212> TYPE: DNA
<213> ORGANISM: Human immunodeficiency virus

<400> SEQUENCE: 9
tgcagaataa aacaaattat aaa                                             23

<210> SEQ ID NO 10
<211> LENGTH: 24
<212> TYPE: DNA
<213> ORGANISM: Human immunodeficiency virus

<400> SEQUENCE: 10
cagcagtaca aatggcagta ttca                                            24

<210> SEQ ID NO 11
<211> LENGTH: 23
<212> TYPE: DNA
<213> ORGANISM: Human immunodeficiency virus

<400> SEQUENCE: 11
tcctttccaa agtggattac gtg                                             23

<210> SEQ ID NO 12
<211> LENGTH: 22
<212> TYPE: DNA
<213> ORGANISM: Human immunodeficiency virus

<400> SEQUENCE: 12
tttccaaagt ggatttctgc tg                                              22

<210> SEQ ID NO 13
<211> LENGTH: 35
<212> TYPE: DNA
<213> ORGANISM: Human immunodeficiency virus

<400> SEQUENCE: 13
atatctcctc ctccaggtac aacgagaggc gtgat                                35

<210> SEQ ID NO 14
<211> LENGTH: 38
<212> TYPE: DNA
<213> ORGANISM: Human immunodeficiency virus

<400> SEQUENCE: 14
ctgggaggaa ggctagctct gaagatctcg gactcatt                             38

<210> SEQ ID NO 15
<211> LENGTH: 38
<212> TYPE: DNA
<213> ORGANISM: Human immunodeficiency virus

<400> SEQUENCE: 15
cttctccaat tgtccctcat acaacgagag gaaacctt                             38

<210> SEQ ID NO 16
<211> LENGTH: 33
<212> TYPE: DNA
<213> ORGANISM: Human immunodeficiency virus
```

```
<400> SEQUENCE: 16
tgcccaggga ggctagctgt cacctcctcc ggg                          33

<210> SEQ ID NO 17
<211> LENGTH: 21
<212> TYPE: DNA
<213> ORGANISM: Human immunodeficiency virus

<400> SEQUENCE: 17
atcacgcctc gutcctccca g                                       21

<210> SEQ ID NO 18
<211> LENGTH: 22
<212> TYPE: DNA
<213> ORGANISM: Human immunodeficiency virus

<400> SEQUENCE: 18
aaggtttcct cguccctggg ca                                      22

<210> SEQ ID NO 19
<211> LENGTH: 21
<212> TYPE: DNA
<213> ORGANISM: Human immunodeficiency virus

<400> SEQUENCE: 19
attaacaaga gatggtggta a                                       21

<210> SEQ ID NO 20
<211> LENGTH: 21
<212> TYPE: DNA
<213> ORGANISM: Human immunodeficiency virus

<400> SEQUENCE: 20
gtgctactcc taatggttca a                                       21

<210> SEQ ID NO 21
<211> LENGTH: 39
<212> TYPE: DNA
<213> ORGANISM: Human immunodeficiency virus

<400> SEQUENCE: 21
caaacgagtc ctggccttgt ctacaacgag gttgtgctg                    39

<210> SEQ ID NO 22
<211> LENGTH: 39
<212> TYPE: DNA
<213> ORGANISM: Human immunodeficiency virus

<400> SEQUENCE: 22
cggttggtga ggctagctgt ggagacggat tacaccttc                    39

<210> SEQ ID NO 23
<211> LENGTH: 21
<212> TYPE: DNA
<213> ORGANISM: Human immunodeficiency virus

<400> SEQUENCE: 23
cagcacaacc gucaccaacc g                                       21

<210> SEQ ID NO 24
<211> LENGTH: 20
<212> TYPE: DNA
<213> ORGANISM: Human immunodeficiency virus
```

-continued

```
<400> SEQUENCE: 24
cattctatca tcaacgggta                                                  20

<210> SEQ ID NO 25
<211> LENGTH: 18
<212> TYPE: DNA
<213> ORGANISM: Human immunodeficiency virus

<400> SEQUENCE: 25
caaaggcaga tggatcag                                                    18

<210> SEQ ID NO 26
<211> LENGTH: 2571
<212> TYPE: DNA
<213> ORGANISM: Human immunodeficiency virus

<400> SEQUENCE: 26
atgagagtga aggagaaata tcagcacttg tggagatggg ggtggagatg gggcaccatg      60
ctccttggga tgttgatgat ctgtagtgct acagaaaaat tgtgggtcac agtctattat    120
ggggtacctg tgtggaagga agcaaccacc actctatttt gtgcatcaga tgctaaagca    180
tatgatacag aggtacataa tgtttgggcc acacatgcct gtgtacccac agaccccaac    240
ccacaagaag tagtattggt aaatgtgaca gaaaatttta acatgtggaa aaatgacatg    300
gtagaacaga tgcatgagga tataatcagt ttatgggatc aaagcctaaa gccatgtgta    360
aaattaaccc cactctgtgt tagttttaaag tgcactgatt tgaagaatga tactaatacc    420
aatagtagta gcgggagaat gataatggag aaaggagaga taaaaaactg ctctttcaat    480
atcagcacaa gcataagagg taaggtgcag aaagaatatg catttttta taaacttgat    540 ataatacccaa tagataatga tactaccagc tataagttga caagttgtaa cacctcagtc    600
attacacagg cctgtccaaa ggtatccttt gagccaattc ccatacatta ttgtgccccg    660
gctggttttg cgattctaaa atgtaataat aagacgttca tggaacagg accatgtaca    720 aatgtcagca cagtacaatg tacacatgga attaggccag tagtatcaac tcaactgctg    780
ttaaatggca gtctagcaga agaagaggta gtaattgat ctgtcaattt cacggacaat    840
gctaaaacca atatagtaca gctgaacaca tctgtagaaa ttaattgtac aagacccaac    900
aacaatacaa gaaaaagaat ccgtatccag agaggaccag ggagagcatt tgttacaata    960
ggaaaaatag gaaatatgag acaagcacat tgtaacatta gtagagcaaa atggaataac   1020
actttaaaac agatagctag caaattaaga gaacaatttg gaataataaa acaataatc   1080 tttaagcaat cctcaggagg ggacccagaa attgtaacgc acagttttaa ttgtggaggg   1140
gaatttttct actgtaattc aacacaactg tttaatagta cttggtttaa tagtacttgg   1200
agtactgaag ggtcaaataa cactgaagga agtgacacaa tcaccctccc atgcagaata   1260
aaacaaatta taaacatgtg gcagaaagta ggaaaagcaa tgtatgcccc tcccatcagt   1320
ggacaaatta gatgttcatc aaatattaca gggctgctat taacaagaga tggtggtaat   1380
agcaacaatg agtccgagat cttcaggccc ggaggaggtg acatgaggga caattggaga   1440
agtgaattat ataaatataa agtagtaaaa attgaaccat taggagtagc acccaccaag   1500
gcaaagagaa gagtggtgca gagagaaaaa agagcagtgg aataggagc tttgttcctt   1560 gggttcttgg gagcagcagg aagcactatg ggcgcagcgt caatgacgct gacggtacag   1620
gccagacaat tattgtctgg tatagtgcag cagcagaaca atttgctgag ggctattgag   1680
gcgcaacagc atctgttgca actcacagtc tggggcatca agcagctcca ggcaagaatc   1740
```

| | |
|---|---|
| ctggctgtgg aaagatacct aaaggatcaa cagctcctgg ggatttgggg ttgctctgga | 1800 |
| aaactcattt gcaccactgc tgtgccttgg aatgctagtt ggagtaataa atctctggaa | 1860 |
| cagatttgga atcacacgac ctggatggag tgggacagag aaattaacaa ttacacaagc | 1920 |
| ttaatacact ccttaattga agaatcgcaa aaccagcaag aaaagaatga acaagaatta | 1980 |
| ttggaattag ataaatgggc aagtttgtgg aattggttta acataacaaa ttggctgtgg | 2040 |
| tatataaaat tattccataat gatagtagga ggcttggtag gtttaagaat agttttgct | 2100 |
| gtactttcta tagtgaatag agttaggcag ggatattcac cattatcgtt tcagacccac | 2160 |
| ctcccaaccc cgaggggacc cgacaggccc gaaggaatag aagaagaagg tggagagaga | 2220 |
| gacagagaca gatccattcg attagtgaac ggatccttgg cacttatctg ggacgatctg | 2280 |
| cggagcctgt gcctcttcag ctaccaccgc ttgagagact tactcttgat tgtaacgagg | 2340 |
| attgtggaac ttctgggacg caggggggtgg gaagccctca aatattggtg gaatctccta | 2400 |
| cagtattgga gtcaggaact aaagaatagt gctgttagct tgctcaatgc cacagccata | 2460 |
| gcagtagctg aggggacaga tagggttata gaagtagtac aaggagcttg tagagctatt | 2520 |
| cgccacatac ctagaagaat aagacagggc ttggaaagga ttttgctata a | 2571 |

<210> SEQ ID NO 27
<211> LENGTH: 867
<212> TYPE: DNA
<213> ORGANISM: Human immunodeficiency virus

<400> SEQUENCE: 27

| | |
|---|---|
| tttttagatg gaatagataa ggcccaagat gaacatgaga aatatcacag taattggaga | 60 |
| gcaatggcta gtgattttaa cctgccacct gtagtagcaa aagaaatagt agccagctgt | 120 |
| gataaatgtc agctaaaagg agaagccatg catggacaag tagactgtag tccaggaata | 180 |
| tggcaactag attgtacaca tttagaagga aaagttatcc tggtagcagt tcatgtagcc | 240 |
| agtggatata tagaagcaga agttattcca gcagaaacag ggcaggaaac agcatatttt | 300 |
| cttttaaaat tagcaggaag atggccagta aaaacaatac atacagacaa tggcagcaat | 360 |
| ttcaccagtg ctacggttaa ggccgcctgt tggtgggcgg gaatcaagca ggaatttgga | 420 |
| attccctaca atccccaaag tcaaggagta gtagaatcta tgaataaaga attaaagaaa | 480 |
| attataggac aggtaagaga tcaggctgaa catcttaaga cagcagtaca aatggcagta | 540 |
| ttcatccaca attttaaaag aaaagggggg attggggggt acagtgcagg ggaaagaata | 600 |
| gtagacataa tagcaacaga catacaaact aaagaattac aaaaacaaat tacaaaaatt | 660 |
| caaaattttc gggtttatta cagggactca cgtaatccac tttggaaagg accagcaaag | 720 |
| ctcctctgga aaggtgaagg ggcagtagta atacaagata atagtgacat aaaagtagtg | 780 |
| ccaagaagaa aagcaaagat cattagggat tatggaaaac agatggcagg tgatgattgt | 840 |
| gtggcaagta gacaggatga ggattag | 867 |

<210> SEQ ID NO 28
<211> LENGTH: 13741
<212> TYPE: DNA
<213> ORGANISM: Human immunodeficiency virus

<400> SEQUENCE: 28

| | |
|---|---|
| agcttgcatg cctgcaggtc gactctagag aacgctaata catttcccta ctattctatc | 60 |
| aactataggg cctcctagct accttctttg ggtcactggt ttgccatttt aattaaaatc | 120 |
| aactagtaga gatacatttt aagaaaaaca ctgtatgtgt gtgtacatac acacacacac | 180 |

```
atgtatgtgt ataatataca tatatatgta tgtgtataat atacatatat atgtatgtgt    240
ataatataca tatatatgta tgtgtataat atacatatat atgtatgtgt ataatataca    300
tatgtatatg tatatgtata tatgtatctg tgtatatatc ttgcatttt gtaagaaaaa     360 aacagaaaat atagaagttt tcaagaacta acactttctt acataacaaa gcagaaatgt    420
tcgaactacg taactaaaat gatgaaaaaa ttcccagtat cactgcctgt tggtgtggc     480 tatcagaggt ttattttccc cctttcttgt ttgcttttct ttaagtcaat ctggccccca    540
tggcctctga ctctgtgact cggcaccagc gctgtggccc cttcatttac atttgataac    600
tgtagagaga ttaattataa tcctgctcat tagacagatc aatctgaagt tggcaagttt    660
ttaaatataa ctacctagca ttttaaaaa gggatgcctt tacagtttag ttaacaatat     720
atactgcaca ttttgttttt aaaaggcctg tttactacca ctgattaact atatacttac    780
tgaggcaact ccttcttttg ttttattcaa atatttactg agtaccagga ctcctgtgtg    840
ctaatacaat ggtgctctac tttctgcacc tatatactag ggagaccaag cactatcacc    900
catacctctg agagtagctt ccctaactgg gttactcctg agttaactgg ataactcaag    960
ctaaccaaaa tcatcccaaa cttcccaccc catacctat taccactgcc aattacctgt    1020
ggtttcattt actctaaacc tgtgattcct ctgaattatt ttcatttaa agaaattgta    1080 tttgttaaat atgtactaca aacttagtag ttggaagggc taattcactc ccaaagaaga    1140
caagatatcc ttgatctgtg gatctaccac acacaaggct acttccctga ttagcagaac    1200
tacacaccag ggccaggggt cagatatcca ctgacctttg gatggtgcta caagctagta    1260
ccagttgagc cagataaggt agaagaggcc aataaaggag agaacaccag cttgttacac    1320
cctgtgagcc tgcatgggat ggatgacccg gagagagaag tgttagagtg gaggtttgac    1380
agccgcctag catttcatca cgtggcccga gagctgcatc cggagtactt caagaactgc    1440
tgatatcgag cttgctacaa gggactttcc gctggggact ttccaggag gcgtggcctg     1500 ggcgggactg gggagtggcg agccctcaga tcctgcatat aagcagctgc ttttgcctg     1560 tactgggtct ctctggttag accagatctg agcctgggag ctctctggct aactagggaa    1620
cccactgctt aagcctcaat aaagcttgcc ttgagtgctt caagtagtgt gtgcccgtct    1680
gttgtgtgac tctggtaact agagatccct cagacccttt tagtcagtgt ggaaaatctc    1740
tagcagtggc gcccgaacag ggacttgaaa gcgaaaggga accagagga gctctctcga     1800 cgcaggactc ggcttgctga agcgcccgca cggcaagagg cgaggggcgg cgactggtga    1860
gtacgccaaa aattttgact agcggaggct agaaggagag atgggtgc gagagcgtca     1920 gtattaagcg ggggagaatt agatcgatgg gaaaaaattc ggttaaggcc agggggaaag    1980
aaaaaatata aattaaaaca tatagtatgg gcaagcaggg agctagaacg attcgcagtt    2040
aatcctggcc tgttagaaac atcagaaggc tgtagacaaa tactgggaca gctacaacca    2100
tcccttcaga caggatcaga agaacttaga tcattatata atacagtagc aaccctctat    2160
tgtgtgcatc aaaggataga gataaaagac accaaggaag ctttagacaa gatagaggaa    2220
gagcaaaaca aaagtaagaa aaaagcacag caagcagcag ctgacacagg acacagcaat    2280
caggtcagcc aaaattaccc tatagtgcag aacatccagg ggcaaatggt acatcaggcc    2340
atatcaccta gaacttaaa tgcatgggta aaagtagtag aagagaaggc tttcagccca     2400
gaagtgatac ccatgttttc agcattatca gaaggagcca ccccacaaga tttaaacacc    2460
atgctaaaca cagtgggggg acatcaagca gccatgcaaa tgttaaaaga gaccatcaat    2520
gaggaagctg cagaatggga tagagtgcat ccagtgcatg cagggcctat tgcaccaggc    2580
```

```
cagatgagag aaccaagggg aagtgacata gcaggaacta ctagtaccct tcaggaacaa   2640
ataggatgga tgacaaataa tccacctatc ccagtaggaa aaatttataa aagatggata   2700
atcctgggat taaataaaat agtaagaatg tatagcccta ccagcattct ggacataaga   2760
caaggaccaa aggaaccctt tagagactat gtagaccggt tctataaaac tctaagagcc   2820
gagcaagctt cacaggaggt aaaaaattgg atgacagaaa ccttgttggt ccaaaatgcg   2880
aacccagatt gtaagactat tttaaaagca ttgggaccag cggctacact agaagaaatg   2940
atgacagcat gtcagggagt aggaggaccc ggccataagg caagagtttt ggctgaagca   3000
atgagccaag taacaaattc agctaccata atgatgcaga gaggcaattt taggaaccaa   3060
agaaagattg ttaagtgttt caattgtggc aaagaagggc acacagccag aaattgcagg   3120
gcccctagga aaaagggctg ttggaaatgt ggaaaggaag gtcacctgga ttcctgagtg   3180
ggagtttgtt aataccc ctc ccttagtgaa attatggtac cagttagaga agaacccat   3240 agtaggagca gaaccttct atgtagatgg ggcagctaac agggagacta aattaggaaa   3300
agcaggatat gttactaata gaggaagaca aaaagttgtc accctaactg acacaacaaa   3360
tcagaagact gagttacaag caattta tct agctttgcag gattcgggat tagaagtaaa   3420
catagtaaca gactcacaat atgcattagg aatcattcaa gcacaaccag atcaaagtga   3480
atcagagtta gtcaatcaaa taatagagca gttaataaaa aaggaaaagg tctatctggc   3540
atgggtacca gcacacaaag gaattggagg aaatgaacaa gtagataaat tagtcagtgc   3600
tggaatcagg aaagtactat ttttagatgg aatagataag gcccaagatg aacatgagaa   3660
atatcacagt aattggagag caatggctag tgattttaac ctgccacctg tagtagcaaa   3720
agaaatagta gccagctgtg ataaatgtca gctaaaagga gaagccatgc atggacaagt   3780
agactgtagt ccaggaatat ggcaactaga ttgtacacat ttagaaggaa aagttatcct   3840
ggtagcagtt catgtagcca gtggatatat agaagcagaa gttattccag cagaaacagg   3900
gcaggaaaca gcatattttc ttttaaaatt agcaggaaga tggccagtaa aaacaataca   3960
tacagacaat ggcagcaatt tcaccagtgc tacggttaag gccgcctgtt ggtgggcggg   4020
aatcaagcag gaatttggaa ttccctacaa tccccaaagt caaggagtag tagaatctat   4080
gaataaagaa ttaaagaaaa ttataggaca ggtaagagat caggctgaac atcttaagac   4140
agcagtacaa atggcagtat tcatccacaa ttttaaaaga aaaggggggga ttggggggta   4200 cagtgcaggg gaaagaatag tagacataat agcaacagac atacaaacta agaattaca   4260 aaaacaaatt acaaaaattc aaaattttcg ggtttattac agggacagca gaaatccact   4320
ttggaaagga ccagcaaagc tcctctggaa aggtgaaggg gcagtagtaa tacaagataa   4380
tagtgacata aaagtagtgc caagaagaaa agcaaagatc attagggatt atggaaaaca   4440
gatggcaggt gatgattgtg tggcaagtag acaggatgag gattagaaca tggaaaagtt   4500
tagtaaaaca ccatatgtat gtttcaggga agctagggg atggttttat agacatcact   4560
atgaaagccc tcatccaaga ataagttcag aagtacacat cccactaggg gatgctagat   4620
tggtaataac aacatattgg ggtctgcata caggagaaag agactggcat ttgggtcagg   4680
gagtctccat agaatggagg aaaaagagat atagcacaca agtagaccct gaactagcag   4740
accaactaat tcatctgtat tactttgact gtttttcaga ctctgctata gaaaggcct   4800 tattaggaca catagttagc cctaggtgtg aatatcaagc aggacataac aaggtaggat   4860
ctctacaata cttggcacta gcagcattaa taacaccaaa aaagataaag ccacctttgc   4920
ctagtgttac gaaactgaca gaggatagat ggaacaagcc ccagaagacc aagggccaca   4980
```

-continued

```
gagggagcca cacaatgaat ggacactaga gcttttagag gagcttaaga atgaagctgt   5040
tagacatttt cctaggattt ggctccatgg cttagggcaa catatctatg aaacttatgg   5100
ggatacttgg gcaggagtgg aagccataat aagaattctg caacaactgc tgtttatcca   5160
ttttcagaat tgggtgtcga catagcagaa taggcgttac tcgacagagg agagcaagaa   5220
atggagccag tagatcctag actagagccc tggaagcatc caggaagtca gcctaaaact   5280
gcttgtacca attgctattg taaaaagtgt tgctttcatt gccaagtttg tttcataaca   5340
aaagccttag gcatctccta tggcaggaag aagcggagac agcgacgaag agctcatcag   5400
aacagtcaga ctcatcaagc ttctctatca aagcagtaag tagtacatgt aacgcaacct   5460
ataccaatag tagcaatagt agcattagta gtagcaataa taatagcaat agttgtgtgg   5520
tccatagtaa tcatagaata taggaaaata ttaagacaaa gaaaaataga caggttaatt   5580
gatagactaa tagaaagagc agaagacagt ggcaatgaga gtgaaggaga aatatcagca   5640
cttgtggaga tgggggtgga gatggggcac catgctcctt gggatgttga tgatctgtag   5700
tgctacagaa aaattgtggg tcacagtcta ttatgggta cctgtgtgga aggaagcaac   5760
caccactcta ttttgtgcat cagatgctaa agcatatgat acagaggtac ataatgtttg   5820
ggccacacat gcctgtgtac ccacagaccc caacccacaa gaagtagtat tggtaaatgt   5880
gacagaaaat tttaacatgt ggaaaaatga catggtagaa cagatgcatg aggatataat   5940
cagtttatgg gatcaaagcc taaagccatg tgtaaaatta ccccactct gtgttagttt   6000 aaagtgcact gatttgaaga atgatactaa taccaatagt agtagcggga gaatgataat   6060
ggagaaagga gagataaaaa actgctcttt caatatcagc acaagcataa gaggtaaggt   6120
gcagaaagaa tatgcatttt tttataaact tgatataata ccaatagata atgatactac   6180
cagctataag ttgacaagtt gtaacacctc agtcattaca caggcctgtc caaaggtatc   6240
ctttgagcca attcccatac attattgtgc cccggctggt tttgcgattc taaaatgtaa   6300
taataagacg ttcaatggaa caggaccatg tacaaatgtc agcacagtac aatgtacaca   6360
tggaattagg ccagtagtat caactcaact gctgttaaat ggcagtctag cagaagaaga   6420
ggtagtaatt agatctgtca atttcacgga caatgctaaa accataatag tacagctgaa   6480
cacatctgta gaaattaatt gtacaagacc caacaacaat acaagaaaaa gaatccgtat   6540
ccagagagga ccagggagag catttgttac aataggaaaa ataggaaata tgagacaagc   6600
acattgtaac attagtagag caaaatggaa taacacttta aaacagatag ctagcaaatt   6660
aagagaacaa tttggaaata taaaacaat aatctttaag caatcctcag gaggggaccc   6720
agaaattgta acgcacagtt ttaattgtgg aggggaattt ttctactgta attcaacaca   6780
actgtttaat agtacttggt ttaatagtac ttggagtact gaagggtcaa ataacactga   6840
aggaagtgac acaatcaccc tcccatgcag aataaaacaa attataaaca tgtggcagaa   6900
agtaggaaaa gcaatgtatg cccctcccat cagtggacaa attagatgtt catcaaatat   6960
tacagggctg ctattaacaa gagatggtgg taatagcaac aatgagtccg agatcttcag   7020
gcccggagga ggtgacatga gggacaattg gagaagtgaa ttatataaat ataaagtagt   7080
aaaaattgaa ccattaggag tagcacccac caaggcaaag agaagagtgg tgcagagaga   7140
aaaaagagca gtgggaatag gagctttgtt ccttgggttc ttgggagcag caggaagcac   7200
tatgggcgca gcgtcaatga cgctgacggt acaggccaga caattattgt ctggtatagt   7260
gcagcagcag aacaatttgc tgagggctat tgaggcgcaa cagcatctgt tgcaactcac   7320
agtctggggc atcaagcagc tccaggcaag aatcctggct gtggaaagat acctaaagga   7380
```

```
tcaacagctc ctggggatttt ggggttgctc tggaaaactc atttgcacca ctgctgtgcc   7440
ttggaatgct agttggagta ataaatctct ggaacagatt tggaatcaca cgacctggat   7500
ggagtgggac agagaaatta acaattacac aagcttaata cactccttaa ttgaagaatc   7560
gcaaaccag caagaaaaga atgaacaaga attattggaa ttagataaat gggcaagttt   7620
gtggaattgg tttaacataa caaattggct gtggtatata aaattattca taatgatagt   7680
aggaggcttg gtaggtttaa gaatagtttt tgctgtactt tctatagtga atagagttag   7740
gcagggatat tcaccattat cgtttcagac ccacctccca accccgaggg acccgacag    7800
gcccgaagga atagaagaag aaggtggaga gagagacaga gacagatcca ttcgattagt   7860
gaacggatcc ttggcactta tctgggacga tctgcggagc ctgtgcctct tcagctacca   7920
ccgcttgaga gacttactct tgattgtaac gaggattgtg gaacttctgg gacgcagggg   7980
gtgggaagcc ctcaaatatt ggtggaatct cctacagtat tggagtcagg aactaaagaa   8040
tagtgctgtt agcttgctca atgccacagc catagcagta gctgagggga cagatagggt   8100
tatagaagta gtacaaggag cttgtagagc tattcgccac atacctagaa gaataagaca   8160
gggcttggaa aggatttttgc tataagatgg gtggcaagtg gtcaaaaagt agtgtgattg   8220
gatggcctac tgtaagggaa agaatgagac gagctgagcc agcagcagat agggtgggag   8280
cagcatctcg agacctggaa aaacatggag caatcacaag tagcaataca gcagctacca   8340
atgctgcttg tgcctggcta gaagcacaag aggaggagga ggtgggtttt ccagtcacac   8400
ctcaggtacc tttaagacca atgacttaca aggcagctgt agatcttagc cacttttaa    8460
aagaaaaggg gggactggaa gggctaattc actcccaaag aagacaagat atccttgatc   8520
tgtggatcta ccacacacaa ggctacttcc ctgattgaca gaactacaca ccagggccag   8580
gggtcagata tccactgacc tttggatggt gctacaagct agtaccagtt gagccagata   8640
aggtagaaga ggccaataaa ggagagaaca ccagcttgtt acaccctgtg agcctgcatg   8700
ggatggatga cccggagaga gaagtgttag agtggaggtt tgacagccgc ctagcatttc   8760
atcacgtggc ccgagagctg catccggagt acttcaagaa ctgctgatat cgagcttgct   8820
acaagggact ttccgctggg gactttccag ggaggcgtgg cctgggcggg actggggagt   8880
ggcgagccct cagatcctgc atataagcag ctgcttttg cctgtactgg gtctctctgg   8940
ttagaccaga tctgagcctg ggagctctct ggctaactag ggaacccact gcttaagcct   9000
caataaagct tgccttgagt gcttcaagta gtgtgtgccc gtctgttgtg tgactctggt   9060
aactagagat ccctcagacc cttttagtca gtgtggaaaa tctctagcag tagtagttca   9120
tgtcatctta ttattcagta tttataactt gcaaagaaat gaatatcaga gagtgagagg   9180
ccttgacatt ataatagatt tagcaggaat tgaactagga gtggagcaca caggcaaagc   9240
tgcagaagta cttggaagaa gccaccagag atactcacga ttctgcacat acctggctaa   9300
tcccagatcc taaggattac attaagttta ctaacatttta tataatgatt tatagtttaa   9360
agtataaact tatctaattt actattctga cagatattaa ttaatcctca aatatcataa   9420
gagatgatta ctattatccc catttaacac aagaggaaac tgagagggaa agatgttgaa   9480
gtaattttcc cacaattaca gcatccgtta gttacgactc tatgatcttc tgacacaaat   9540
tccatttact cctcacccta tgactcagtc gaatatatca agttatgga cattatgcta    9600
agtaacaaat taccctttta tatagtaaat actgagtaga ttgagagaag aaattgtttg   9660
caaacctgaa tagcttcaag aagaagagaa gtgaggataa gaataacagt tgtcatttaa   9720
caagttttaa caagtaactt ggttagaaag ggattcaaat gcataaagca agggataaat   9780
```

-continued

```
ttttctggca acaagactat acaatataac cttaaatatg acttcaaata attgttggaa     9840
cttgataaaa ctaattaaat attattgaag attatcaata ttataaatgt aatttacttt     9900
taaaaaggga acatagaaat gtgtatcatt agagtagaaa acaatcctta ttatcacaat     9960
ttgtccaaac aagtttgtta ttaacacaag tagaatactg cattcaatta agttgactgc    10020
agattttgtg ttttgttaaa attagaaaga gataacaaca atttgaatta ttgaaagtaa    10080
catgtaaata gttctacata cgttcttttg acatcttgtt caatcattga tcggaagttc    10140
tttatcttgg aagaatttgt tccaaagact ctgaataaag gaaaacaatc tattatatag    10200
tctcacacct ttgttttact tttagtgatt tcaatttaat aatgtaaatg gttaaaattt    10260
attcttctct gagatcattt cacattgcag atagaaaacc tgagactggg gtaatttttta   10320 ttaaaatcta atttaatctc agaaacacat ctttattcta acatcaattt ttccagtttg    10380
atattatcat ataaagtcag ccttcctcat ctgcaggttc cacaacaaaa atccaaccaa    10440
ctgtggatca aaatattgg gaaaaaatta aaaatagcaa tacaacaata aaaaaataca     10500
aatcagaaaa acagcacagt ataacaactt tatttagcat ttacaatcta ttaggtatta    10560
taagtaatct agaggatccc cgggtaccga gctcgaattc gccctatagt gagtcgtatt    10620
acaattcact ggccgtcgtt ttacaacgtc gtgactggga aaaccctggc gttacccaac    10680
ttaatcgcct tgcagcacat ccccctttcg ccagctggcg taatagcgaa gaggcccgca    10740
ccgatcgccc ttcccaacag ttgcgcagcc tgaatggcga atggacgcgc cctgtagcgg    10800
cgcattaagc gcggcgggtg tggtggttac gcgcagcgtg accgctacac ttgccagcgc    10860
cctagcgccc gctcctttcg ctttcttccc ttcctttctc gccacgttcg ccggctttcc    10920
ccgtcaagct ctaaatcggg ggctcccttt agggttccga tttagtgctt tacggcacct    10980
cgaccccaaa aaacttgatt agggtgatgg ttcacgtagt gggccatcgc cctgatagac    11040
ggtttttcgc cctttgacgt tggagtccac gttctttaat agtggactct tgttccaaac    11100
tggaacaaca ctcaacccta tctcggtcta ttcttttgat ttataaggga ttttgccgat    11160
ttcggcctat tggttaaaaa atgagctgat ttaacaaaaa tttaacgcga attttaacaa    11220
aatattaacg cttacaattt cctgatgcgg tattttctcc ttacgcatct gtgcggtatt    11280
tcacaccgca tatggtgcac tctcagtaca atctgctctg atgccgcata gttaagccag    11340
ccccgacacc cgccaacacc cgctgacgcg ccctgacggg cttgtctgct cccggcatcc    11400
gcttacagac aagctgtgac cgtctccggg agctgcatgt gtcagaggtt ttcaccgtca    11460
tcaccgaaac gcgcgagacg aaagggcctc gtgatacgcc tatttttata ggttaatgtc    11520
atgataataa tggtttctta gacgtcaggt ggcactttc ggggaaatgt gcgcggaacc     11580
cctatttgtt tatttttcta aatacattca aatatgtatc cgctcatgag acaataaccc    11640
tgataaatgc ttcaataata ttgaaaaagg aagagtatga gtattcaaca tttccgtgtc    11700
gcccttattc ccttttttgc ggcattttgc cttcctgttt ttgctcaccc agaaacgctg    11760
gtgaaagtaa aagatgctga agatcagttg ggtgcacgag tgggttacat cgaactggat    11820
ctcaacagcg gtaagatcct tgagagtttt cgccccgaag aacgttttcc aatgatgagc    11880
acttttaaag ttctgctatg tggcgcggta ttatcccgta ttgacgccgg caagagcaa     11940 ctcggtcgcc gcatacacta ttctcagaat gacttggttg agtactcacc agtcacagaa    12000
aagcatctta cggatggcat gacagtaaga gaattatgca gtgctgccat aaccatgagt    12060
gataacactg cggccaactt acttctgaca acgatcggag gaccgaagga gctaaccgct    12120
tttttgcaca acatggggga tcatgtaact cgccttgatc gttgggaacc ggagctgaat    12180
```

```
gaagccatac caaacgacga gcgtgacacc acgatgcctg tagcaatgcc aacaacgttg   12240
cgcaaactat taactggcga actacttact ctagcttccc ggcaacaatt aatagactgg   12300
atggaggcgg ataaagttgc aggaccactt ctgcgctcgg cccttccggc tggctggttt   12360
attgctgata atctggagc cggtgagcgt gggtctcgcg gtatcattgc agcactgggg   12420
ccagatggta agccctcccg tatcgtagtt atctacacga cggggagtca ggcaactatg   12480
gatgaacgaa atagacagat cgctgagata ggtgcctcac tgattaagca ttggtaactg   12540
tcagaccaag tttactcata tatactttag attgatttaa aacttcattt ttaatttaaa   12600
aggatctagg tgaagatcct ttttgataat ctcatgacca aaatcccttta acgtgagttt   12660
tcgttccact gagcgtcaga ccccgtagaa aagatcaaag gatcttcttg agatcctttt   12720
tttctgcgcg taatctgctg cttgcaaaca aaaaaaccac cgctaccagc ggtggtttgt   12780
ttgccggatc aagagctacc aactcttttt ccgaaggtaa ctggcttcag cagagcgcag   12840
ataccaaata ctgtccttct agtgtagccg tagttaggcc accacttcaa gaactctgta   12900
gcaccgccta catacctcgc tctgctaatc ctgttaccag tggctgctgc cagtggcgat   12960
aagtcgtgtc ttaccgggtt ggactcaaga cgatagttac cggataaggc gcagcggtcg   13020
ggctgaacgg ggggttcgtg cacacagccc agcttggagc gaacgaccta caccgaactg   13080
agatacctac agcgtgagct atgagaaagc gccacgcttc ccgaagggag aaaggcggac   13140
aggtatccgg taagcggcag ggtcggaaca ggagagcgca cgagggagct ccagggggga   13200
aacgcctggt atctttatag tcctgtcggg tttcgccacc tctgacttga gcgtcgattt   13260
ttgtgatgct cgtcaggggg gcggagccta tcgaaaaacg ccagcaacgc ggcctttta   13320
cggttcctgg ccttttgctg gccttttgct cacatgttct ttcctgcgtt atcccctgat   13380
tctgtggata accgtattac cgcctttgag tgagctgata ccgctcgccg cagccgaacg   13440
accgagcgca gcgagtcagt gagcgaggaa gcggaagagc gcccaatacg caaaccgcct   13500
ctccccgcgc gttggccgat tcattaatgc agctggcacg acaggtttcc cgactggaaa   13560
gcgggcagtg agcgcaacgc aattaatgtg agttagctca ctcattaggc accccaggct   13620
ttacacttta tgcttccggc tcgtatgttg tgtggaattg tgagcggata acaatttcac   13680
acaggaaaca gctatgacca tgattacgcc aagctattta ggtgacacta tagaatactc   13740
a                                                                  13741
```

<210> SEQ ID NO 29
<211> LENGTH: 13741
<212> TYPE: DNA
<213> ORGANISM: Human immunodeficiency virus

<400> SEQUENCE: 29

```
agcttgcatg cctgcaggtc gactctagag aacgctaata catttcccta ctattctatc     60
aactataggg cctcctagct accttctttg ggtcactggt ttgccatttt aattaaaatc    120
aactagtaga gatacatttt aagaaaaaca ctgtatgtgt gtgtacatac acacacacac    180
atgtatgtgt ataatataca tatatatgta tgtgtataat atacatatat atgtatgtgt    240
ataatataca tatatatgta tgtgtataat atacatatat atgtatgtgt ataatataca    300
tatgtatatg tatatgtata tatgtatctg tgtatatatc ttgcattttt gtaagaaaaa    360
aacagaaaat atagaagttt tcaagaacta acactttctt acataacaaa gcagaaatgt    420
tcgaactacg taactaaaat gatgaaaaaa ttcccagtat cactgcctgt ttggtgtggc    480
tatcagaggt ttattttccc cctttcttgt ttgcttttct ttaagtcaat ctggccccca    540
```

```
tggcctctga ctctgtgact cggcaccagc gctgtggccc cttcatttac atttgataac    600
tgtagagaga ttaattataa tcctgctcat tagacagatc aatctgaagt tggcaagttt    660
ttaaatataa ctacctagca tttttaaaaa gggatgcctt tacagtttag ttaacaatat    720
atactgcaca ttttgttttt aaaaggcctg tttactacca ctgattaact atatacttac    780
tgaggcaact ccttcttttg ttttattcaa atatttactg agtaccagga ctcctgtgtg    840
ctaatacaat ggtgctctac tttctgcacc tatatactag ggagaccaag cactatcacc    900
catacctctg agagtagctt ccctaactgg gttactcctg agttaactgg ataactcaag    960
ctaaccaaaa tcatcccaaa cttcccaccc catacccat taccactgcc aattacctgt   1020
ggtttcattt actctaaacc tgtgattcct ctgaattatt ttcattttaa agaaattgta   1080
tttgttaaat atgtactaca aacttagtag ttggaagggc taattcactc ccaaagaaga   1140
caagatatcc ttgatctgtg gatctaccac acacaaggct acttccctga ttagcagaac   1200
tacacaccag ggccaggggt cagatatcca ctgacctttg gatggtgcta caagctagta   1260
ccagttgagc cagataaggt agaagaggcc aataaaggag agaacaccag cttgttacac   1320
cctgtgagcc tgcatgggat ggatgacccg gagagagaag tgttagagtg gaggtttgac   1380
agccgcctag catttcatca cgtggcccga gagctgcatc cggagtactt caagaactgc   1440
tgatatcgag cttgctacaa gggactttcc gctgggggact ttccagggag gcgtggcctg   1500
ggcgggactg gggagtggcg agccctcaga tcctgcatat aagcagctgc tttttgcctg   1560
tactgggtct ctctggttag accagatctg agcctgggag ctctctggct aactagggaa   1620
cccactgctt aagcctcaat aaagcttgcc ttgagtgctt caagtagtgt gtgcccgtct   1680
gttgtgtgac tctggtaact agagatccct cagacccttt tagtcagtgt ggaaaatctc   1740
tagcagtggc gcccgaacag ggacttgaaa gcgaaaggga accagagga gctctctcga   1800 cgcaggactc ggcttgctga gcgcccgca cggcaagagg cgaggggcgg cgactggtga   1860
gtacgccaaa aattttgact agcggaggct agaaggagag agatgggtgc gagagcgtca   1920
gtattaagcg gggagaatt agatcgatgg gaaaaaattc ggttaaggcc agggggaaag   1980
aaaaaatata aattaaaaca tatagtatgg gcaagcaggg agctagaacg attcgcagtt   2040
aatcctggcc tgttagaaac atcagaaggc tgtagacaaa tactgggaca gctacaacca   2100
tcccttcaga caggatcaga agaacttaga tcattatata atacagtagc aaccctctat   2160
tgtgtgcatc aaaggataga gataaaagac accaaggaag ctttagacaa gatagaggaa   2220
gagcaaaaca aaagtaagaa aaaagcacag caagcagcgc tgacacagg acacagcaat   2280 caggtcagcc aaaattaccc tatagtgcag aacatccagg ggcaaatggt acatcaggcc   2340
atatcaccta gaactttaaa tgcatgggta aaagtagtag aagagaaggc tttcagccca   2400
gaagtgatac ccatgttttc agcattatca gaaggagcca ccccacaaga tttaaacacc   2460
atgctaaaca cagtgggggg acatcaagca gccatgcaaa tgttaaaaga gaccatcaat   2520
gaggaagctg cagaatggga tagagtgcat ccagtgcatg cagggcctat tgcaccaggc   2580
cagatgagag aaccaagggg aagtgacata gcaggaacta ctagtaccct tcaggaacaa   2640
ataggatgga tgacaaataa tccacctatc ccagtaggag aaatttataa agatggata   2700 atcctgggat taaataaaat agtaagaatg tatagcccta ccagcattct ggacataaga   2760
caaggaccaa aggaacccctt tagagactat gtagaccggt tctataaaac tctaagagcc   2820
gagcaagctt cacaggaggt aaaaaattgg atgacagaaa ccttgttggt ccaaaatgcg   2880
aacccagatt gtaagactat tttaaaagca ttgggaccag cggctacact agaagaaatg   2940
```

```
atgacagcat gtcagggagt aggaggaccc ggccataagg caagagtttt ggctgaagca   3000
atgagccaag taacaaattc agctaccata atgatgcaga gaggcaattt taggaaccaa   3060
agaaagattg ttaagtgttt caattgtggc aaagaagggc acacagccag aaattgcagg   3120
gcccctagga aaaagggctg ttggaaatgt ggaaaggaag gtcacctgga ttcctgagtg   3180
ggagtttgtt ataccccctc ccttagtgaa attatggtac cagttagaga agaacccat    3240 agtaggagca gaaaccttct atgtagatgg ggcagctaac agggagacta aattaggaaa   3300
agcaggatat gttactaata gaggaagaca aaaagttgtc accctaactg acacaacaaa   3360
tcagaagact gagttacaag caatttatct agctttgcag gattcgggat tagaagtaaa   3420
catagtaaca gactcacaat atgcattagg aatcattcaa gcacaaccag atcaaagtga   3480
atcagagtta gtcaatcaaa taatagagca gttaataaaa aaggaaaagg tctatctggc   3540
atgggtacca gcacacaaag gaattggagg aaatgaacaa gtagataaat tagtcagtgc   3600
tggaatcagg aaagtactat ttttagatgg aatagataag gcccaagatg aacatgagaa   3660
atatcacagt aattggagag caatggctag tgattttaac ctgccacctg tagtagcaaa   3720
agaaatagta gccagctgtg ataaatgtca gctaaaagga gaagccatgc atggacaagt   3780
agactgtagt ccaggaatat ggcaactaga ttgtacacat ttagaaggaa aagttatcct   3840
ggtagcagtt catgtagcca gtggatatat agaagcagaa gttattccag cagaaacagg   3900
gcaggaaaca gcatattttc ttttaaaatt agcaggaaga tggccagtaa aaacaataca   3960
tacagacaat ggcagcaatt tcaccagtgc tacggttaag gccgcctgtt ggtgggcggg   4020
aatcaagcag gaatttggaa ttccctacaa tccccaaagt caaggagtag tagaatctat   4080
gaataaagaa ttaaagaaaa ttataggaca ggtaagagat caggctgaac atcttaagac   4140
agcagtacaa atggcagtat tcatccacaa ttttaaaaga aaaggggggg ttgggggta    4200 cagtgcaggg gaaagaatag tagacataat agcaacagac atacaaacta agaattaca    4260 aaaacaaatt acaaaaattc aaaattttcg ggtttattac agggactcac gtaatccact   4320
ttggaaagga ccagcaaagc tcctctggaa aggtgaaggg gcagtagtaa tacaagataa   4380
tagtgacata aaagtagtgc caagaagaaa agcaaagatc attagggatt atggaaaaca   4440
gatggcaggt gatgattgtg tggcaagtag acaggatgag gattagaaca tggaaaagtt   4500
tagtaaaaca ccatatgtat gtttcaggga agctagggg atggttttat agacatcact   4560
atgaaagccc tcatccaaga ataagttcag aagtacacat cccactaggg gatgctagat   4620
tggtaataac aacatattgg ggtctgcata caggagaaag agactggcat ttgggtcagg   4680
gagtctccat agaatggagg aaaaagagat atagcacaca agtagaccct gaactagcag   4740
accaactaat tcatctgtat tactttgact gtttttcaga ctctgctata agaaaggcct   4800
tattaggaca catagttagc cctaggtgtg aatatcaagc aggacataac aaggtaggat   4860
ctctacaata cttggcacta gcagcattaa taacaccaaa aaagataaag ccaccttgc    4920 ctagtgttac gaaactgaca gaggatagat ggaacaagcc ccagaagacc aagggccaca   4980
gagggagcca cacaatgaat ggacactaga gcttttagag gagcttaaga atgaagctgt   5040
tagacatttt cctaggattt ggctccatgg cttagggcaa catatctatg aaacttatgg   5100
ggatacttgg gcaggagtgg aagccataat aagaattctg caacaactgc tgtttatcca   5160
ttttcagaat tgggtgtcga catagcagaa taggcgttac tcgacagagg agagcaagaa   5220
atggagccag tagatcctag actagagccc tggaagcatc caggaagtca gcctaaaact   5280
gcttgtacca attgctattg taaaaagtgt tgctttcatt gccaagtttg tttcataaca   5340
```

```
aaagccttag gcatctccta tggcaggaag aagcggagac agcgacgaag agctcatcag    5400
aacagtcaga ctcatcaagc ttctctatca aagcagtaag tagtacatgt aacgcaacct    5460
ataccaatag tagcaatagt agcattagta gtagcaataa taatagcaat agttgtgtgg    5520
tccatagtaa tcatagaata taggaaaata ttaagacaaa gaaaaataga caggttaatt    5580
gatagactaa tagaaagagc agaagacagt ggcaatgaga gtgaaggaga aatatcagca    5640
cttgtggaga tggggtggag atggggcac catgctcctt gggatgttga tgatctgtag     5700
tgctacagaa aaattgtggg tcacagtcta ttatgggta cctgtgtgga aggaagcaac     5760
caccactcta ttttgtgcat cagatgctaa agcatatgat acagaggtac ataatgtttg    5820
ggccacacat gcctgtgtac ccacagaccc caacccacaa gaagtagtat tggtaaatgt    5880
gacagaaaat tttaacatgt ggaaaaatga catggtagaa cagatgcatg aggatataat    5940
cagtttatgg gatcaaagcc taaagccatg tgtaaaatta accccactct gtgttagttt    6000
aaagtgcact gatttgaaga atgatactaa taccaatagt agtagcggga gaatgataat    6060
ggagaaagga gagataaaaa actgctcttt caatatcagc acaagcataa gaggtaaggt    6120
gcagaaagaa tatgcatttt tttataaact tgatataata ccaatagata atgatactac    6180
cagctataag ttgacaagtt gtaacacctc agtcattaca caggcctgtc caaaggtatc    6240
ctttgagcca attcccatac attattgtgc cccggctggt tttgcgattc taaaatgtaa    6300
taataagacg ttcaatggaa caggaccatg tacaaatgtc agcacagtac aatgtacaca    6360
tggaattagg ccagtagtat caactcaact gctgttaaat ggcagtctag cagaagaaga    6420
ggtagtaatt agatctgtca atttcacgga caatgctaaa accataatag tacagctgaa    6480
cacatctgta gaaattaatt gtacaagacc caacaacaat acaagaaaaa gaatccgtat    6540
ccagagagga ccagggagag catttgttac aataggaaaa ataggaaata tgagacaagc    6600
acattgtaac attagtagag caaaatggaa taacacttta aaacagatag ctagcaaatt    6660
aagagaacaa tttggaaata taaaacaat aatctttaag caatcctcag gaggggaccc    6720
agaaattgta acgcacagtt ttaattgtgg aggggaattt ttctactgta attcaacaca    6780
actgtttaat agtacttggt ttaatagtac ttggagtact gaagggtcaa ataacactga    6840
aggaagtgac acaatcaccc tcccatgcag aataaaacaa attataaaca tgtggcagaa    6900
agtaggaaaa gcaatgtatg cccctcccat cagtggacaa attagatgtt catcaaatat    6960
tacagggctg ctattaacaa gagatggtgg taatagcaac aatgagtccg agatcttcag    7020
acctggagga ggagatatga gggacaattg gagaagtgaa ttatataaat ataaagtagt    7080
aaaaattgaa ccattaggag tagcacccac caaggcaaag agaagagtgg tgcagagaga    7140
aaaaagagca gtgggaatag gagctttgtt ccttgggttc ttgggagcag caggaagcac    7200
tatgggcgca gcgtcaatga cgctgacggt acaggccaga caattattgt ctggtatagt    7260
gcagcagcag aacaatttgc tgagggctat tgaggcgcaa cagcatctgt tgcaactcac    7320
agtctggggc atcaagcagc tccaggcaag aatcctggct gtggaaagat acctaaagga    7380
tcaacagctc ctggggattt ggggttgctc tggaaaactc atttgcacca ctgctgtgcc    7440
ttggaatgct agttggagta ataaatctct ggaacagatt tggaatcaca cgacctggat    7500
ggagtgggac agagaaatta acaattacac aagcttaata cactccttaa ttgaagaatc    7560
gcaaaaccag caagaaaaga atgaacaaga attattggaa ttagataaat gggcaagttt    7620
gtggaattgg tttaacataa caattggct gtggtatata aaattattca taatgatagt    7680
aggaggcttg gtaggtttaa gaatagtttt tgctgtactt tctatagtga atagagttag    7740
```

-continued

```
gcagggatat tcaccattat cgtttcagac ccacctccca accccgaggg gacccgacag    7800
gcccgaagga atagaagaag aaggtggaga gagagacaga gacagatcca ttcgattagt    7860
gaacggatcc ttggcactta tctgggacga tctgcggagc ctgtgcctct tcagctacca    7920
ccgcttgaga gacttactct tgattgtaac gaggattgtg gaacttctgg gacgcagggg    7980
gtgggaagcc ctcaaatatt ggtggaatct cctacagtat tggagtcagg aactaaagaa    8040
tagtgctgtt agcttgctca atgccacagc catagcagta gctgagggga cagataggggt   8100 tatagaagta gtacaaggag cttgtagagc tattcgccac atacctagaa gaataagaca    8160
gggcttggaa aggattttgc tataagatgg gtggcaagtg gtcaaaaagt agtgtgattg    8220
gatggcctac tgtaagggaa agaatgagac gagctgagcc agcagcagat agggtgggag    8280
cagcatctcg agacctggaa aaacatggag caatcacaag tagcaataca gcagctacca    8340
atgctgcttg tgcctggcta gaagcacaag aggaggagga ggtgggtttt ccagtcacac    8400
ctcaggtacc tttaagacca atgacttaca aggcagctgt agatcttagc cacttttaa    8460 aagaaaaggg gggactggaa gggctaattc actcccaaag aagacaagat atccttgatc    8520
tgtggatcta ccacacacaa ggctacttcc ctgattgaca gaactacaca ccagggccag    8580
gggtcagata tccactgacc tttggatggt gctacaagct agtaccagtt gagccagata    8640
aggtagaaga ggccaataaa ggagagaaca ccagcttgtt acaccctgtg agcctgcatg    8700
ggatggatga cccggagaga gaagtgttag agtggaggtt tgacagccgc ctagcatttc    8760
atcacgtggc ccgagagctg catccggagt acttcaagaa ctgctgatat cgagcttgct    8820
acaagggact ttccgctggg gactttccag ggaggcgtgg cctgggcggg actggggagt    8880
ggcgagccct cagatcctgc atataagcag ctgcttttg cctgtactgg gtctctctgg    8940
ttagaccaga tctgagcctg ggagctctct ggctaactag ggaacccact gcttaagcct    9000
caataaagct tgccttgagt gcttcaagta gtgtgtgccc gtctgttgtg tgactctggt    9060
aactagagat ccctcagacc cttttagtca gtgtggaaaa tctctagcag tagtagttca    9120
tgtcatctta ttattcagta tttataactt gcaaagaaat gaatatcaga gagtgagagg    9180
ccttgacatt ataatagatt tagcaggaat tgaactagga gtggagcaca caggcaaagc    9240
tgcagaagta cttggaagaa gccaccagag atactcacga ttctgcacat acctggctaa    9300
tcccagatcc taaggattac attaagttta ctaacatttta tataatgatt tatagtttaa    9360
agtataaact tatctaattt actattctga cagatattaa ttaatcctca aatatcataa    9420
gagatgatta ctattatccc catttaacac aagaggaaac tgagagggaa agatgttgaa    9480
gtaattttcc cacaattaca gcatccgtta gttacgactc tatgatcttc tgacacaaat    9540
tccatttact cctcacccta tgactcagtc gaatatatca agttatgga cattatgcta    9600 agtaacaaat tacccttttta tatagtaaat actgagtaga ttgagagaag aaattgtttg    9660
caaacctgaa tagcttcaag aagaagagaa gtgaggataa gaataacagt tgtcatttaa    9720
caagttttaa caagtaactt ggttagaaag ggattcaaat gcataaagca agggataaat    9780
ttttctggca acaagactat acaatataac cttaaatatg acttcaaata attgttggaa    9840
cttgataaaa ctaattaaat attattgaag attatcaata ttataaatgt aatttacttt    9900
taaaagggga acatagaaat gtgtatcatt agagtagaaa acaatcctta ttatcacaat    9960
ttgtccaaac aagtttgtta ttaacacaag tagaatactg cattcaatta agttgactgc   10020 agatttttgtg ttttgttaaa attagaaaga gataacaaca atttgaatta ttgaaagtaa   10080
catgtaaata gttctacata cgttcttttg acatcttgtt caatcattga tcggaagttc   10140
```

```
tttatcttgg aagaatttgt tccaaagact ctgaaataag gaaaacaatc tattatatag   10200
tctcacacct ttgttttact tttagtgatt tcaatttaat aatgtaaatg gttaaaattt   10260
attcttctct gagatcattt cacattgcag atagaaaacc tgagactggg gtaatttta    10320 ttaaaatcta atttaatctc agaaacacat ctttattcta acatcaattt ttccagtttg   10380
atattatcat ataaagtcag ccttcctcat ctgcaggttc cacaacaaaa atccaaccaa   10440
ctgtggatca aaatattgg gaaaaaatta aaatagcaa tacaacaata aaaaaataca    10500
aatcagaaaa acagcacagt ataacaactt tatttagcat ttacaatcta ttaggtatta   10560
taagtaatct agaggatccc cgggtaccga gctcgaattc gccctatagt gagtcgtatt   10620
acaattcact ggccgtcgtt ttacaacgtc gtgactggga aaaccctggc gttacccaac   10680
ttaatcgcct tgcagcacat ccccctttcg ccagctggcg taatagcgaa gaggcccgca   10740
ccgatcgccc ttcccaacag ttgcgcagcc tgaatggcga atggacgcgc cctgtagcgg   10800
cgcattaagc gcggcgggtg tggtggttac gcgcagcgtg accgctacac ttgccagcgc   10860
cctagcgccc gctcctttcg ctttcttccc ttcctttctc gccacgttcg ccggctttcc   10920
ccgtcaagct ctaaatcggg ggctcccttt agggttccga tttagtgctt tacggcacct   10980
cgaccccaaa aaacttgatt agggtgatgg ttcacgtagt gggccatcgc cctgatagac   11040
ggtttttcgc cctttgacgt tggagtccac gttctttaat agtggactct tgttccaaac   11100
tggaacaaca ctcaacccta tctcggtcta ttcttttgat ttataaggga ttttgccgat   11160
ttcggcctat tggttaaaaa atgagctgat ttaacaaaaa tttaacgcga atttaacaa    11220 aatattaacg cttacaattt cctgatgcgg tattttctcc ttacgcatct gtgcggtatt   11280
tcacaccgca tatggtgcac tctcagtaca atctgctctg atgccgcata gttaagccag   11340
ccccgacacc cgccaacacc cgctgacgcg ccctgacggg cttgtctgct cccggcatcc   11400
gcttacagac aagctgtgac cgtctccggg agctgcatgt gtcagaggtt ttcaccgtca   11460
tcaccgaaac gcgcgagacg aaagggcctc gtgatacgcc tatttttata ggttaatgtc   11520
atgataataa tggtttctta gacgtcaggt ggcacttttc ggggaaatgt gcgcggaacc   11580
cctatttgtt tatttttcta aatacattca aatatgtatc cgctcatgag acaataaccc   11640
tgataaatgc ttcaataata ttgaaaaagg aagagtatga gtattcaaca tttccgtgtc   11700
gcccttattc ccttttttgc ggcattttgc cttcctgttt ttgctcaccc agaaacgctg   11760
gtgaaagtaa aagatgctga agatcagttg ggtgcacgag tgggttacat cgaactggat   11820
ctcaacagcg gtaagatcct tgagagtttt cgccccgaag aacgttttcc aatgatgagc   11880
acttttaaag ttctgctatg tggcgcggta ttatcccgta ttgacgccgg gcaagagcaa   11940
ctcggtcgcc gcatacacta ttctcagaat gacttggttg agtactcacc agtcacagaa   12000
aagcatctta cggatggcat gacagtaaga gaattatgca gtgctgccat aaccatgagt   12060
gataacactg cggccaactt acttctgaca acgatcggag gaccgaagga gctaaccgct   12120 ttttttgcaca acatggggga tcatgtaact cgccttgatc gttgggaacc ggagctgaat   12180
gaagccatac caaacgacga gcgtgacacc acgatgcctg tagcaatgcc aacaacgttg   12240
cgcaaactat taactggcga actacttact ctagcttccc ggcaacaatt aatagactgg   12300
atggaggcgg ataaagttgc aggaccactt ctgcgctcgg cccttccggc tggctggttt   12360
attgctgata atctggagc cggtgagcgt gggtctcgcg gtatcattgc agcactgggg   12420
ccagatggta agccctcccg tatcgtagtt atctacacga cggggagtca ggcaactatg   12480
gatgaacgaa atagacagat cgctgagata ggtgcctcac tgattaagca ttggtaactg   12540
```

```
tcagaccaag tttactcata tatactttag attgatttaa aacttcattt ttaatttaaa    12600
aggatctagg tgaagatcct tttttgataat ctcatgacca aaatccctta acgtgagttt    12660
tcgttccact gagcgtcaga ccccgtagaa aagatcaaag gatcttcttg agatcctttt    12720
tttctgcgcg taatctgctg cttgcaaaca aaaaaccac cgctaccagc ggtggtttgt     12780
ttgccggatc aagagctacc aactcttttt ccgaaggtaa ctggcttcag cagagcgcag    12840
ataccaaata ctgtccttct agtgtagccg tagttaggcc accacttcaa gaactctgta    12900
gcaccgccta catacctcgc tctgctaatc ctgttaccag tggctgctgc cagtggcgat    12960
aagtcgtgtc ttaccgggtt ggactcaaga cgatagttac cggataaggc gcagcggtcg    13020
ggctgaacgg ggggttcgtg cacacagccc agcttggagc gaacgaccta caccgaactg    13080
agatacctac agcgtgagct atgagaaagc gccacgcttc ccgaagggag aaaggcggac    13140
aggtatccgg taagcggcag ggtcggaaca ggagagcgca cgagggagct tccaggggga    13200
aacgcctggt atctttatag tcctgtcggg tttcgccacc tctgacttga gcgtcgattt    13260
ttgtgatgct cgtcagggg gcggagccta tcgaaaaacg ccagcaacgc ggccttttta     13320
cggttcctgg cctttttgctg gcctttttgct cacatgttct ttcctgcgtt atccctgat    13380 tctgtggata accgtattac cgcctttgag tgagctgata ccgctcgccg cagccgaacg    13440
accgagcgca gcgagtcagt gagcgaggaa gcggaagagc gcccaatacg caaaccgcct     13500
ctccccgcgc gttggccgat tcattaatgc agctggcacg acaggtttcc cgactggaaa    13560
gcgggcagtg agcgcaacgc aattaatgtg agttagctca ctcattaggc acccaggct     13620 ttacacttta tgcttccggc tcgtatgttg tgtggaattg tgagcggata acaatttcac    13680
acaggaaaca gctatgacca tgattacgcc aagctattta ggtgacacta tagaatactc    13740
a                                                                   13741
```

METHODS, PLASMID VECTORS AND PRIMERS FOR ASSESSING HIV VIRAL FITNESS

CROSS-REFERENCE TO RELATED PATENT APPLICATIONS

This application is the National Stage of International Application No. PCT/EP2006/069422 filed Dec. 7, 2006, which claims priority of European Patent Application No. EP05111802.4 filed Dec. 7, 2005. The complete disclosures of the aforementioned related applications are hereby incorporated herein by reference for all purposes.

FIELD OF THE INVENTION

The present invention relates to methods and means for the evaluation of HIV replicative capacity in a given environment. In particular, the invention provides a growth competition assay that can determine relative viral fitness using a recombinant tagged HIV-1 virus system. The methods rely on plasmid vectors, amplicons, primers and probes, and the generation of replication-competent viruses therefrom. Said methods and materials may find use in multiple fields including diagnostics, drug screening, pharmacogenetics and drug development.

BACKGROUND OF THE ART

The ultimate goal of antiretroviral therapy is to suppress HIV-1 replication as much and for as long as possible. Maintaining low-to-undetectable HIV-1 RNA levels will prevent progression to Acquired Immunodeficiency syndrome (AIDS) and minimize the emergence of antiretroviral resistance (Hirsch et al., 1998). However, even highly active antiretroviral therapy (HAART) does not completely suppress HIV-1 replication in all tissue compartments. Effectiveness of every antiretroviral drug is limited by the emergence of drug-resistant variants, frequently showing extensive cross-resistance within each drug class (Miller, 2001; Deeks, 2001; Loveday, 2001). In the absence of antiretroviral therapy (ART), these drug-resistant strains have reduced fitness compared to wild-type (WT) clones within the quasispecies (Coffin, 1995). Fitness is a complex parameter that describes the replicative adaptability of an organism to its environment (reviewed in Domingo and Holland, 1997; Domingo et al. 1999). Usually, an initial decrease in fitness coincides with the appearance of primary substitutions conferring direct drug resistance. Continued drug pressure allows the virus to select secondary mutations that compensate for the primary mutations and restore enzymatic activity of the drug-targeted enzyme [Protease (PR) or Reverse Transcriptase (RT)]. This continual evolution will lead to a recovery in fitness to levels sometimes lower, similar or even higher than that of the WT virus (Hirsch et al., 1998; Nijhuis et al., 2001; Berkhout, 1999a; Clavel et al., 2000; Doyon et al., 1996; Quiñones-Mateu and Arts, 2001). Thus, each clone within the 'swarm' or quasispecies is subject to various selective pressures and has a fitness that reflects a combination of properties, such as activity and stability, in a particular environment. During quasispecies turnover or replication, different genomes are rapidly generated and subjected to a continuous process of competition and selection (Domingo et al., 1999). Newly arising variants of higher fitness often out-compete clones of lower fitness and thus, the quasispecies can rapidly adapt to a changing environment.

Considerable attention has been focused on the relation between drug resistance and viral fitness. Several mutations that confer resistance to antiretroviral agents reduce the replicative capacity and relative fitness of HIV-1 isolates as compared with WT isolates (Croteau et al. J Virol 1997; 71:1089-96; Larder et al. Science 1995; 269:696-9; Harrigan et al. J Virol 1998; 72:3773-8; Kosalaraksa et al. J Virol 1999; 73:5356-63; Wrin et al. Conference on Retroviruses and Opportunistic Infections, San Francisco, Jan. 30-Feb. 2, 2000). The reduced replicative capacity of highly drug-resistant variants of HIV-1 may contribute to persistent immunologic benefits in patients considered to be "failing" antiretroviral therapy (Deeks et al. N Engl J Med 2001; 344:472-80). The relatively rapid replacement of drug-resistant virus by WT virus on interruption of therapy provides evidence that WT virus has a significant fitness advantage over drug-resistant variants in the absence of drug pressure (Devereux et al. AIDS1999; 13(Suppl):F123-7; Verhofstede et al. AIDS 1999; 13:2541-6; Miller et al. AIDS 2000; 14:2857-67). Thus, accumulation of drug resistance mutations in HIV-1 PR and RT significantly impairs viral fitness (Lu et al., J. Acquir. Immune Defic. Syndr. 27:7-13; Martinez-Picado et al., J. Virol. 73:3744-3752). Reduced viral fitness contributes to the continued benefit of antiretroviral therapy despite the presence of high-level drug resistance (Deeks et al., N. Engl. J. Med. 344:472-480). However, not all resistance mutations necessarily reduce viral fitness in the absence of drug. For example, certain mutations selected during therapy with regimen containing a protease inhibitor (PI) can improve viral replication, leading to a mutant that is fitter than the initial WT isolate (Nijhuis et al., Proc. Natl. Acad. Sci. USA 89:10537-10541).

A number of assays have been reported for the estimation of relative viral fitness in vitro. Most of these approaches rely on point mutation assays, direct population sequencing, or depend on the sequencing of a large number of molecular clones to estimate the frequency of WT and mutant alleles in a population (Martinez-Picado et al. J Virol 1999; 73:3744-52; Nijhuis et al. AIDS 1999; 13:2349-59). Alternatively, allele frequency is estimated by analysis of relative peak heights from sequencing chromatogram (Kosalaraksa et al. J Virol 1999). Clonal analysis and point mutation assays tend to be time-consuming and labor-intensive, however. In addition, unique primers need to be designed and validated for each allele studied by the point mutation assay. Although direct population sequencing is more straight-forward, the comparison of relative peak heights on sequencing chromatograms is an imprecise means of estimating allele frequency in a mixed population (Harrigan et al. J Virol 1998; 72:3773-8).

Recombinant virus assays have provided a relatively rapid and reproducible method of isolating HIV from plasma (Kellam et al. J. Virol. 38 (1994), pp. 23-30; Maschera et al. J. Virol. 69 (1995), pp. 5431-5436; Hertogs et al. Antimicrob. Agents Chemother. 42 (1998), pp. 269-276; and Robinson et al. AIDS Res. Hum. Retr. 16 (2000), pp. 1149-1156). The drug target genes PR and/or RT are amplified by production of a cDNA followed by polymerase chain reaction (PCR) and co-transfected with a cloned proviral DNA with a specific deletion in the region corresponding to the amplified region. Overlapping regions in the co-transfected DNA fragments recombine to produce replicative virus. A method for culturing HIV-1 is described by Robinson et al., Journal of Virological Methods, 104 (2002) 147-160; in which all of the Gag gene including the Gag-Pol cleavage sites are derived from the isolate of interest, in addition to the entire PR and RT sequences.

A modified single-cycle recombinant virus assay has been used to determine replicative capacity of different HIV-1 isolates but does not provide actual data on comparative fitness, because this assay does not measure the competitive growth of different viral species (Wrin et al.). In addition, single-cycle recombinant virus assay are limited to HIV-1 clones containing a subject derived gene or specific mutation, and furthermore the viruses tested do not complete full cycle of replications (Quinones-Mateu et al., 2002).

A PCR-based differential probe hybridization assay that uses chemiluminescent detection accurately quantifies the proportion of WT and mutant sequences in a mixture, but specific probes must be designed for each allele of interest (Eastman et al. J Clin Microbiol 1995; 33:2777-80). Sequencing a sufficiently large number of clones to estimate allele frequences is laborious, whereas peak height comparisons are relatively imprecise methods for quantifying mixtures in the virus quasispecies.

Growth competition experiments involve dual infection with two different HIV-1 isolates. Relative fitness of the two virus strains may be directly compared in mixed infections in which each strain is accurately quantified and genetically and/or phenotypically distinguishable from the other. Outgrowth of one isolate over the other is a measure of relative fitness (Holland et al., 1991). Despite being more laborious, growth competition assays provide an accurate estimate of viral fitness by permitting direct comparison of mutant and WT strains. Using this concept of viral competition, different techniques have been developed to quantify the final proportion of two viruses in an in vitro infection setting, and thereby measure relative viral fitness. Many of these methods compare the fitness of HIV-1 clones differing by single amino acid substitutions and must rely on the sequencing of a large number of clones (Sharma and Crumpacker, 1997; Harrigan et al., 1998; Martinez-Picado et al., 1999, 2000; Imamichi et al., 2000). Recent studies have employed more rapid techniques to estimate the relative frequency of two viruses in a population (Quinones-Mateu and Arts, 2001). For example, different versions of the heteroduplex tracking assay (HTA) have been used to accurately detect and quantify two HIV-1 variants in a competition (Quiñones-Mateu et al., 2000; Nelson et al., 2000; Resch et al., 2001). New technologies such as real-time PCR have also been applied to dual viral detection (De Ronde et al., 2001). Quiñones-Mateu et al. (2002) recently developed a novel real-time PCR/TAQMAN® assay that measured the relative production of HIV-1 subtype B strains by direct competition with non-subtype B HIV-1 controls. Lu and Kuritzkes (JAIDS, 27:7-13, May 2001) developed a novel recombinant marker virus assay (RMVA) to detect two HIV-1 clones following growth competition assays. The nef gene was replaced by two different marker genes in RT-deleted proviral clones (hisD or PLAP). Following growth competition experiments, a proportion of the two RMV clones (pHIVdeltaenvBSTEIIdelta nef-hisD and pHIVdeltaenvBSTEIIdelta nef-PLAP) containing different RT coding regions was quantified via real-time PCR for the corresponding marker. However, since the envelope (env) region is the most variable region of the HIV genome, i.e. highest frequency of mutations providing numerous escape mutants to either drugs or neutralizing antibodies, the removal and replacement of the nef gene by an alien gene shall inevitably affect the properties of the original virus. Thus, such a method still fails to provide an in vitro model which can mimic the in vivo effects of target viruses.

There is thus a need for a method for testing viral fitness which is standardized, which can mimic an in vivo setting, is easy to use and easy to quantify in an accurate and precise manner. There is also a need for a method which allows multiplex analyses of a plurality of virus in a single analysis tube.

It is an object of the invention to provide a method for assessing viral fitness which can measure the replicative capacity of a virus in an environment.

It is an object of the invention to provide a method for assessing viral fitness which can measure the competitive growth of different viral species.

It is an object of the invention to provide a method for assessing viral fitness which does not need to employ primers or probes designed and validated for each allele studied.

It is an object of the invention to provide a method for assessing viral fitness which tests the complete full cycle of replication.

It is an object of the invention to provide a method for assessing viral fitness which is precise for quantifying mixtures in the virus quasispecies.

It is an object of the invention to provide a method for assessing viral fitness which is accurate in estimating viral fitness.

It is an object of the invention to provide a model for assessing viral fitness which can mimic in vivo conditions.

WO03/020878 provides oligonucleotide primer sets, probes, and combinations thereof useful for amplifying and detecting HIV-1 target sequences in a test sample.

EP1283272 by Tibotec Pharmaceuticals Ltd. relates to methods and products for the evaluation of HIV treatment. In particular, molecular events at the HIV envelope protein and their effect on therapeutic efficacy of drugs are determined. The methods rely on providing HIV envelope nucleic acid material and evaluating a treatment either through genotyping or phenotyping.

WO03/011334 discloses the use of an HIV Tat protein or polynucleotide; or an HIV Nef protein or polynucleotide; or an HIV Tat protein or polynucleotide linked to an HIV Nef protein or polynucleotide; and an HIV gp120 protein or polynucleotide in the manufacture of a vaccine suitable for a prime-boost delivery for the prophylactic or therapeutic immunisation of humans against HIV, wherein the protein or polynucleotide is delivered via a bombardment approach.

WO00/29611 relates to a method for the subtype and/or species-comprehensive detection of HIV in a sample while using at least one oligonucleotide which contains at least 10 successive nucleotides from (i) a highly preserved region of the LTR region, of the gag gene or of the polgene of HIV, (ii) of a corresponding region of another HIV isolate, (iii) of a corresponding region of a consensus sequence stemming from a plurality of HIV isolates or of sequences complementary thereto.

FR2869045 provides a method of analysis of a sample likely to contain an HIV virus, comprising the following steps: (a) the extraction of the viral RNA; (b) the reverse transcription of the RNA obtained at step (a) and amplification with a first pair of primers thereby allowing the generation of an amplified reverse transcription product comprising the whole or the part of at least two successive genes of the HIV genome; (c) the sequencing of the amplified reverse transcription product; (d) the amplification of the amplified reverse transcription product obtained at step (b) with one second pair of primers; (e) homologous recombination with a vector of the aforesaid amplification product prepared at step (d); (f) functional analysis of viral proteins coded by whole or part of the aforesaid at least two genes; (g) the measurement of the replicative capacity of the recombination viruses obtained at step (e).

EP1285971 by Tibotec Pharmaceuticals Ltd. relates to methods and products for the evaluation of HIV treatment. The methods are based on evaluating molecular events at the HIV integrase (int) resulting in altered therapeutic efficacy of the investigated compounds. The methods rely on providing an integrase gene and evaluating either through genotyping or phenotyping said integrase gene.

US2005/244818 discloses a single-cell-level phenotypic assay, which can simultaneously analyze HIV-1 drug susceptibility and intrinsic replication capacity. This allows quantitative dissection of the functions of antiretroviral drugs into suppression of viral replication and selection of resistant viruses with diminished replication capacities. The disclosed assay provides a tool for the rational evaluation of treatment decisions for patients failing antiretroviral therapy.

Weber Jan et al., The Journal of General Virology, August 2003, vol. 84, no. Pt 8 discloses a TAQMAN® real-time PCR assay to estimate ex vivo human immunodeficiency virus type 1 fitness in the era of multi-target (pol and env) antiretroviral therapy.

WO05/108588 relates to HIV-based recombinant viral clones, which are the result of the following genetic manipulations: deletion of HIV fragments (e.g. the Nef gene) without loss of infective capacity; insertion of a gene that is not expressed in human cells; insertion of the LacZ gene; and introduction of restriction sites in order to extract DNA fragments from the matrix provirus and substitute same with genes from the patients to be assessed. In addition, the invention relates to the application of said clones in analytical methods that are associated with AIDS.

Van Maarseveen et al., Journal of Virological methods, vol. 133, 2006, pages 185-194, disclose a real-time PCR assay to determine relative replication capacity for HIV-1 protease variants and/or reverse transcriptase variants.

SUMMARY OF THE INVENTION

The present invention relates to an ex vivo or in vitro method for determining the replicative capacity of two HIV viruses in an environment, said method comprising the steps of:

a) generating a tagged recombinant infectious virus comprising a tagged HIV DNA vector, and a first amplicon derived from a first target HIV virus; wherein the tagged HIV DNA vector is generated by introduction of one or more silent mutations in one of the HIV genes selected from gag, pol, env, tat, rev, nef, vif, vpr, and vpu; wherein the tagged HIV DNA vector has a deletion in its DNA sequence that corresponds at most with or overlaps with the flanking regions of the first amplicon derived from the first target HIV virus; wherein the one or more silent mutations are introduced in a gene not comprised by the first amplicon derived from the first target HIV virus; and wherein the first amplicon comprises the gag, pol, or env genes from the first target HIV virus, portions thereof, and combinations thereof;

b) generating a non-tagged recombinant infectious virus comprising a non-tagged HIV DNA vector, and a second amplicon derived from a second target HIV virus; wherein the non-tagged HIV DNA vector does not comprise the one or more silent mutations introduced in the tagged HIV DNA vector of step a); wherein the non-tagged HIV DNA vector has a deletion in its DNA sequence that corresponds at most with or overlaps with the flanking regions of the second amplicon derived from the second target HIV virus; and wherein the second amplicon comprises the gag, pol, or env genes from the second target HIV virus, portions thereof, and combinations thereof;

c) mixing the recombinant infectious viruses of steps a) and b) in a cell culture in a given environment; and d) determining by quantitative amplification the proportion of the tagged recombinant infectious virus and of the non-tagged recombinant infectious virus within the overall viral population, by detecting the one or more silent mutations in the HIV DNA vector portion of the tagged recombinant infectious virus, and by detecting the lack of the one or more silent mutations in the HIV DNA vector portion of the non-tagged recombinant infectious virus.

In particular, the first target virus may be a WT virus and the second target virus a mutant virus strain, or vice versa. Alternatively, the first target virus may be a mutant virus strain and the second target virus a different mutant virus strain.

In one embodiment, the present invention relates to the method mentioned supra, wherein the replicative capacity is determined for three or more target HIV viruses in an environment, said method comprising the steps of:

a) generating the tagged recombinant infectious virus of step a) of the method mentioned supra;

b) generating the non-tagged recombinant infectious virus of step b) of the method mentioned supra;

c) generating additional one or more tagged recombinant infectious virus, each comprising a tagged HIV DNA vector, and a third or subsequent amplicon derived from the additional one or more target HIV virus; wherein the tagged HIV DNA vector is generated by introduction of one or more silent mutations in one of the HIV genes selected from gag, pol, env, tat, rev, nef, vif, vpr, and vpu, said one or more silent mutations being different from the one or more silent mutations of the first tagged HIV DNA vector of step a) of this method; wherein each of the tagged HIV DNA vectors has a deletion in its DNA sequence that corresponds at most with or overlaps with the flanking regions of the third or subsequent amplicon derived from the third or subsequent target HIV virus; wherein the one or more silent mutations are introduced in a gene not comprised by the third or subsequent amplicon derived from the third or subsequent target HIV virus; and wherein the third or subsequent amplicon comprises the gag, pol, or env genes from the third or subsequent target HIV virus, portions thereof, and combinations thereof;

d) mixing the recombinant infectious viruses of step c) with the recombinant infectious viruses of steps a) and b) in a cell culture in a given environment; and e) determining by quantitative amplification the proportion of each of the tagged recombinant infectious virus and of the non-tagged recombinant infectious virus within the overall viral population, by detecting the one or more silent mutations in the HIV DNA vector portion of each of the tagged recombinant infectious virus, and by detecting the lack of the one or more silent mutations in the HIV DNA vector portion of the non-tagged recombinant infectious virus.

The present invention provides a recombinant virus marker virus system wherein each of the tagged HIV DNA vector and the non-tagged HIV DNA vector comprises the backbone of a wild-type or a mutant strain.

The recombinant virus marker virus system further provides proviral DNA, plasmid constructs, primers, and probes designed for the retrieval, preparation and analysis of several and diverse HIV genetic material. In one embodiment, the tagged HIV DNA vector or the non-tagged HIV DNA vector is a proviral HIV DNA or a plasmid DNA.

Because one or more of the vectors is tagged, the proportion of viruses in a mixed culture that carry each of the tagged sequence can easily be determined by quantifying the frequency of each of the tagged genes with quantitative amplification. Thus, the need to design unique primers for each allele is avoided. Moreover, using recombinant viruses as opposed to primary isolates eliminates possible effects of polymorphisms or mutations outside the coding region of interest on relative fitness. One of the main advantages of these recombinant clones is the flexibility for studying specific coding regions under selection by current protease and reverse transcriptase inhibitors in the same genetic background. In fact, using recombinant viruses, as opposed to HIV-1 primary isolates, it eliminates possible fitness effects of polymorphisms or mutations outside the targeted coding region. As such, a fully standardized protocol is obtained which can be applied to investigate the fitness of all kinds of HIV variants.

The methods for determining viral fitness may be useful for designing a treatment regimen. For example, a method may comprise determining the relative replicative capacity of a clinical isolate of a patient in the presence of one or more drugs and using said relative replicative capacity to determine an appropriate drug regimen for the patient.

The present invention also provides a method to aid scientists in studying the evolution of the different HIV strains in the presence or absence of environmental factors, such as and without being limited to, drug pressure, dilution factors, competitive binding proteins such as albumin, α1-glycoprotein, cell lines, etc.

In addition, the present invention provides the primers selected from SEQ ID NOs: 1-12, 19-20 and 24-25; HIV plasmid vectors comprising tagged or non-tagged sequences in the HIV genes and a deletion of the gag, pol, or env genes genetic sequences, portions thereof, and combinations thereof, wherein the tagged sequence comprises one or more silent mutations in one of the genes selected from gag, pol, env, tat, rev, nef, vif, vpr, and vpu. The invention further provides a kit for quantifying viral fitness of HIV viruses. Such a kit for determining the viral fitness of two or more HIV viruses in an environment comprises: i) one or more primers selected from SEQ ID NOs: 1-12, 19-20 and 24-25; and/or ii) one or more of the tagged HIV plasmid vectors and optionally a non-tagged HIV HXB2D plasmid vector; and iii) optionally probes for quantitative amplification, as described in the present invention. Such a kit may be further completed with at least one HIV inhibitor. Optionally, a reference proviral DNA or plasmid bearing a WT HIV sequence may be added. Optionally, cells susceptible to HIV infection may be added to the kit. In addition, other environmental factors may be added.

The determination by quantitative amplification of the proportion of the one or more tagged recombinant infectious virus and of the non-tagged recombinant infectious virus within the overall viral population is performed by in vitro amplification techniques including, but not limited to, polymerase chain reaction (PCR), strand displacement amplification (SDA), transcription-mediated amplification (TMA), nucleic acid sequence based amplification (NASBA), self-sustained sequence replication (3SR), transcription-based amplification (TAS), rolling circle amplification (RCA), loop-mediated isothermal amplification (LAMP) and ligase chain reaction (LCR) (reviewed Schweitzer, B. and Kingsmore, S., 2001, Combining nucleic acid amplification and detection. Current Opinion in Biotechnology, 12: 21-27). The accumulation of amplicons generated by in vitro amplification techniques can be monitored in real time using protocols which employ LUX™ fluorogenic primers, probes cleavable by DNAzymes, QZymes, or MNAzymes, TAQ-MAN® probes, molecular beacons, scorpions or any other FRET probes.

The present invention further provides a method wherein the quantitative amplification is performed by polymerase chain reaction employing the MNAzymes as monitoring technology.

Results from the viral fitness experiments can be used to develop a database of replicative capacity levels of specific amplicons in the presence or absence of particular environmental factors for a large number of WT and mutant HIV strains. The genotype or phenotype of a particular amplicon may be correlated to the replicative capacity of said particular amplicon in the presence of other viruses. Identical genotypes or phenotypes are retrieved and the database is further interrogated to identify if a corresponding viral fitness is known for any of the retrieved sequences. In this latter case a virtual viral fitness may be determined A report may be prepared including the viral fitness of the viral strain against one or more other strains, including WT, the genotype and/or phenotype of the strain under investigation, and other information such as environmental factors tested, biological cut-offs, etc. Such a database may be analyzed in combination with gag, pol, or env genetic sequence information and the results used in the determination of appropriate treatment strategies.

DESCRIPTION OF THE INVENTION

Definitions

Figure 1:
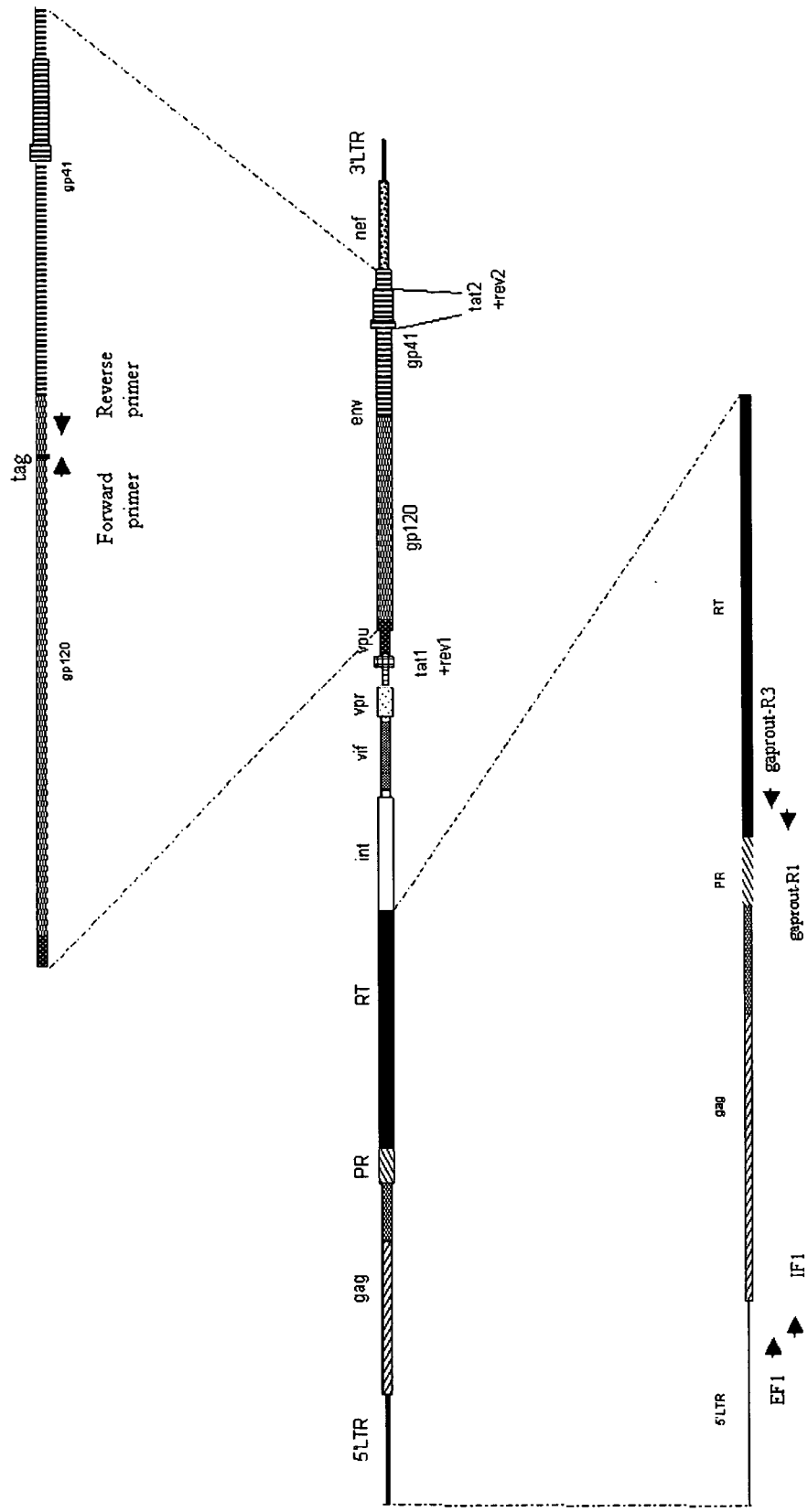
FIG. 1, in the central part, is a schematic representation of the complete HIV genome. In the upper part, the envelope gene is highlighted indicating the position of the tag and the position where the primers bind for detecting the tag. In the lower part there is a schematic overview of the position where the primers bind for amplifying the gag-protease amplicon which later can be recombined with the appropriate tagged or non-tagged plasmid vector.
Figure 2:
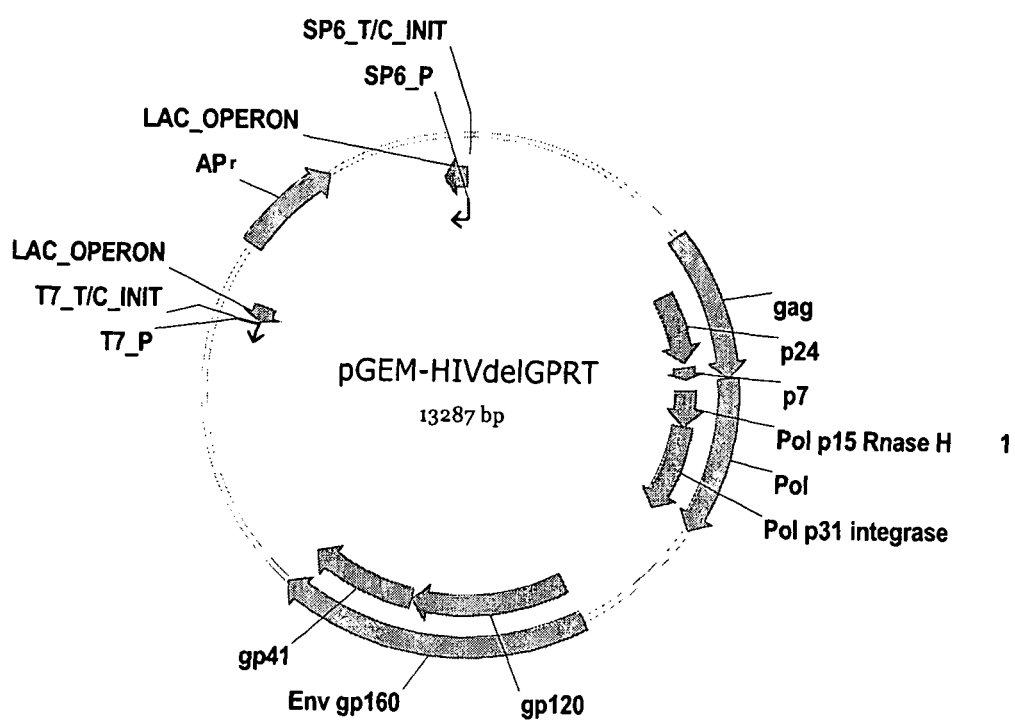
FIG. 2 shows a map of the pGEM vector pGEM-HIVdel-GPRT (accession nr LMBP4568, deposited at the Belgian Coordinated Collections of Micro-Organisms located at the Universiteit Gent—Laboratorium voor Moleculaire Biologie on Jul. 1, 2002) wherein the subcloned HIV genes are identified. Said vector has a deletion of the gag-protease-reverse transcriptase encoding sequences.
Figure 3:
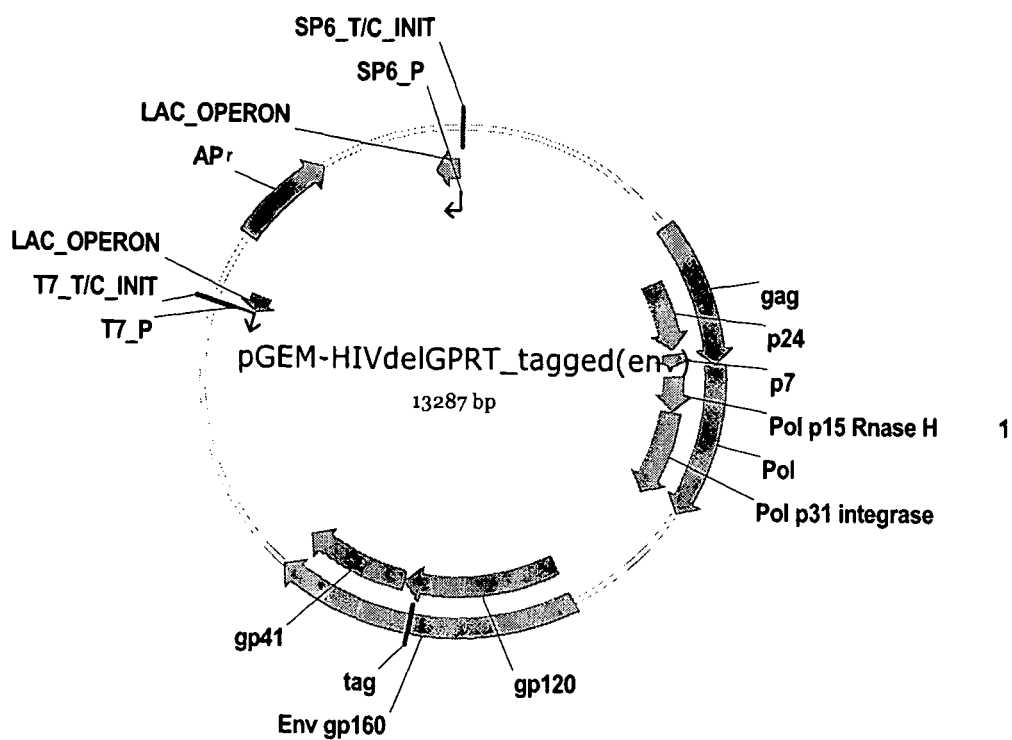
FIG. 3 shows a map of the pGEM vector (pGEM-HIVdel-GPRT_tagged(env)) (accession nr LMBP 5112, deposited at the Belgian Coordinated Collections of Micro-Organisms located at the Universiteit Gent—Plasmidecollectie vakgroep moleculaire biologie on Dec. $20^{th}$, 2005) wherein the subcloned HIV genes are identified. Said vector has a deletion of the gag-protease-reverse transcriptase encoding sequences, and further comprises a tagged envelope gene.
Figure 4:
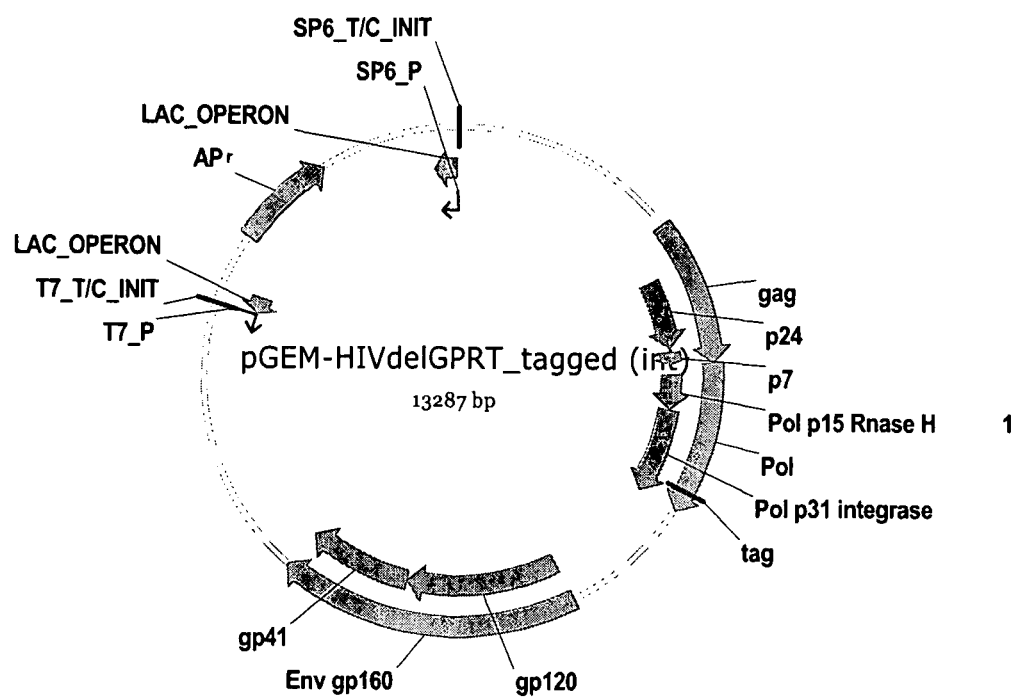
FIG. 4 shows a map of the pGEM vector (pGEM-HIVdel-GPRT_tagged(int)) (accession nr LMBP 5113, deposited at the Belgian Coordinated Collections of Micro-Organisms located at the Universiteit Gent—Plasmidecollectie vakgroep moleculaire biologie on Dec. $20^{th}$, 2005) wherein the subcloned HIV genes are identified. Said vector has a deletion of the gag-protease-reverse transcriptase encoding sequences, and further comprises a tagged integrase sequence.

By the term "viral fitness" is meant the replicative capacity of any HIV-1 variant in a given environment, e.g. a cell system in the presence or absence of a drug.

The term "tag" refers to a chemical moiety, either a nucleotide, oligonucleotide, or polynucleotide that, when substituted or added to another sequence, provides additional utility or confers useful properties to that sequence, particularly in the detection or isolation thereof. In particular in the present invention, the term "tag" refers to one or more nucleotides that are substituted in an HIV DNA vector by other one or more nucleotides with the peculiarity that these substitutions of nucleotides are all silent mutations which do not disrupt the reading frame of the HIV DNA. In the present invention, the one or more silent mutations are introduced into the HIV DNA vector, in particular in one of the HIV genes selected from gag, pol, env, tat, rev, nef, vif, vpr, and vpu, thereby generating a "tagged HIV DNA vector".

The "non-tagged HIV DNA vector" refers to the vector which does not comprise the one or more silent mutations introduced in the tagged HIV DNA vector.

An "amplicon" is defined as any nucleic acid molecule produced by an ex vivo or in vitro nucleic acid amplification technique. In particular, an amplicon comprises a sequence that hybridizes with a primer when contacted therewith, and that can be either an entire molecule or a portion thereof.

The amplicon derived from the target HIV virus refers to the nucleic acid sequence of the HIV target virus of interest whose replicative capacity is to be determined by the instant invention. In particular, the amplicon derived from the target HIV virus comprises one of the HIV genes or portions thereof, and combinations thereof, which are selected from the gag, pol, and env genes, i.e. the gag gene, the protease encoding region of the pol gene, the reverse transcriptase encoding region of the pol gene, the integrase encoding region of the pol gene, the env gene, portions thereof, and combinations thereof. In particular, the amplicon derived from the target HIV virus is selected from gag-PR-RT-int, gag-PR-RT, gag-PR, gag, PR-RT-int, RT-int, int, PR-RT, PR, RT, env, and portions thereof. Additionally, the amplicon may include flanking regions, for example for the gag-PR and PR-RT genes, those flanking regions with 5'LTR sequences, or portions thereof. It should be understood that this amplicon may be of diverse origin, including plasmids, patient derived material, or laboratory viruses including IIIB and NL4-3, or any other mutant or WT viruses.

The amplicon derived from the target HIV virus is not to be confused with the sequence which is amplified during quantitative amplification. This last sequence or amplicon corresponds to the tagged or non-tagged region of the tagged HIV DNA vector or non-tagged HIV DNA vector, respectively. These tagged HIV DNA vector or non-tagged HIV DNA vector are ultimately recombined with the amplicon derived from the target HIV virus, and the sequence that is quantitatively amplified originates from the recombinant viruses. In particular, the amplicon that is quantitatively amplified comprises or lacks the one or more silent mutations introduced in one of the HIV genes selected from gag, pol, env, tat, rev, nef, vif, vpr, and vpu.

"Primer" shall mean a short segment of DNA or DNA-containing nucleic acid molecule, which (i) anneals under amplification conditions to a suitable portion of a DNA or RNA sequence to be amplified, and (ii) initiates, and is itself physically extended, via polymerase-mediated synthesis.

"Amplification" of a target nucleic acid sequence shall mean an in vitro target amplification technique whereby target sequences are copied, producing amplicons which serve as templates for further cycles of amplification. Such in vitro amplification techniques include, but are not limited to, polymerase chain reaction (PCR), strand displacement amplification (SDA), transcription-mediated amplification (TMA), nucleic acid sequence based amplification (NASBA), self-sustained sequence replication (3SR), transcription-based amplification (TAS), rolling circle amplification (RCA), loop-mediated isothermal amplification (LAMP) and ligase chain reaction (LCR).

By "environment" is meant drug pressure such as antiviral drugs, antibiotics, or any other drug, competitive binding proteins such as albumin, α1-glycoprotein, toxins, specific types of medium, serum, and components thereof, dilution factors, cell lines, temperature, pressure, radiation, etc.

Treatment or treatment regimen refers to the management or handling of an individual medical condition by the administration of drugs, at directed dosages, time intervals, duration, alone or in different combinations, via different administration routes, in suitable formulations, etc.

By "drug" is meant any agent such as a chemotherapeutic, peptide, antibody, antisense, ribozyme and any combination thereof, be it marketed or under development. Examples of anti-HIV drugs that can be tested in the assay of the present invention include all approved and under development, nucleotide, nucleoside, and non-nucleoside RT inhibitors, PR inhibitors, entry inhibitors, envelope inhibitors and integrase inhibitors. HIV inhibitors comprise nucleoside reverse transcriptase inhibitors (NRTIs), nucleotide reverse transcriptase inhibitors (NtRTIs), non-nucleoside reverse transcriptase inhibitors (NNRTIs), protease inhibitors (PIs), entry inhibitors, fusion inhibitors, gp41 inhibitors, gp120 inhibitors, integrase inhibitors, co-receptors inhibitors (e.g. CCR5, CXCR4, . . . ), budding/maturation inhibitors, etc.

HIV nucleoside RT inhibitors include those compounds whose mechanism of action comprises an inhibition of the viral RT enzyme. As example, and with no limitation to existing and future new compounds, HIV nucleoside reverse transcriptase inhibitors include zidovudine (AZT), lamivudine (3TC), stavudine (d4T), zalcitabine (ddC), didanosine (ddI), abacavir (ABC)

HIV non-nucleoside reverse transcriptase inhibitors include those compounds whose mechanism of action comprises an inhibition of the viral reverse transcriptase enzyme. As example, and with no limitation to existing and future new compounds, HIV non-nucleoside reverse transcriptase inhibitors include nevirapine, delavirdine, efavirenz, TMC120, TMC125, capravirine, calanolide, UC781, SJ-1366, benzophenones, PETT compounds, TSAO compounds.

HIV nucleotide reverse transcriptase inhibitors include those compounds whose mechanism of action comprises an inhibition of the viral reverse transcriptase enzyme. As example, and with no limitation to existing and future new compounds, HIV non-nucleotide reverse transcriptase inhibitors include adefovir (PMEA), tenofovir (PMPA), and other phosphonates.

HIV protease inhibitors include those compounds whose mechanism of action comprises an inhibition of the viral protease enzyme. As example, and with no limitation to existing and future new compounds, HIV protease inhibitors include ritonavir (RTV), indinavir (IDV), nelfinavir (NFV), amprenavir (APV), telinavir (SC-52151), tipranavir (TPV), saquinavir (SQV), lopinavir (LPV), atazanavir, palinavir, mozenavir, BMS 186316, DPC 681, DPC 684, AG1776, GS3333, KNI-413, KNI-272, L754394, L756425, LG-71350, PD161374, PD173606, PD177298, PD178390, PD178392, PNU 140135, maslinic acid, U-140690, RO033-4649, TMC114, TMC126, their prodrugs, metabolites, N-oxides and salts.

HIV entry inhibitors or gp120 inhibitors include those compounds whose mechanism of action comprises an inhibition of the viral entry or gp120 glycoprotein. As example, and with no limitation to existing and future new compounds, HIV entry or gp120 inhibitors include BMS806, dextran sulfate, suramin, chicoric acid.

HIV fusion inhibitors or gp41 inhibitors include those compounds whose mechanism of action comprises an inhibition of the viral fusion or gp41 glycoprotein. As example, and with no limitation to existing and future new compounds, HIV fusion or gp41 inhibitors include T20, T1249.

HIV integrase inhibitors include those compounds whose mechanism of action comprises an inhibition of the viral integrase enzyme. As example, and with no limitation to existing and future new compounds, HIV integrase inhibitors include L-870810, L-870812, pyranodipyrimydines, S-1360.

Co-receptors inhibitors include those compounds whose mechanism of action comprises an inhibition of the interaction of HIV with cellular receptors present on the cell membrane (e.g. CCR5, CXCR4). As example, and with no limitation to existing and future new compounds, co-receptors inhibitors include TAK 779, AMD3100, AMD8664, AMD070, SHC-C, SHC-D, AK602, TAK-220, UK-427,857, T22.

HIV budding/maturation inhibitors include those compounds whose mechanism of action comprises an inhibition of the viral budding/maturation. As example, and with no limitation to existing and future new compounds, HIV budding/maturation inhibitors include PA-457.

The term "chimeric" means a construct comprising nucleic acid material from different origin such as, for example, a combination of WT virus with a laboratory strain, a combination of WT sequences and subject-derived clinical isolate sequences.

Viruses

A human immunodeficiency virus (HIV), as used herein refers to any HIV including laboratory strains, wild type strains, mutant strains and any biological sample comprising at least one HIV virus, such as, for example, an HIV clinical isolate. HIV strains compatible with the present invention are any such strains that are capable of infecting mammals, particularly humans. Examples are HIV-1, HIV-2, and SIV.

For reduction to practice of the present invention, an HIV virus refers to any sample comprising at least one HIV virus. A sample may be obtained for example from an individual, from cell cultures, or generated using recombinant technology, or cloning.

HIV strains compatible with the present invention are any such strains that are capable of infecting cell lines and humans. Viral strains used for obtaining a plasmid are preferably HIV wild-type sequences, such as LAI, HXB2D for HIV subtye B studies. LAI, also known as IIIB, is a wild-type HIV strain. One particular clone thereof, this means one sequence, is HXB2D. This HXB2D sequence may be incorporated into a plasmid. Other clones of HIV from other subtypes or groups may also be used.

Instead of viral RNA, HIV DNA, e.g. proviral DNA, may be used for the methods described herein. In case RNA is used, reverse transcription into cDNA by a suitable reverse transcriptase is needed. The protocols describing the analysis of RNA are also amenable for DNA analysis. However, if a protocol starts from DNA, the person skilled in the art will know that no reverse transcription is needed. The primers designed to amplify the RNA strand, also anneal to, and amplify DNA. Reverse transcription and amplification may be performed with a single set of primers. Suitably a hemi-nested and more suitably a nested approach may also be used to reverse transcribe and amplify the genetic material.

Amplicons Derived from the Target HIV Virus

The amplicons derived from the target HIV virus may be obtained from HIV-1 clinical isolates, site directed mutants or viruses emerging from selection experiments. Any type of patient sample may be used to obtain the desired amplicons, such as, for example, serum, blood, and tissue.

Viral RNA may be isolated using known methods such as that described in Boom, R. et al. (J. Clin. Microbiol. 28(3): 495-503 (1990); incorporated herein by reference), or through other conventional methods such as the acid phenol method (e.g., the acid guanidinum-phenol-chloroform (AGPC) method), the guanidinium isothiocyanate procedure, thus employing the method of Chomczynski and Sacchi (*Anal. Biochem.* 162, 156-159 (1987)). Alternatively, a number of commercial methods such as the QIAAMP® viral RNA kit (Qiagen, Inc.) may be used to obtain viral RNA from bodily fluids such as plasma, serum, or cell-free fluids. Viral RNA may also be isolated from a pelleted virus using TRI-ZOL® (Gibco) as described by the manufacturer. Other commercial kits for the isolation of viral RNA include, without being limited to, QIAGEN® RNEASY® Kit, CATRIMOX 14® RNA Isolation Kit Ver.2.11 (TaKaRa), RNAAGENTS® Total RNA Isolation System (Promega), RNAZOL®, Tel-Test, STRATAGENE®, TRI-REAGENTS BD™ (Sigma), PURESCRIPTT™ Total RNA Isolation Kit (Gentra Systems, or Qiagen).

DNA may be extracted from tissue using methods known by the skilled in the art such as the procedure described by Maniatis et al. (1982) which involves the preparation of a cell lysate followed by digestion with proteinase K, obtaining DNA purification by a multi-step phenol extraction, ethanol precipitation and ribonuclease digestion. Optionally, available commercial methods may also be employed to obtain DNA from bodily fluids, such as QIAAMP® Blood kits for DNA isolation from blood and body fluids (Qiagen, Inc.).

Complementary DNA may be synthetised with SENSIS-CRIPT® RT (Qiagen). Nucleic acid may be amplified by techniques such as polymerase chain reaction (PCR), strand displacement amplification (SDA), rolling circle amplification (RCA), loop-mediated isothermal amplification (LAMP), transcription-mediated amplification (TMA), nucleic acid sequence based amplification (NASBA), self-sustained sequence replication (3SR), transcription-based amplification (TAS), and ligase chain reaction (LCR).

HIV DNA Vectors

The invention relates to tagged and non-tagged HIV DNA vectors. This viral DNA may be a proviral DNA, i.e. a pseudotype virus which is replication-competent, or other types of vectors such as plasmids. In particular, the proviral DNA and vectors or plasmids have a deletion in their DNA sequence that corresponds at most with or overlaps with the flanking regions of the amplicon derived from the target HIV virus referred above.

In one embodiment, the present invention relates to tagged and non-tagged plasmids and to the use of said plasmids in the methods disclosed herein. The complete HIV sequence may be incorporated in the plasmid or only part(s) thereof, such as, for example, the plasmids used in the present invention lack the gag, pol, and env genes, portions thereof, and combinations thereof. The deletion may also comprise parts of flanking genes, or eventually more than one gene. A suitable plasmid backbone may be selected from the group including pUC, pBR322 and pGEM.

In one embodiment, each of the tagged HIV DNA vector and the non-tagged HIV DNA vector comprises the backbone of a wild-type or a mutant strain.

In one embodiment, the plasmid DNA encompassed by the tagged and non-tagged HIV DNA vectors comprises the genome of the HXB2D wild-type strain.

A deletion construct containing the DNA of the present invention can be prepared, for example, by treating a longer DNA with appropriate restriction enzymes and purifying the digest with an appropriate purification method and then subjecting the thus obtained DNA fragment of interest to self-ligation. As such, the construction of the deletion constructs of the present invention may be accomplished by digestion with restriction enzymes, such as ClaI and BclI restriction enzymes, which cleave the plasmid backbone at specific sites and therefore remove the gag and protease sequences. Alternatively, before removal of the gag and protease sequences, a MunI or NheI site may be inserted into the plasmid by silent mutation, prior to digestion with MunI/BssH II or NheI/BclI, respectively, and subsequent removal of gag and protease sequences.

Unique restriction site refers to a single occurrence of a site on the nucleic acid that is recognized by a restriction enzyme, or that it does not occur anywhere else in the construct. The unique restriction site may be created after amplification by re-ligating both 5' and 3' ends of the amplified plasmid's DNA. Alternatively, the unique restriction site may not have to be created, as it may be already fully located in one of the ends, 5' or 3' end. Optionally, the unique restriction site may be inserted. Optionally, part of the unique restriction site may be present in the region to be amplified. The creation of a unique restriction site deriving from amplification is a preferred method since this is a one-step, direct, simple and fast method. The unique restriction site is further relevant for the production of recombinant virus.

As one skilled in the art will understand, the creation of a unique restriction site will depend upon the sequence of the HIV genome, and upon the sequence to be deleted therefrom. Unique restriction sites that can be employed in the present invention are those present only once in the HIV genome and may flank the region of interest to be deleted and that do not change the reading frame or the sequence of the protein coded by the nucleic acid sequence of interest. Optionally, the primers used for amplification may contain the same or other specific restriction endonuclease sites to facilitate insertion into a different vector. Additionally, one of the primers used for amplification may contain a phosphorylated 5' end-linker to facilitate insertion of a foreign amplicon.

Optionally, the method for obtaining a plasmid containing the WT HIV sequence with a deletion in the region that corresponds at most with or overlaps with the flanking regions of the amplicon to be recombined with, may be performed in a second cloning vector. For instance, the protease-reverse transcriptase region may be inserted into a cloning vector such as pGEM plasmid, for example the backbone of pGEM3 vector may be used, and manipulated, by amplification, to remove part of the protease and/or reverse transcriptase-coding region such that insertion of the remaining protease-reverse transcriptase sequence from the samples is performed in a way that would not disrupt the reading frame. The manipulated protease-reverse transcriptase region is then placed in a pGEM-HXB2D vector such that it contains the complete wild type HIV sequence except for the relevant protease-reverse transcriptase deletion.

An example of a protease-reverse transcriptase deletion vector is pGEM-HXB2DAPR-RT, which has a deletion comprising the entire protease coding region and a large portion of the reverse transcriptase coding region. An example of a reverse transcriptase deletion vector is pGEM-HXB2DART, which has a deletion of the reverse transcriptase coding region.

Those of skill in the art will appreciate that other HIV vectors and cloning procedures known in the art may also be used to create deficient gag-PR-RT-int, gag-PR-RT, gag-PR, gag, PR-RT-int, RT-int, int, PR-RT, PR, RT, or env plasmids for recombination or ligation with subject derived sequences and creation of infectious viruses. For instance, deletion constructs may be prepared by re-introducing portions of the gag-PR-RT-int, gag-PR-RT, gag-PR, gag, PR-RT-int, RT-int, int, PR-RT, PR, RT, or env genes into a plasmid wherein the gag-PR-RT-int, gag-PR-RT, gag-PR, gag, PR-RT-int, RT-int, int, PR-RT, PR, RT, or env genes, respectively, have been previously deleted. Primers for amplifying the regions of interest, i.e. the portions to be re-introduced, are known to the skilled in the art. In general, vectors must be created to allow re-insertion of the deleted sequences without disrupting the reading frame of the gag-PR-RT-int, gag-PR-RT, gag-PR, gag, PR-RT-int, RT-int, int, PR-RT, PR, RT, and env genes.

The tagged HIV DNA vector may be obtained by introduction of one or more silent mutations into the plasmid constructs discussed above. Introduction of the silent mutations will be applied on those genes forming part of the plasmid, i.e. those genes which are not forming part of the amplicon derived from the target HIV virus. The one or more silent mutations may be incorporated in any of the HIV genes of the plasmid provided that the phenotype of the resulting recombinant virus remains unchanged.

In one embodiment, introduction of one or more silent mutations is performed in one of the HIV genes selected from gag, pol, env, tat, rev, nef, vif, vpr, and vpu. In another embodiment, introduction of the silent mutations is performed in the env or pol genes, in particular in the env region encoding the envelope protein, or in the pol region encoding the integrase enzyme. In another embodiment, introduction of silent mutations is performed in the env gene, between codons 1 and 857, in particular between codons 100 and 800, more in particular between codons 200 and 600, yet more in particular between codons 300 and 500, for example between codons 400 and 500, for example between codons 430 and 490, particularly between codons 468 and 475.

In another embodiment, introduction of silent mutations is performed in the region of the pol gene encoding the integrase enzyme, between codons 1 and 288, in particular between codons 50 and 275, more in particular between codons 100 and 250, yet more in particular between codons 150 and 250, for example between codons 200 and 250, particularly between codons 230 and 231.

This introduction of silent mutations may be accomplished by using the QUICKCHANGE™ site-directed mutagenesis kit (Stratagene) and suitable mutagenic oligonucleotide primers for the region of interest. Site-directed mutagenesis allows the generation of point mutations, the switching of nucleotides and deletion or insertion of single or multiple nucleotides, possibly with changes on the amino-acid level. For the scope of the present invention, site-directed mutagenesis is applied to insert silent mutations in the gene of interest. The basic procedure uses plasmid DNA and two oligonucleotide primers which are complementary to opposite strands of the plasmid and contain the desired mutation(s). These primers are extended during polymerase chain reaction (PCR) which is followed by a digestion with the restriction enzyme DpnI, which is a specific endonuclease for methylated and hemimethylated DNA. During this digest the parental plasmid will be removed. The newly created plasmid with the desired mutation(s) can be used for transformation in $E.$ $coli.$ In particular, suitable mutagenic oligonucleotide primers are the primers described herein below and their homologues, which are herein claimed. Primers with SEQ ID NOs: 1-2 are useful for the incorporation of silent mutations in the integrase encoding region of the pol gene and SEQ ID NOs: 3-4 are useful for the incorporation of silent mutations in the envelope gene of an HIV derived plasmid.

TABLE 1 mutagenic oligonucleotide primers

| SEQ ID NO: | Primer sequence listed in 5' to 3' direction | |
|---|---|---|
| 1 (forward) | TCGGGTTTAT TACAGGGACt cacG-tAATCC ACTTTGGAAA GGACCAGC | SDM050012_F |
| 2 (reverse) | GCTGGTCCTT TCCAAAGTGG ATTaCgt-gaG TCCCTGTAAT AAACCCGA | SDM050012_R |
| 3 (forward) | CCGAGATCTT CAGGCCCGGA GGAGGTGACA TGAGGGACAA TTG | SDMtagged_F |
| 4 (reverse) | CAATTGTCCC TCATGTCACC TCCTCCGGGC CTGAAGATCT CGG | SDMtagged_R |

Such primers are chosen from SEQ ID NOs: 1-4 or have at least 80% homology, preferably 90% homology, more preferably 95% homology as determined using algorithms known to the person skilled in the art such as FASTA and BLAST. The primer sequences listed herein may optionally be labeled. Suitably, this label may be detected using fluorescence, luminescence or absorbance. In addition primers located in a region of 50 nucleotides (nt) upstream or downstream from the sequences given herein constitute part of the present invention. Specifically, the primers may be located in a region of 20 nt upstream or downstream from the sequences given herein and, constitute, as well, part of the present invention. Also, primers comprising at least 8 consecutive bases present in either of the primers described herein constitute an embodiment of the invention. Interestingly, the primers comprise at least 12 consecutive bases present in either of the primers described herein. In one aspect of the present invention the primers may contain linker regions for cloning. Optionally, the linker region of a primer may contain a restriction enzyme recognition site. Preferably, said restriction enzyme recognition site is a unique restriction enzyme recognition site. Alternatively, primers may partially anneal to the target region.

The presence of mutant sequences may be confirmed by DNA sequencing of the final plasmid clone.

The present invention provides HIV plasmid vectors comprising a tagged sequence; and a deletion of the gag, pol, or env genetic sequences, portions thereof, and combinations thereof; characterized in that the tagged sequence comprises one or more silent mutations in one of the genes selected from gag, pol, env, tat, rev, nef, vif, vpr, and vpu; and with the proviso that the one or more silent mutations are not located in the deleted genetic sequence. The present invention further provides HIV plasmid vectors comprising a deletion of the gag, pol, or env genetic sequences, portions thereof, and combinations thereof; and no tagged sequence. Suitably, the HIV plasmid vector is derived from the HIV wild-type strain HXB2D (Ratner et al. (1987) *AIDS Res. Hum. Retrovir.* 3:57-69]). Suitably, the tagged sequence is located in one or more of the genes selected from gag, pol, env, tat, rev, nef, vif, vpr, and vpu, preferably in the env or pol genes, more preferably in the env region encoding the envelope protein, or in the pol region encoding the integrase enzyme.

In one embodiment of the present invention, the tagged HIV plasmid vector comprises a tagged sequence in the env gene between codons 1 and 857, in particular between codons 100 and 800, more in particular between codons 200 and 600, yet more in particular between codons 300 and 500, for example between codons 400 and 500, for example between codons 430 and 490, particularly between codons 468 and 475. These HIV plasmid vectors comprising a tagged sequence in the env gene are claimed.

In another embodiment of the present invention, the tagged HIV plasmid vector comprises a tagged sequence in the region of the pol gene encoding the integrase enzyme between codons 1 and 288, in particular between codons 50 and 275, more in particular between codons 100 and 250, yet more in particular between codons 150 and 250, for example between codons 200 and 250, particularly between codons 230 and 231. These HIV plasmid vectors comprising a tagged sequence in the integrase encoding region of the pol gene are claimed.

In particular, the present invention provides the tagged HIV DNA vectors pGEM-HIVdelGPRT_tagged(env) (accession number LMBP 5112, SEQ ID NO: 28), and pGEM-HIVdel-GPRT_tagged(int) (accession number LMBP 5113, SEQ ID NO: 29), which have been deposited at the Belgian Coordinated Collections of Micro-Organisms located at the Universiteit Gent—Plasmidecollectie vakgroep moleculaire biologie on Dec. $20^{th}$, 2005.

Generation of Tagged and Non-Tagged Recombinant Infectious Viruses

Recombinant tagged and non-tagged infectious viruses may be generated by transfection of each of the tagged or non-tagged HIV DNA vectors together with the coding fragments of interest, i.e. the amplicons derived from the target HIV virus, into cells followed by passage of cell-free viral supernatants in cells. Transfection may be achieved by electroporation, ligation, lipofection or any other method.

To prepare recombinant HIV viruses, the amplified sequences of gag-PR-RT-int, gag-PR-RT, gag-PR, gag, PR-RT-int, RT-int, int, PR-RT, PR, RT, env, or portions thereof, are incorporated into a tagged or non-tagged HIV DNA vector comprising the HIV wild-type or a mutant strain thereof with a deletion of the portion corresponding at most to the amplicon. An infectious clone is generated upon exchange of genetic material between the amplicon and the deletion construct to yield an HIV sequence.

The amplicons derived from the target HIV virus may be incorporated into the appropriate HIV DNA vector by homologous recombination in a suitable host cell between overlapping DNA segments of the vector and the amplicon sequence. Alternatively, the amplicons derived from the target HIV virus can be incorporated into the vector at a unique restriction site according to cloning procedures standard in the art. The latter is a direct cloning strategy. Suitable for direct cloning strategies are two different restriction sites that are used to facilitate ligation of the amplicon in the appropriate orientation.

Recombinant virus stocks may be stored for future analysis, such as for example, viability testing.

Cell Culture

The cells may be chosen from T cells, monocytes, macrophages, dendritic cells, Langerhans cells, hematopoietic stem cells, peripheral blood mononuclear cells (PBMC) or, precursor cells, human T-lymphoblastoid cell lines, MT4, MT2, CEM, and PM-1 cells. Suitable host cells for homologous recombination of HIV sequences include MT4 and PM-1. MT4 is a $CD4^+$ T-cell line containing the CXCR4 co-receptor. The PM-1 cell line expresses both the CXCR4 and CCR5 co-receptors. All the above mentioned cells are capable of producing new infectious virus particles upon recombination of the HIV DNA vectors with the amplicons derived from the target HIV virus.

In a cell culture, the cells are usually maintained in a protein-rich medium, such as RPMI1640 supplemented with fetal calf serum at 10%, L-glutamine (2 mM), and antibiotics such as penicillin, and streptomycin. Interestingly, prior to HIV infection, PBMC cells may be stimulated with phytohemagglutinin for some days and maintained in R-20 medium (RPMI 1640 supplemented with fetal calf serum 20%), L-glutamine, HEPES buffer, recombinant human interleukin-2; penicillin, and streptomycin.

Growth Competition Assay

Recombinant tagged and non-tagged viruses are then mixed together at different ratios, such as 0/100, 25/75, 50/50, 75/25, 100/0. Other ratios may be 0/100, 20/80, 40/60, 60/40, 80/20, 100/0. If more than two virus are tested, for example three, the ratios may be for instance 0/0/100, 0/33/66, 33/66/0. The mixed viral sample is used to infect cells suspended in the absence or presence of antiviral drugs or any other environmental components, as described herein. Thus cells usually suspended in medium are inoculated with infectious doses of the recombinant tagged and/or non-tagged viruses. The viral titer is determined (expressed as multiplicity of infection, MOI) and adapted to a suitable range, preferably between 0.0001 and 0.01, more preferably around 0.001 infectious viral units/cell.

In one embodiment of the present invention the tagged recombinant infectious virus comprising a tagged HIV DNA vector and a first target amplicon derived from a first target HIV virus, is mixed with a non-tagged recombinant infectious virus comprising a non-tagged HIV DNA vector and a second target amplicon derived from a second target HIV virus. These virus are mixed in a cell culture in a given environment, and the replicative capacities of the tagged and non-tagged recombinant viruses in said environment are determined by quantitative amplification.

Cells are incubated, washed, resuspended, reincubated, all the foregoing as needed. Supernatants are harvested at different time points, for example on days 1, 4, 7, 10, and 14. Starting from a certain day, for instance the fourth day after initial incubation, cultures are passaged and after incubation, washing, resuspension, and reincubation, viral RNA is extracted from culture supernatants at specific time points, e.g. on days 1, 4, 7, 10, 14, or any other day. Viral RNA extraction may be accomplished according to several techniques known in the art, for example by using the QIAGEN® RNA kit.

Alternatively, cells are grown with the recombinant infectious viruses and at specific time points, cells are collected and genomic DNA extraction is performed. Genomic DNA extraction may be accomplished according to several techniques known in the art, for example by using the kit INVISORB® DNA cell HTS 96 kit/V for purification of genomic DNA from INVITEK®.

The proportion of tagged recombinant virus versus non-tagged recombinant virus in the population is determined by quantitative amplification.

Quantitative Amplification

Quantitative amplification provides the data required for the direct quantification of the virus whose replicative capacity is to be determined. During quantitative amplification, the tagged and corresponding non-tagged regions of the recombinant virus extracted from the cell cultures or supernatants as described above, are amplified and detected, usually simultaneously. Optionally, a house-keeping gene may be used as an internal control.

The results can be expressed in absolute terms by reference to external quantified standards, i.e. in number of proviral DNA copies/amount of cells, or in relative terms compared to an overall viral population or another HIV virus present within the sample.

Techniques for the amplification of nucleic acid sequences are known in the art. These include techniques mediated by a DNA polymerase, such as the polymerase chain reaction ("PCR") (see, for example, U.S. Pat. No. 4,683,202; U.S. Pat. No. 4,683,195; U.S. Pat. No. 4,000,159; U.S. Pat. No. 4,965,188; U.S. Pat. No. 5,176,995) (Saiki et al., 1985; Chehab et al., 1987), strand displacement amplification ("SDA") (Walker et al., 1992), rolling circle amplification ("RCA") (Lizardi et al., 1998), reverse transcription polymerase chain reaction (RT-PCR) and loop-mediated isothermal amplification ("LAMP") (Notomi et al., 2000; Nagamine et al., 2002). Other target amplification techniques are mediated by an RNA polymerase, for example, transcription-mediated amplification ("TMA") (Jonas et al., 1993), self-sustained sequence replication ("3SR") (Fahy et al., 1991) and nucleic acid sequence replication based amplification ("NASBA") (Compton, 1991). The amplification products ("amplicons") produced by PCR, RT-PCR, SDA, RCA and LAMP are composed of DNA, whereas RNA amplicons are produced by TMA, 3SR and NASBA.

One known quantitative amplification technique is real time PCR. The polymerase chain reaction (PCR) is described in patents nos. U.S. Pat. No. 4,683,195 and U.S. Pat. No. 4,683,202.

The term "real time PCR" as used herein means that a signal emitted from the PCR assay is monitored during the reaction as an indicator of amplicon production during each PCR amplification cycle, i.e. in "real time", as opposed to conventional PCR methods, in which an assay signal is detected at the endpoint of the PCR reaction. Real time PCR is generally based on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehee et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

In one embodiment of the present invention, the sequence of the HIV tagged recombinant virus that is quantitatively amplified comprises one or more silent mutations in one of the HIV genes selected from gag, pol, env, tat, rev, nef, vif, vpr, and vpu. In one embodiment of the present invention, the sequence of the HIV non-tagged recombinant virus that is quantitatively amplified does not comprise the one or more silent mutations of the HIV tagged recombinant virus referred in the sentence above, i.e. it lacks all of the one or more silent mutations of the HIV genes selected from gag, pol, env, tat, rev, nef, vif, vpr, and vpu.

In another embodiment of the present invention, the sequence of the HIV tagged recombinant virus that is quantitatively amplified comprises one or more silent mutations in the env gene or in the integrase encoding region of the pol gene. In another embodiment of the present invention, the sequence of the HIV non-tagged recombinant virus that is quantitatively amplified does not comprise the one or more silent mutations of the HIV tagged recombinant virus referred in the sentence above, i.e. it lacks all of the one or more silent mutations in the env gene or in the integrase encoding region of the pol gene.

In one embodiment, the forward and reverse primers specific for quantitative amplification of tagged and non-tagged recombinant infectious virus include SEQ ID NOs: 5-12. SEQ ID NO: 5 is the forward primer which extends the tagged envelope gene, i.e. the envelope gene comprising one or more silent mutations. SEQ ID NO: 6 is the reverse primer which extends both the tagged envelope gene, and WT envelope gene. SEQ ID NO: 7 is the forward primer which extends the WT envelope gene. SEQ ID NOs: 8-9 are the forward and reverse primers which extend the housekeeping or control gene. SEQ ID NO: 10 is the forward primer which extends both the tagged integrase encoding sequence, i.e. the integrase encoding sequence comprising one or more silent mutations, and WT integrase encoding sequence. SEQ ID NO: 11 is the reverse primer which extends the tagged integrase encoding sequence. SEQ ID NO: 12 is the reverse primer which extends the WT integrase encoding sequence.

Additional sequences may be appended to the forward primers to allow real time PCR monitoring. Such sequences can include, but are not limited to, fluorogenic probes for LUX™ detection, anti-sense DNAzyme sequences for zymogene detection, and Scorpion probe sequences. Optionally, the appended sequences for real time monitoring may be attached to the reverse primers.

TABLE 2 primers specific for quantitative amplification of tagged and non-tagged recombinant infectious virus

| SEQ ID NO: | Primer sequence listed in 5' to 3' direction | useful for amplifying | name |
| --- | --- | --- | --- |
| 5 (forward) | ATGTCACCTCCTCCGGGC | tagged env gene | F8D |
| 6 (reverse) | CAGGAATGCTTGCTGCTG | tagged & WT env gene | R1 |

TABLE 2-continued primers specific for quantitative amplification of tagged and non-tagged recombinant infectious virus

| SEQ ID NO: | Primer sequence listed in 5' to 3' direction | useful for amplifying | name |
|---|---|---|---|
| 7 (forward) | ATATCTCCTCCTCCAGGT | WT env gene | F6B |
| 8 (forward) | ACAGGCAACTTGGCAAATCAAA | housekeeping gene | F1K |
| 9 (reverse) | TGCAGAATAAAACAAATTATAAA | housekeeping gene | R13 |
| 10 (forward) | CAGCAGTACAAATGGCAGTATTCA | tagged & WT integrase-encoding gene | 544F |
| 11 (reverse) | TCCTTTCCAAAGTGGATTACGTG | tagged integrase-encoding gene | 689R |
| 12 (reverse) | TTTCCAAAGTGGATTTCTGCTG | WT integrase-encoding gene | 689R |

In a further embodiment, the forward and reverse primers specific for quantitative amplification of tagged and non-tagged recombinant infectious virus include SEQ ID NOs: 19-20, and 24-25. SEQ ID NO: 19 is the forward primer which extends both the tagged envelope gene, and the WT envelope gene. SEQ ID NO: 20 is the reverse primer which extends both the tagged envelope gene, and the WT envelope gene. SEQ ID NO: 24 is the forward primer which extends the human genomic RPLPO gene. SEQ ID NO: 25 is the reverse primer which extends the human genomic RPLPO gene.

TABLE 3 primers specific for quantitative amplification of tagged and non-tagged recombinant infectious virus

| SEQ ID NO: | Primer sequence listed in 5' to 3' direction | useful for amplifying | name |
|---|---|---|---|
| 19 (forward) | ATTAACAAGAGATGGTGGTAA | tagged & WT env gene | 5HIV |
| 20 (reverse) | GTGCTACTCCTAATGGTTCAA | tagged & WT env gene | 3HIV |
| 24 (forward) | CATTCTATCATCAACGGGTA | human genomic RPLPO-gene | 5RO5 |
| 25 (reverse) | CAAAGGCAGATGGATCAG | human genomic RPLPO-gene | 3RO5 |

The primers described herein above and their homologues are claimed. Such primers are chosen from SEQ ID NOs: 5-12, 19-20, and 24-25, or have at least 80% homology, preferably 90% homology, more preferably 95% homology as determined using algorithms known to the person skilled in the art such as FASTA and BLAST. The primer sequences listed herein may optionally be labeled. Suitably, this label may be detected using fluorescence, luminescence or absorbance. In addition primers located in a region of 50 nucleotides (nt) upstream or downstream from the sequences given herein constitute part of the present invention. Specifically, the primers may be located in a region of 20 nt upstream or downstream from the sequences given herein and, constitute, as well, part of the present invention. Also, primers comprising at least 8 consecutive bases present in either of the primers described herein constitute an embodiment of the invention. Interestingly, the primers comprise at least 12 consecutive bases present in either of the primers described herein. In one aspect of the present invention the primers may contain linker regions for cloning. Optionally, the linker region of a primer may contain a restriction enzyme recognition site. Preferably, said restriction enzyme recognition site is a unique restriction enzyme recognition site. Alternatively, primers may partially anneal to the target region.

Methods for real time PCR use fluorescent primers or probes such as LUX™ fluorogenic primers, probes cleavable by DNAzymes or MNAzymes, TAQMAN® probes, molecular beacons, scorpions, or any other FRET probes. In one embodiment of the present invention, the quantitative amplification employs MNAzymes capable of cleaving fluorescent probes.

In the method according to the invention, the quantitative amplification may be performed by polymerase chain reaction, strand displacement amplification, or transcription-mediated amplification, employing LUX™ fluorogenic primers, TAQMAN® probes, molecular beacons, scorpions, DNAzymes, MNAzymes, or any other primers coupled to FRET probes. In one embodiment, the quantitative amplification is performed by polymerase chain reaction and employing MNAzymes, i.e. employing primers in the vicinity of MNAzymes, and probes that are cleaved by the MNAzymes.

LUX™ primers are oligonucleotides labeled with a single fluorophore. Typically 20-30 bases in length, they are designed with a fluorophore close to the 3' end in a hairpin structure. This configuration intrinsically renders fluorescence quenching capability; no separate quenching moiety is needed. When the primer becomes incorporated into double-stranded PCR product, the fluorophore is dequenched, resulting in a significant increase in fluorescent signal.

The TAQMAN® probes (Heid et al., 1996) use the fluorogenic 5' exonuclease activity of Taq polymerase to measure the amount of target sequences in cDNA samples. TAQMAN® probes are oligonucleotides that contain a fluorescent dye usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). When irradiated, the excited fluorescent dye transfers energy to the nearby quenching dye molecule rather than fluorescing (this is called FRET=Förster or fluorescence resonance energy transfer). Thus, the close proximity of the reporter and quencher prevents emission of any fluorescence while the probe is intact. TAQMAN® probes are designed to anneal to an internal region of a PCR product. When the polymerase replicates a template on which a TAQMAN® probe is bound, its 5' exonuclease activity cleaves the probe. This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (note that primers are not labeled). TAQMAN® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A "G" adjacent to the reporter dye quenches reporter fluorescence even after cleavage.

Molecular beacons are probes for the identification of specific nucleotide sequences present within cells (Tyagi et al., (1998) *Nature Biotechnology* 16:49-53). The molecular beacon can be composed of nucleic acid only such as DNA or RNA, or it can be composed of a peptide nucleic acid (PNA) conjugate. Binding of the molecular beacon to specific nucleotide sequences allows for the identification of the presence of those sequences either in vitro or in vivo. A molecular beacon includes a conjugate (e.g., a structure such as a quantum dot-tagged bead), a probe, a fluorophore, and a quenching moiety. The probe is a single-stranded oligonucleotide comprising a stem and loop structure wherein a hydrophilic attachment group is attached to one end of the single-stranded oligonucleotide and the quenching moiety is attached to the other end of the single-stranded oligonucleotide. The fluorophore can be any fluorescent organic dye or a single quantum dot such that its emission does not overlap with that of the quantum dot-tagged bead. The quenching moiety desirably quenches the luminescence of the fluorophore. Any suitable quenching moiety that quenches the luminescence of the fluorophore can be used in the conjugate described above.

Scorpions are bi-functional molecules containing a PCR primer covalently linked to a probe. The fluorophore in the probe interacts with a quencher which reduces fluorescence. During a PCR reaction the fluorophore and quencher are separated which leads to an increase in light output from the reaction tube. Scorpions are described more fully in Whitcombe, D., Theaker J., Guy, S. P., Brown, T., Little, S. (1999)—Detection of PCR products using self-probing amplicons and fluorescence. *Nature Biotech* 17, 804-807, and are protected under patent EP1088102.

A DNAzyme (Santoro, S. and Joyce, G., 1997, A general purpose RNA cleaving DNA enzyme. Proc Natl Acad Sci USA. 94: 4262-4266. Reviewed Emilsson, G. M. and Breaker, R. R., 2002, Deoxyribozymes: new activities and new applications. Cell. Mol. Life. Sci. 59, 596-607) is a catalytically active oligonucleotide that can, for example, cleave nucleic acid substrates at specific phosphodiester bonds. The DNAzyme consists of a catalytic domain flanked by two substrate recognition domains. It observes standard Watson-Crick base-pairing rules and must hybridize with its substrate to properly catalyze the cleavage. DNAzymes can be used in combination with in vitro amplification techniques, for example PCR, as a means of generating a detectable signal, thus allowing real time monitoring of amplified nucleic acid target sequences (U.S. Pat. No. 6,140,055). The DNAzymes are introduced into the amplicons by using primers with 5' tags that are inactive, anti-sense sequences of DNAzymes. When these sequences are copied during in vitro amplification the catalytically active sense DNAzyme sequences are co-amplified along with target sequence. This results in amplicons that function as DNAzymes capable of cleaving a reporter substrate. The essential reagents include one gene-specific primer conjoined to the inactive, antisense strand of the DNAzyme; and a second gene-specific primer. In an embodiment of the present invention, the 5' and 3' primers are specific for the target amplicons.

In addition to the DNAzyme, there is a DNAzyme-specific fluorogenic substrate. This universal probe consists of a short nucleic acid segment tagged with a fluorophore at one end and a BLACK HOLE QUENCHER™ dye (BHQ) at the other. The DNAzyme substrate ultimately serves as a measure of DNA copy number. With each round of amplification, the number of active DNAzymes increases in direct proportion to the DNA copy number. The exponential increase in DNAzyme activity leads to a corresponding increase in fluorescence, allowing the monitoring of DNA amplification in real time. In a preferred embodiment, the method starts with many copies of target DNA, because fewer cycles will be needed to reach a threshold level of detection, usually represented by the "Ct" value. The fluorophores present in the DNAzyme-specific fluorogenic substrate include FAM, CAL FLUOR ORANGE™, JOE, and TAMRA dyes amongst other. They emit strongly in their excited states but only weakly in their quenched states.

Figure 12:
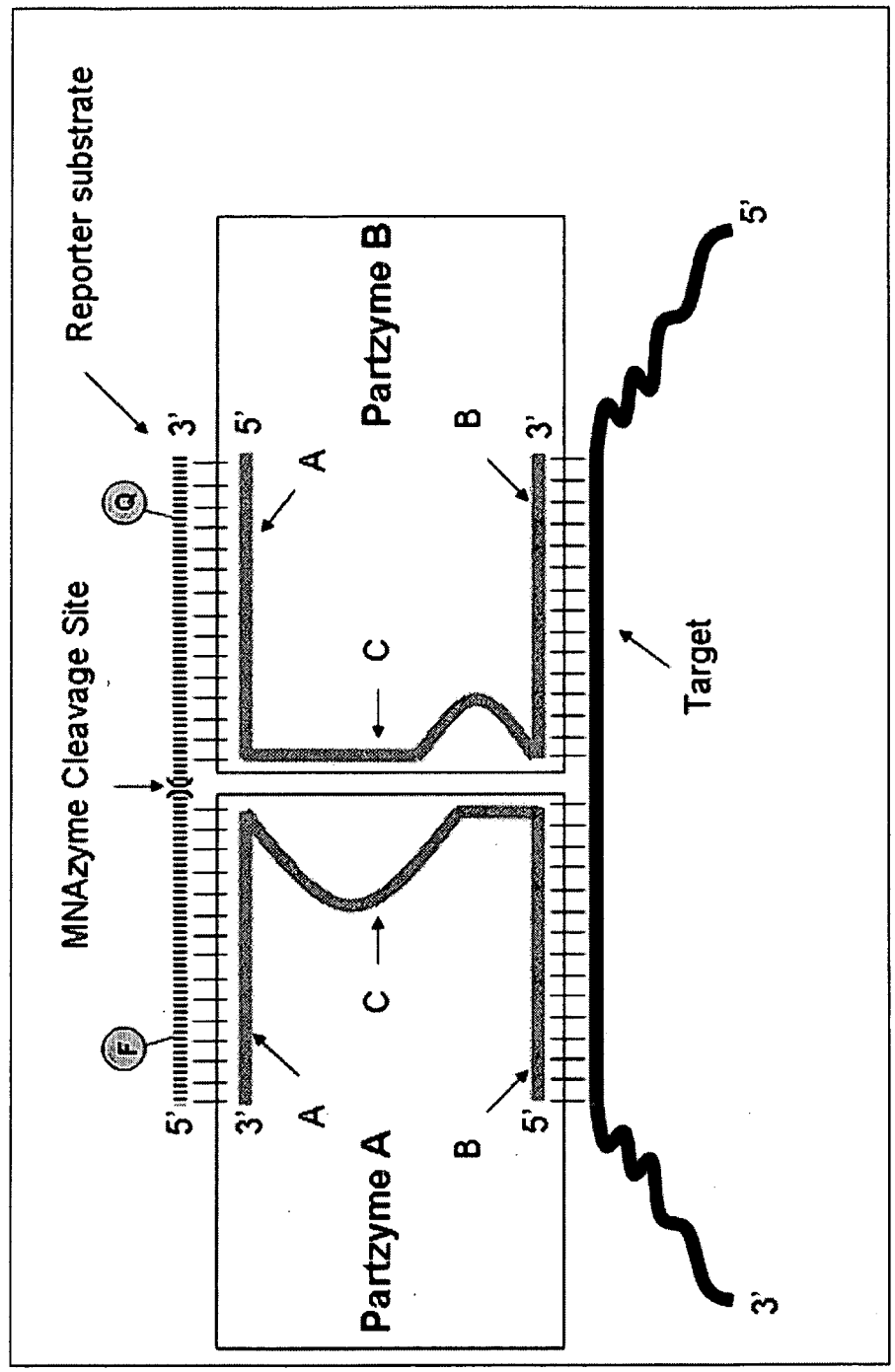
FIG. 12 is a depiction of an exemplary design for an MNAzyme, wherein substrate arm portions (A) of partzymes A and B bind to a Reporter substrate, to which is attached a fluorescent tag (left) and a quencher (right). Catalytic core portions (C) are located between substrate arm portions (A) and sensor arm portions (B). Upon binding of sensor arm portions (B) to a Target, the Reporter substrate is cleaved at the MNAzyme Cleavage Site, thereby increasing fluorescence.
Figure 13:
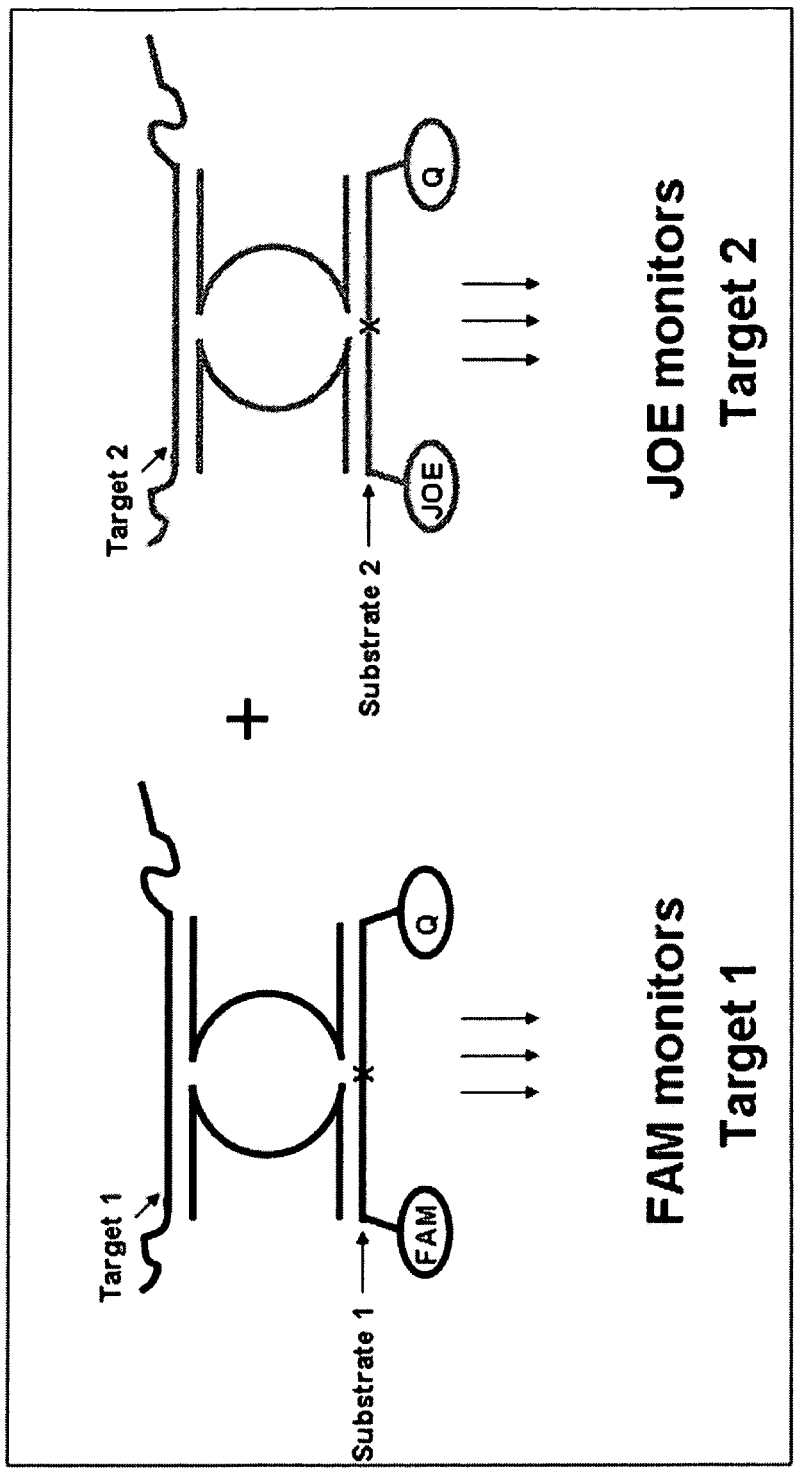
FIG. 13: Schematic representation of an exemplary multiplex analysis of multiple targets: Two or more targets can be simultaneously detected using two or more substrates, each specific for one MNAzyme. Substrates are preferably labeled with different fluorophores. In this example, Target 1 can be detected by monitoring the increase in FAM fluorescence and Target 2 can be detected by monitoring the increase in JOE fluorescence. Q: quencher; FAM, JOE: fluorophores.

MNAzymes (patent application PCT/AU2006/001473 by Johnson & Johnson Research Pty Limited, Australia) are catalytic nucleic acids based on DNAzymes. MNAzymes consist of two or more oligonucleotide sequences (e.g. partzymes) which, only in the presence of a MNAzyme assembly facilitator molecule (in this patent, the tagged or corresponding non-tagged region which is quantitatively amplified), form an active nucleic acid enzyme that is capable of catalytically modifying a substrate, for example a reporter substrate. An exemplary MNAzyme comprising partzyme A and partzyme B is depicted in FIG. 12. With reference to FIG. 12, DNA partzymes A and B each bind to a target, i.e. the MNAzyme assembly facilitator molecule (e.g., through Watson-Crick base pairing with a nucleic acid target). The MNAzyme only forms when the sensor arms of partzymes A and B hybridize adjacent to each other on the target. The substrate arms of the MNAzyme engage the reporter substrate, the cleavage of which is catalyzed by the catalytic core of the MNAzyme, formed by the interaction of the catalytic domains of partzymes A and B. The MNAzyme cleaves the substrate between a fluorophore and a quencher dye pair, thus generating signal. Cleavage of a DNA/RNA chimera (reporter substrate) is exemplified in the drawing. The term "MNAzyme" is also referred to as "multi-component nucleic acid enzyme". An MNAzyme may also comprise a stabilizing oligonucleotide which provides stability of the MNAzyme by interacting with an assembly facilitator or substrate. It is apparent that formation of an MNAzyme requires the assembly of at least the partzyme components with the target (or assembly facilitator), as well as the binding of a reporter substrate, for catalytic activity to be detectable, and that the absence of any of these components will result in a lack of catalytic activity.

The reporter substrate used with the MNAzymes can be labeled by any of a large variety of means including, for example, fluorophores (with or without one or more additional components, such as quenchers), radioactive labels, labeling with biotin (e.g. biotinylation) or chemiluminescent labels. Reporter substrates for catalytic nucleic acids may also include protein or nucleic acid enzymes, for example, covalently attached to their termini.

The reporter substrates used with the MNAzymes may be generic reporter substrate systems, which allow rapid assay development by allowing facile design changes to create new MNAzymes which recognize different targets. The substrate arm portion and the catalytic core portion of the partzymes may remain unchanged, with changes only to the sensor arm portion of one or more partzymes required for new targets. Generic substrate sequences are provided and the same substrate can therefore be incorporated in assays for many different targets. Further, the same substrate can be incorporated into the methods in various embodiments herein, including assays where the substrate is free in solution or is tethered or attached to a support. A series of generic substrates can be used in a multiplex reaction allowing simultaneous detection of multiple targets. MNAzyme strategies using generic substrates offer a major advantage over technologies such as TAQMAN® or Beacons which require the design and use of probes specific for each new target.

As described in more detail below, MNAzymes have an advantageous property in certain embodiments of being able to utilize a universal or generic reporter substrate. Such a substrate is shown in FIG. 12 in a presently preferred configuration wherein the reporter substrate comprises both a detectable portion and a quencher portion. The quencher portion is adapted to diminish or eliminate a detectable signal from the detectable portion of the substrate until the substrate is cleaved by the MNAzyme. For example, the quencher portion may comprise "BLACK HOLE QUENCHER™ 1" (BHQ1) or "BLACK HOLE QUENCHER™ 2" (BHQ2). Thus, the MNAzyme cleaves the reporter substrate between the detectable portion and the quencher portion allowing the two portions to separate in solution, thereby allowing the detectable signal to appear or increase as the quencher portion is distanced from, or effectively removed from the local environment of the detectable portion.

The use of the generic or universal reporter substrate is enabled through the design of the MNAzyme's component partzymes. By altering only the sensor arms of the partzymes, but by leaving the substrate arms unchanged, a large variety of MNAzymes specific for each of a plurality of targets can be designed all of which utilize a universal reporter substrate for detection. The skilled artisan will appreciate the advantages that this offers in terms of eliminating the need for customized or unique substrates for each target. Each new target requires only one or more changes in one or more of the sensor arm portions; the substrate arm portion and the catalytic core portion can remain constant. Thus, a single reporter substrate can be used for a single target using an MNAzyme, and multiple targets in a series of assays using altered MNAzymes. A plurality of reporter substrates allows multiplexing to detect multiple targets in a single assay using multiple MNAzymes, one for each target. Such multiplexed methods of using MNAzymes are readily accomplished in solution or with attachment to a support system. It is contemplated herein that multiplexed assays can thus be accomplished in systems involving attaching one or more of the reporter substrate, or the MNAzyme partzymes or assembly facilitator, or additional enzyme activities, to a support as described herein.

Substrates can be modified by an MNAzyme thereby providing a detectable effect. In the detection process, the reporter substrate modification by an MNAzyme may involve, for example, cleavage, ligation, porphyrin metallation, formation of carbon-carbon bonds, ester bonds or amide bonds. As a consequence of the reporter substrate modification by an MNAzyme, a detectable effect is generated and the magnitude of the effect may therefore be indicative of the quantity of the target sought to be measured. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

In one embodiment, the reporter substrates are SEQ ID NOs: 17-18, which are each labeled with a different fluorophore. The substrate with SEQ ID NO: 17 is end-labeled with a 6-FAM moiety at the 5' end and a BHQ moiety at the 3' end and is designated SubBi-6-FB. This substrate SEQ ID NO: 17 is useful to follow the accumulation of non-tagged wild type HXB2D WT amplicons and the cleavage of this substrate may be monitored at 516 nm with excitation at 492 nm. The substrate with SEQ ID NO: 18 is end-labeled with a 6-JOE moiety at the 5' end and a BHQ1 moiety at the 3' end and is designated SubBi-2-JB. This substrate SEQ ID NO: 18 is useful to follow the accumulation of tagged HXB2D amplicons and the cleavage of this substrate may be monitored at 555 nm with excitation at 535 nm.

In Table 4, these substrates are listed. The lower case bases represent RNA and the upper case bases represent DNA.

TABLE 4 reporter substrates sequences

| SEQ ID NO: | Substrate sequences listed in 5' to 3' direction | name |
|---|---|---|
| 17 | ATCACGCCTCguTCCTCCCAG | SubBi-6-FB |
| 18 | AAGGTTTCCTCguCCCTGGGCA | SubBi-2-JB |

In a further embodiment, the reporter substrates are SEQ ID NOs: 17-18 and 23, three different reporter substrates, which are each labeled with a different fluorophore. The substrate with SEQ ID NO: 17 is end-labeled with a 6-FAM moiety at the 5' end and a BHQ moiety at the 3' end and is designated SubBi-6-FB. The substrate SEQ ID NO: 17 is useful to follow the accumulation of non-tagged wild type HXB2D WT amplicons and the cleavage of this substrate may be monitored at 516 nm with excitation at 492 nm. The substrate with SEQ ID NO: 18 is end-labeled with a 6-JOE moiety at the 5' end and a BHQ1 moiety at the 3' end and is designated SubBi-2-JB. This substrate SEQ ID NO: 18 is useful to follow the accumulation of tagged HXB2D amplicons and the cleavage of this substrate may be monitored at 555 nm with excitation at 535 nm. The substrate with SEQ ID NO: 23 is end-labeled with a Quasar 670 moiety at the 5' end and a BHQ2 moiety at the 3' end and is designated SubBi-3-Q6B2. Alternatively, the substrate with SEQ ID NO: 23 may be end-labeled with a TAMRA moiety at the 5' end and a BHQ2 moiety at the 3' end. This substrate SEQ ID NO: 23 is useful to monitor the accumulation of RPLPO amplicons and the cleavage of this substrate may be monitored at 665 nm with excitation at 635 nm. The sequences of the three substrates are listed in Table 5. The lower case bases represent RNA and the upper case bases represent DNA.

TABLE 5 reporter substrates sequences

| SEQ ID NO: | Substrate sequence listed in 5' to 3' direction | Name |
|---|---|---|
| 17 | ATCACGCCTCguTCCTCCCAG | SubBi-6-FB |
| 18 | AAGGTTTCCTCguCCCTGGGCA | SubBi-2-JB |
| 23 | CAGCACAACCguCACCAACCG | SubBi-3-Q6B2 |

In one embodiment of the present invention, the MNAzyme structures are based on DNAzymes including the 10:23 and 8:17 DNAzymes. In various embodiments the MNAzymes comprise either or both ribonucleotide bases and deoxyribonucleotide bases. In more preferred embodiments, an MNAzyme structure is based at least in part on the structure of a DNAzyme. In other preferred embodiments, MNAzymes comprise at least some deoxyribonucleotide bases or analogues thereof. In more preferred embodiments, the catalytic core of an MNAzyme comprises one or more deoxyribonucleotide bases or analogues thereof. In still more preferred embodiments, one or more deoxyribonucleotide bases or analogues thereof are involved in the catalysis of a substrate. In other embodiments, at least one deoxyribonucleotide base, or its analogue, in the catalytic core improves catalytic activity. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates.

The skilled artisan will appreciate that MNAzymes comprise either deoxyribonucleotides or ribonucleotides, or even both. Those MNAzymes comprising at least one and more preferably, all, deoxyribonucleotide component oligonucleotides are presently preferred. Also preferred are those MNAzymes comprising at least one deoxyribonucleotide base, or its analogue, within the catalytic core of the MNAzyme. Even more preferred are those embodiments where such a base is required for catalytic activity.

A basic example of a MNAzyme structure is depicted in FIG. 12. The structure shown comprises partzyme A and partzyme B which have base-paired with an MNAzyme assembly facilitator molecule, shown here simply as Target. Partzymes A and B by interacting with Target, have allowed the catalytic core to come into close proximity and thereby form. The substrate arms of the MNAzyme have interacted with and base-paired with a substrate, here Reporter Substrate. Thus the MNAzyme has self-assembled and this process is facilitated through the presence of the MNAzyme assembly facilitator molecule Target. In the absence of Target, no MNAzyme will form. Modification (in this case, cleavage) of the substrate is catalyzed by the catalytic core of the MNAzyme at the MNAzyme Cleavage Site within the substrate denoted by the vertical arrow. The substrate in this particular embodiment of the invention comprises a detectable portion having a detectable signal, for example fluorophore F, and a quencher portion having a quenching effect on the detectable signal F through the action of quencher Q. Upon cleavage at the MNAzyme Cleavage Site, there is a substantial increase in detectable signal, here fluorescence, which is readily detected or quantified.

More specifically, the partzyme A and partzyme B, shown in FIG. 12, each comprise a substrate arm portion, a catalytic core portion, and a sensor arm portion. In the presence of a target, the sensor arm portions of partzyme A and partzyme B can begin to hybridize to, and base pair with complementary portions of the target, for example a DNA or RNA sequence. Upon contacting the target in this fashion, the MNAzyme self-assembles forming a catalytic core which can modify a substrate which is bound by the substrate arms. Preferably the presence of the MNAzyme is detected through the detection or measurement of its catalytic activity. The substrate arms of the thus assembled MNAzyme can engage a substrate, for example the reporter substrate shown in FIG. 12, through the interaction of the complementary sequences on the substrate arms and the substrate. Once the substrate is so engaged with the substrate arms, the catalytic core can promote the modification (eg. cleavage) of the substrate, which can in turn be measured or detected, directly or indirectly.

In one embodiment, the invention provides partzymes designed to detect two different target amplicons, namely those amplified from the non-tagged wild type HXB2D WT, and those amplified from the HXB2D-tagged sequences. In the following sequences the bases underlined form part of the catalytic core of the assembled MNAzyme, bases in bold hybridize with the target and bases in italics hybridize to the substrate. The P at the 3' end of the sequence indicates a 3' phosphate group.

TABLE 6 partzymes for the detection of two different target amplicons: the amplified non-tagged HXB2D WT sequences, and the amplified HXB2D-tagged sequences

| SEQ ID NO: | Partzyme sequences listed in 5' to 3' direction | name |
|---|---|---|
| 13 | ATATCTCCTCCTCCAGGT<u>ACAACG</u> <u>A</u>GAGGCGTGAT-P | Partzyme A HXB2D (wild type) WTA4/6-P |

TABLE 6-continued partzymes for the detection of two different
target amplicons: the amplified non-tagged
HXB2D WT sequences, and the amplified
HXB2D-tagged sequences

| SEQ ID NO: | Partzyme sequences listed in 5' to 3' direction | name |
|---|---|---|
| 14 | *CTGGGAGGAA*GGCTAGCT*CTGAAGA* TCTCGGACTCATT-P | Partzyme B HXB2D (wild type) WTB5/6-P |
| 15 | CTTCTCCAATTGTCCCTCATACAA *CGA*GAGGAAACCTT-P | Partzyme A HXB2D (tagged) TgA4/2-P |
| 16 | *TGCCCAGGGA*GGCTAGCT*GTCACCT* CCTCCGGG-P | Partzyme B HXB2D (tagged) TgB5/2-P |

In a further embodiment, the invention provides partzymes designed to detect three different target amplicons, namely those amplified from the non-tagged wild type HXB2D WT sequences, those amplified from the HXB2D-tagged sequences and those amplified from the RPLPO gene. In the following sequences the bases underlined form part of the catalytic core of the assembled MNAzyme, bases in bold hybridize with the target and bases in italics hybridize to the substrate. The P at the 3' end of the sequence indicates a 3' phosphate group.

TABLE 7 partzymes for the detection of three
different target amplicons: the amplified
non-tagged HXB2D WT sequences,
the amplified HXB2D-tagged sequences,
and the amplified RPLPO sequences

| SEQ ID NO: | Partzyme sequences listed in 5' to 3' direction | name |
|---|---|---|
| 13 | ATATCTCCTCCTCCAGGTACAACG *AGAGGCGTGAT*-P | Partzyme A HXB2D (wild type) WTA4/6-P |
| 14 | *CTGGGAGGAA*GGCTAGCT*CTGAAGA* TCTCGGACTCATT-P | Partzyme B HXB2D (wild type) WTB5/6-P |
| 15 | CTTCTCCAATTGTCCCTCATACAA *CGA*GAGGAAACCTT-P | Partzyme A HXB2D (tagged) TgA4/2-P |
| 16 | *TGCCCAGGGA*GGCTAGCT*GTCACCT* CCTCCGGG-P | Partzyme B HXB2D (tagged) TgB5/2-P |
| 21 | CAAACGAGTCCTGGCCTTGTCTAC AACGAGGTTGTGCTG-P | Partzyme A RPLPO R05A4/3-P |
| 22 | *CGGTTGGTGA*GGCTAGCT*GTGGAGA* CGGATTACACCTTC-P | Partzyme B RPLPO R05B5/3-P |

Multiple MNAzymes are useful in the present invention as they allow detection of related sequences differing by as little as a single nucleotide. Similarly, a unique reporter substrate is required to detect each of the several targets. In some cases, to multiplex the method requires the use of a distinct or unique detectable signal for each reporter substrate to facilitate the design of the method.

The target nucleic acid, encompassing the tagged or corresponding non-tagged regions of the recombinant virus of the present invention, is amplified in accordance with a procedure for amplifying that nucleic acid (i.e. DNA or RNA). Preferably, standard methods of in vitro amplification are used. The amplicons generated during the amplification serve as targets for an MNAzyme, thus MNAzyme activity is indicative of the presence of the target. The skilled artisan will appreciate that such monitoring can be conducted in a single vessel under conditions that permit both the amplification and the MNAzyme assembly and catalytic activity, or the MNAzyme assay can be conducted subsequent to, or at time points throughout the amplification, by removing samples at the end or during the course of the amplification reactions.

It is also to be appreciated that methods or protocols that combine target amplification with catalytic nucleic acid activity may require specific reaction conditions. Preferably, reaction conditions are compatible with both polymerase activity (for amplification), and catalytic nucleic acid modification of a substrate (for detection). Protocols for determining conditions for concurrent catalytic activity and polymerase activity at high temperature, such as during PCR, have been described for DNAzymes (Impey et al., 2000). The influence of factors including DNAzyme arm length, buffer, temperature, divalent ion concentration and effects of additives was demonstrated in this paper. DNA enzymes are suited for use in combination with in vitro amplification strategies. For example, they are not irreversibly denatured by exposure to high temperatures during amplification.

In one embodiment of the present invention, the quantitative amplification is performed according to a method for detecting the presence of at least one target or assembly facilitator, wherein the target or assembly facilitator is one tagged or corresponding non-tagged region of the recombinant virus as described above, said method comprising:

a) providing two or more oligonucleotide components, wherein at least a first oligonucleotide component and a second oligonucleotide component self-assemble in the presence of at least a first assembly facilitator to form at least a first catalytically active multi-component nucleic acid enzyme (MNAzyme);

b) providing at least a first reporter substrate, said first substrate capable of being modified by said first MNAzyme, wherein said modification of said substrate by said MNAzyme provides a detectable effect;

c) contacting said two or more oligonucleotide components with a sample putatively containing said at least first assembly facilitator under conditions permitting:

(1) the self-assembly of said at least first MNAzyme, and
(2) the catalytic activity of said at least first MNAzyme; and d) detecting said detectable effect.

The method for detecting the presence of at least one target or assembly facilitator may further comprise providing at least a third and fourth oligonucleotide component, wherein said at least third and at least fourth oligonucleotide component are capable of self assembling in the presence of at least one additional target or assembly facilitator to form at least one additional catalytically active MNAzyme, and wherein at least one additional reporter substrate is present in the sample, said additional reporter substrate is capable of being modified only by the additional MNAzyme, wherein said modification provides said additional detectable effect.

Determination of the Viral Replicative Capacity

Standard curves of threshold cycle (Ct) values over time for the tagged and/or non-tagged recombinant viruses are obtained and plotted onto the standard curves, generally obtained from a control or housekeeping gene, and the proportion of a given tagged species in the viral population or in a given environment is visualized and calculated.

The protocols and products of the present invention may be used for diverse diagnostic, clinical, toxicological, research and forensic purposes including, drug discovery, designing patient therapy, drug efficacy testing, and patient management. The present methods may be used in combination with other assays. The results may be implemented in computer models and databases.

Additionally, the protocols and products of the present invention also allow monitoring of the effect of anti-HIV compounds on viral fitness.

The viral fitness assay may be used as or comprise part of a high-throughput screening assay where numerous HIV strains and environmental compositions are evaluated. Results from viral fitness experiments can be used to develop a database of replicative capacity levels in the presence of other HIV strains, and environmental factors.

The present invention also provides a kit. The kit may be used for any of the methods described herein. In one embodiment, the kit may be used to determine the replicative capacity of two or more target HIV viruses in an environment. The kit of the invention may comprise a tagged HIV plasmid vector, a non-tagged HIV plasmid vector, primers, and probes. In another embodiment, a kit comprises a cell line. In one embodiment of the present invention, the kit encompasses one or more primers selected from SEQ ID NOs: 1-12, 19-20 and 24-25; and/or one or more of the tagged HIV plasmid vectors according to the invention, and optionally a non-tagged HIV HXB2D plasmid vector. The kits may further comprise environmental components. Alternatively, the kits may comprise as well the partzymes SEQ ID NOs: 13-16 and 21-22.

The order of the steps of the methods of the invention may be varied. One of skill in the art would be able to determine which variations in the order of the steps are applicable. Other embodiments of the invention will be apparent to those skilled in the art from consideration of the specification and practice of the invention disclosed herein. It is intended that the specification and examples be considered as exemplary only, with the scope being indicated by the claims.

The following non-limiting examples help to illustrate the principles of the invention.

EXPERIMENTAL PART

Abbreviations

MNAzyme: multi-component nucleic acid enzyme, or multipartite nucleic acid enzyme;
DNAzyme: deoxyribonucleic acid enzyme;
RNAzyme: ribonucleic acid enzyme, or ribozyme;
PCR: polymerase chain reaction;
$dH_2O$: deionized distilled water;
F: fluorophore;
Q: quencher;
JOE or 6-JOE: 6-carboxy-4',5'-dichloro-2',7'-dimethoxy-fluorescein;
FAM or 6-FAM: 6-Carboxyfluorescein;
BHQ1: BLACK HOLE QUENCHER™ 1;
BHQ2: BLACK HOLE QUENCHER™ 2.

Example 1

Recombinant virus were prepared according to the protocols explained in detail in EP877937, EP1283272 or EP1285971. The virus having a tagged envelope gene was the result of the recombination of the plasmid vector pGEM-HIVdelGPRT_tagged(env) and the amplicon GPRT. The virus having a tagged integrase sequence was the result of the recombination of the plasmid vector pGEM-HIVdelGPRT_tagged(int) and the amplicon GPRT. The virus having no tagged sequence was the result of the recombination of the plasmid vector pGEM-HIVdelGPRT and the amplicon GPRT. The amplicon GPRT refers to a sequence consisting of the last 81 amino acids of the gag gene, the full sequence of the protease gene, and the p51 part of the reverse transcriptase gene. The GPRT amplicons were obtained from a mutant virus strain and from a WT virus strain. The GPRT amplicon from the mutant strain was recombined with the tagged plasmid vector. The GPRT amplicon from the WT strain was recombined with the non-tagged plasmid vector. Recombination of the GPRT amplicon from the mutant strain with the non-tagged plasmid vector, and recombination of the GPRT amplicon from the WT strain with the tagged plasmid vector is another option.

The sequence of the plasmid vector pGEM-HIVdelGPRT tagged(env) is enclosed as SEQ ID NO: 13. The sequence of the plasmid vector pGEM-HIVdelGPRT_tagged(int) is enclosed as SEQ ID NO: 14. The sequence of the plasmid vector pGEM-HIVdelGPRT, i.e. with no tags, is enclosed as SEQ ID NO: 15.

The sequence of the envelope gene below shows in the underlined region where the silent mutations (marked in bold and in lower case) have been introduced:

```
Tagged envelope gene (SEQ ID NO: 26):
ATGAGAGTGAAGGAGAAATATCAGCACTTGTGGAGATGGGGGTGGAGATG

GGGCACCATGCTCCTTGGGATGTTGATGATCTGTAGTGCTACAGAAAAAT

TGTGGGTCACAGTCTATTATGGGGTACCTGTGTGGAAGGAAGCAACCACC

ACTCTATTTTGTGCATCAGATGCTAAAGCATATGATACAGAGGTACATAA

TGTTTGGGCCACACATGCCTGTGTACCCACAGACCCCAACCCACAAGAAG

TAGTATTGGTAAATGTGACAGAAAATTTTAACATGTGGAAAAATGACATG

GTAGAACAGATGCATGAGGATATAATCAGTTTATGGGATCAAAGCCTAAA

GCCATGTGTAAAATTAACCCCACTCTGTGTTAGTTTAAAGTGCACTGATT

TGAAGAATGATACTAATACCAATAGTAGTAGCGGGAGAATGATAATGGAG

AAAGGAGAGATAAAAAACTGCTCTTTCAATATCAGCACAAGCATAAGAGG

TAAGGTGCAGAAAGAATATGCATTTTTTTATAAACTTGATATAATACCAA

TAGATAATGATACTACCAGCTATAAGTTGACAAGTTGTAACACCTCAGTC

ATTACACAGGCCTGTCCAAAGGTATCCTTTGAGCCAATTCCCATACATTA

TTGTGCCCCGGCTGGTTTTGCGATTCTAAAATGTAATAATAAGACGTTCA

ATGGAACAGGACCATGTACAAATGTCAGCACAGTACAATGTACACATGGA

ATTAGGCCAGTAGTATCAACTCAACTGCTGTTAAATGGCAGTCTAGCAGA

AGAAGAGGTAGTAATTAGATCTGTCAATTTCACGGACAATGCTAAAACCA

TAATAGTACAGCTGAACACATCTGTAGAAATTAATTGTACAAGACCCAAC

AACAATACAAGAAAAAGAATCCGTATCCAGAGAGGACCAGGGAGAGCATT

TGTTACAATAGGAAAAATAGGAAATATGAGACAAGCACATTGTAACATTA

GTAGAGCAAATGGAATAACACTTTAAAACAGATAGCTAGCAAATTAAGA

GAACAATTTGGAAATAATAAAACAATAATCTTTAAGCAATCCTCAGGAGG

GGACCCAGAAATTGTAACGCACAGTTTTAATTGTGGAGGGGAATTTTTCT

ACTGTAATTCAACACAACTGTTTAATAGTACTTGGTTTAATAGTACTTGG
```

-continued

```
AGTACTGAAGGGTCAAATAACACTGAAGGAAGTGACACAATCACCCTCCC

ATGCAGAATAAAACAAATTATAAACATGTGGCAGAAAGTAGGAAAAGCAA

TGTATGCCCCTCCCATCAGTGGACAAATTAGATGTTCATCAAATATTACA

GGGCTGCTATTAACAAGAGATGGTGGTAATAGCAACAATGAGTCCGAGAT

CTTCAGgCCcGGAGGAGGtGAcATGAGGGACAATTGGAGAAGTGAATTAT

ATAAATATAAAGTAGTAAAAATTGAACCATTAGGAGTAGCACCCACCAAG

GCAAAGAGAAGAGTGGTGCAGAGAGAAAAAAGAGCAGTGGGAATAGGAGC

TTTGTTCCTTGGGTTCTTGGGAGCAGCAGGAAGCACTATGGGCGCAGCGT

CAATGACGCTGACGGTACAGGCCAGACAATTATTGTCTGGTATAGTGCAG

CAGCAGAACAATTTGCTGAGGGCTATTGAGGCGCAACAGCATCTGTTGCA

ACTCACAGTCTGGGGCATCAAGCAGCTCCAGGCAAGAATCCTGGCTGTGG

AAAGATACCTAAAGGATCAACAGCTCCTGGGGATTTGGGGTTGCTCTGGA

AAACTCATTTGCACCACTGCTGTGCCTTGGAATGCTAGTTGGAGTAATAA

ATCTCTGGAACAGATTTGGAATCACACGACCTGGATGGAGTGGGACAGAG

AAATTAACAATTACACAAGCTTAATACACTCCTTAATTGAAGAATCGCAA

AACCAGCAAGAAAAGAATGAACAAGAATTATTGGAATTAGATAAATGGGC

AAGTTTGTGGAATTGGTTTAACATAACAAATTGGCTGTGGTATATAAAAT

TATTCATAATGATAGTAGGAGGCTTGGTAGGTTTAAGAATAGTTTTTGCT

GTACTTTCTATAGTGAATAGAGTTAGGCAGGGATATTCACCATTATCGTT

TCAGACCCACCTCCCAACCCCGAGGGGACCCGACAGGCCCGAAGGAATAG

AAGAAGAAGGTGGAGAGAGAGACAGAGACAGATCCATTCGATTAGTGAAC

GGATCCTTGGCACTTATCTGGGACGATCTGCGGAGCCTGTGCCTCTTCAG

CTACCACCGCTTGAGAGACTTACTCTTGATTGTAACGAGGATTGTGGAAC

TTCTGGGACGCAGGGGTGGGAAGCCCTCAAATATTGGTGGAATCTCCTA

CAGTATTGGAGTCAGGAACTAAAGAATAGTGCTGTTAGCTTGCTCAATGC

CACAGCCATAGCAGTAGCTGAGGGGACAGATAGGGTTATAGAAGTAGTAC

AAGGAGCTTGTAGAGCTATTCGCCACATACCTAGAAGAATAAGACAGGGC

TTGGAAAGGATTTTGCTATAA
```

The sequence of the integrase encoding region below shows in the underlined region where the silent mutations (marked in bold and in lower case) have been introduced:

```
Tagged integrase-encoding sequence (SEQ ID NO 27):
TTTTTAGATGGAATAGATAAGGCCCAAGATGAACATGAGAAATATCACAG

TAATTGGAGAGCAATGGCTAGTGATTTTAACCTGCCACCTGTAGTAGCAA

AAGAAATAGTAGCCAGCTGTGATAAATGTCAGCTAAAAGGAGAAGCCATG

CATGGACAAGTAGACTGTAGTCCAGGAATATGGCAACTAGATTGTACACA

TTTAGAAGGAAAAGTTATCCTGGTAGCAGTTCATGTAGCCAGTGGATATA

TAGAAGCAGAAGTTATTCCAGCAGAAACAGGGCAGGAAACAGCATATTTT

CTTTTAAAATTAGCAGGAAGATGGCCAGTAAAAACAATACATACAGACAA

TGGCAGCAATTTCACCAGTGCTACGGTTAAGGCCGCCTGTTGGTGGGCGG

GAATCAAGCAGGAATTTGGAATTCCCTACAATCCCCAAAGTCAAGGAGTA

GTAGAATCTATGAATAAAGAATTAAAGAAAATTATAGGACAGGTAAGAGA

TCAGGCTGAACATCTTAAGACAGCAGTACAAATGGCAGTATTCATCCACA

ATTTTAAAAGAAAAGGGGGGATTGGGGGGTACAGTGCAGGGGAAAGAATA

GTAGACATAATAGCAACAGACATACAAACTAAAGAATTACAAAAACAAAT

TACAAAAATTCAAAATTTTCGGGTTTATTACAGGGACtcacGtAATCCAC

TTTGGAAAGGACCAGCAAAGCTCCTCTGGAAAGGTGAAGGGGCAGTAGTA

ATACAAGATAATAGTGACATAAAAGTAGTGCCAAGAAGAAAAGCAAAGAT

CATTAGGGATTATGGAAAACAGATGGCAGGTGATGATTGTGTGGCAAGTA

GACAGGATGAGGATTAG
```

Once the recombinant viruses had been generated, six tubes containing 7.5×10⁶ MT4-LTR-EGFP cells were prepared. Then, 8 ml of the recombinant virus pre-dilutions were prepared according to the following formula (MOI: multiplicity of infection):

Final dilution for MOI of 0.001/20=pre-dilution factor

The recombinant virus were added to the re-suspended cells according to the following table 8 at the conditions described below:

TABLE 8

| Ratio Tag/WT | Amount of Tag virus (mL) (HIV HXB2D-tagged) | Amount of WT virus (mL) (HIV HXB2D WT) |
|---|---|---|
| 100/0 | 2.5 | 0 |
| 0/100 | 0 | 2.5 |
| 80/20 | 2 | 0.5 |
| 50/50 | 1.25 | 1.25 |
| 20/80 | 0.5 | 2 |
| Control | 0 | 0 |

The mixture of virus and cells was incubated for 30 minutes at 37° C., followed by a spinoculation of 10 minutes at 1200×g. The supernatants were removed and the cells washed with medium. The tubes were centrifuged for 5 minutes at 200×g and the pellets re-suspended in culture media. The re-suspended cells were added to culture flasks containing culture media and incubated at 37° C. The time was carefully annotated.

Each every 24 hours after, the flasks were scored for cytopathogenic effect and fluorescence. At Time 0 hours (after wash step), 15 h., 24 h., 39 h., 48 h., 63 h., 72 h. and 87 h., 6 ml of the re-suspended cell culture was collected. Supernatants and cells were recovered by centrifugation: after 10 minutes at 1800×g, 2×1.5 ml of supernatant was collected.

400 µl of PBS was added to the remainder of the supernatant to re-suspend the cell pellet. The re-suspended cells were split over 2 tubes and both supernatant and cells were stored at—80° C.

DNA was extracted from the cell pellets with the INVISORB® Spin Blood Mini kit from INVITEK® (Westburg) according to the protocol provided by the supplier. DNA concentrations were measured with the spectrophotometer, and the DNA concentration was adjusted to 100 ng/µl. Samples were then stored at—20° C.

2 µl of the stored samples were used for testing in the real-time assay. The DNA was added to a real-time PCR mix and placed in the PCR machine. The real-time PCR mix contained wild-type primer Mix, universal substrate FAM, tag primer mix, universal substrate JOE, control primer mix, universal substrate FAMTAM, BD QTAQ™ PCR buffer with FAMTAM, PCR-grade water, and BD QTAQ™ DNA polymerase mix.

The mix of 2 μl of DNA template and the real-time PCR mix was placed in a thermocycler (ABI 7700) at the following program:

| | | |
|---|---|---|
| 3 minutes | 95° C. | |
| 15 seconds | 95° C. | 10 cycles |
| 1 minutes | 66° C. – 1° C./cycle | |
| 15 seconds | 95° C. | 45 cycles |
| 1 minute | 56° C. | |

The resulting Ct (threshold cycle) values were used for determining the replicative capacity of the tag virus and the wild-type virus.

Figure 5:
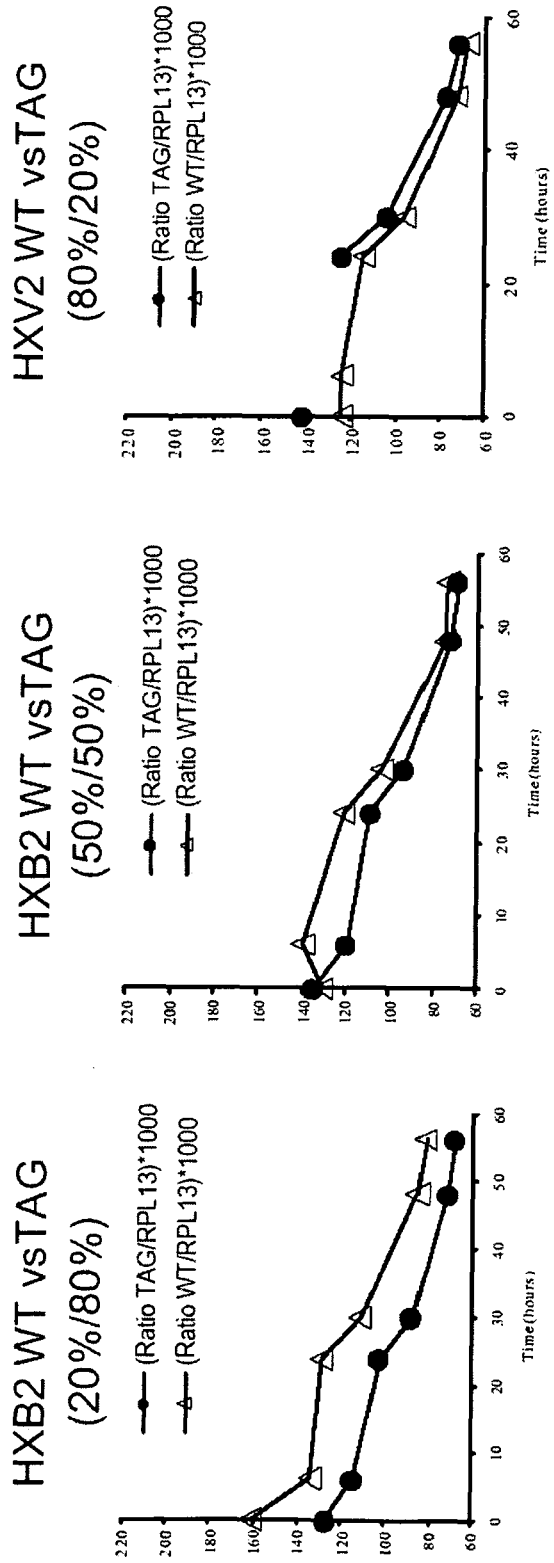
FIG. 5 is a comparison of the viral growth of HIV HXB2D WT and HIV HXB2D-tagged in MT4 cells overtime at various relative input concentrations.
Figure 6:
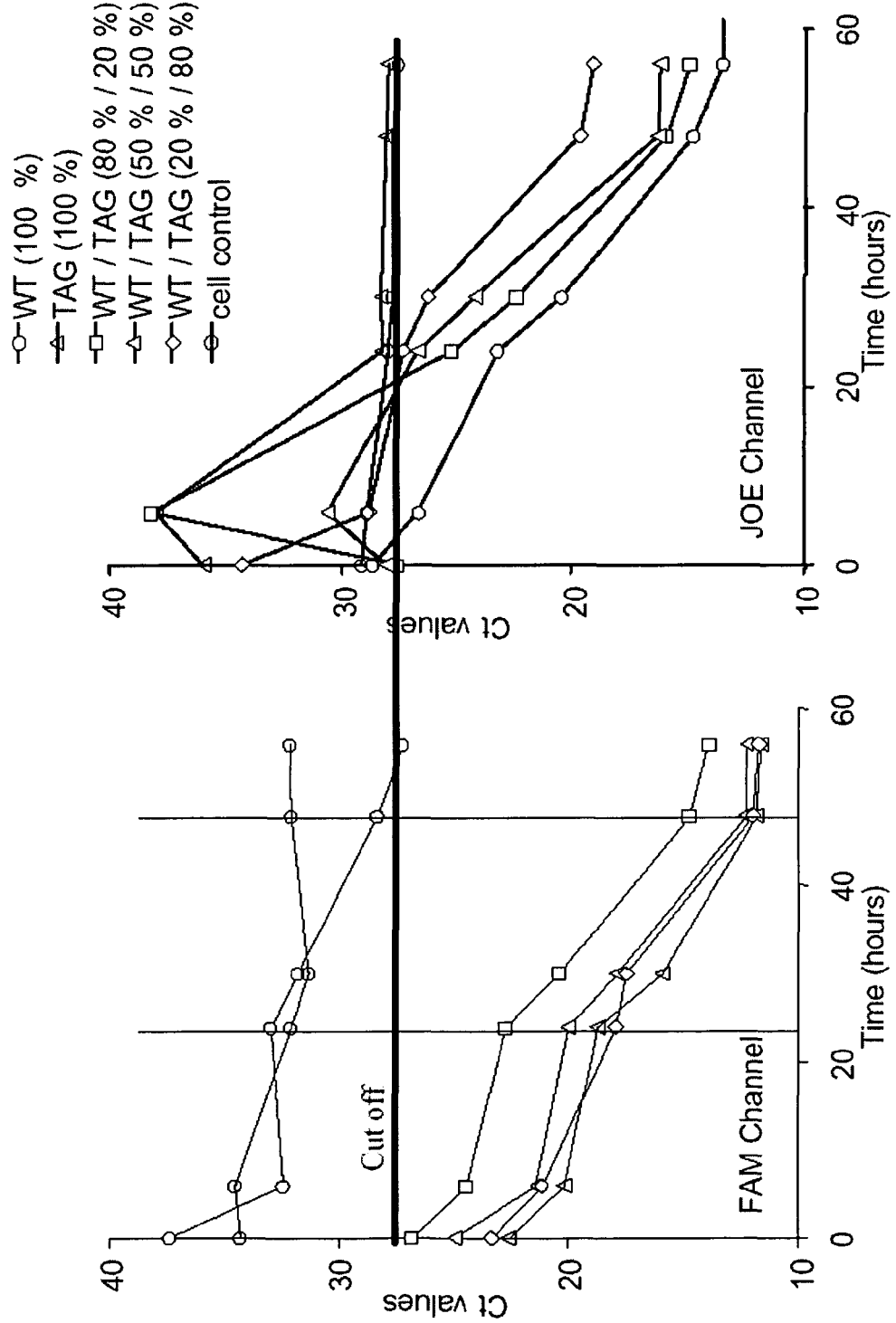
FIG. 6 plots the detection of HIV HXB2D WT and HIV HXB2D-tagged DNA from co-infected MT4 cells using dual labeling.

In FIG. 5, a comparison of the viral growth of HIV HXB2D WT and HIV HXB2D-tagged in MT4 cells overtime at various relative input concentrations. Further in FIG. 6, there is plotted the detection of HIV HXB2D and HIV HXB2D-tagged DNA from co-infected MT4 cells using dual labeling, wherein the tagged primer is linked to the JOE probe, and the non-tagged wild-type primer is linked to the FAM probe.

Figure 7A:
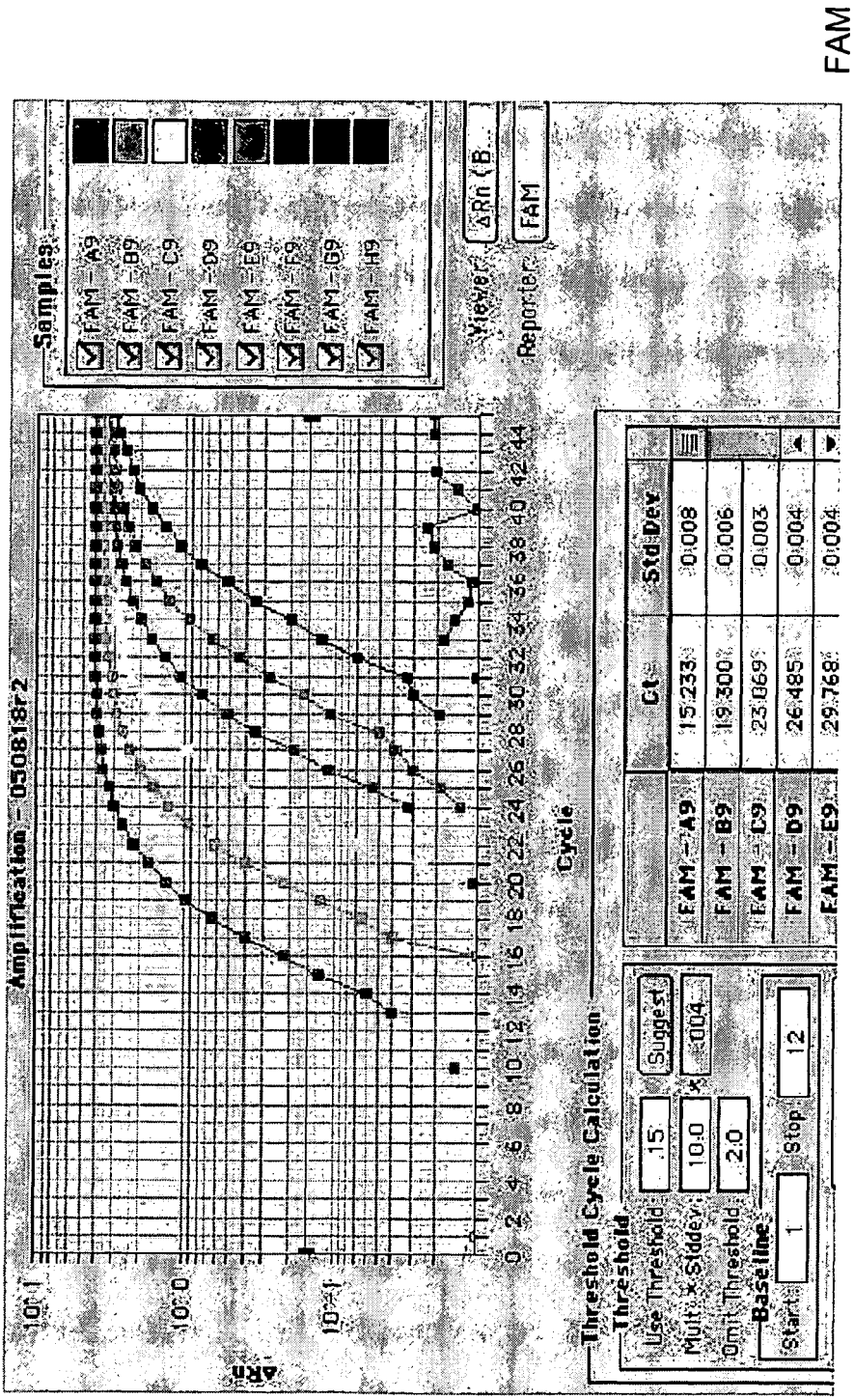
FIGS. 7a, 7b and 7c show the amplification curves for the templates HIV HXB2D and HIV HXB2D-tagged DNA, amplified with primers SEQ ID NOs: 7 and 6. The B-FAM label corresponds to the HIV HXB2D DNA (FIG. 7a), the D-JOE corresponds to the HIV HXB2D-tagged DNA (FIG. 7b) and the TAMRA corresponds to the housekeeping gene (GAPD) (FIG. 7c).
Figure 7B:
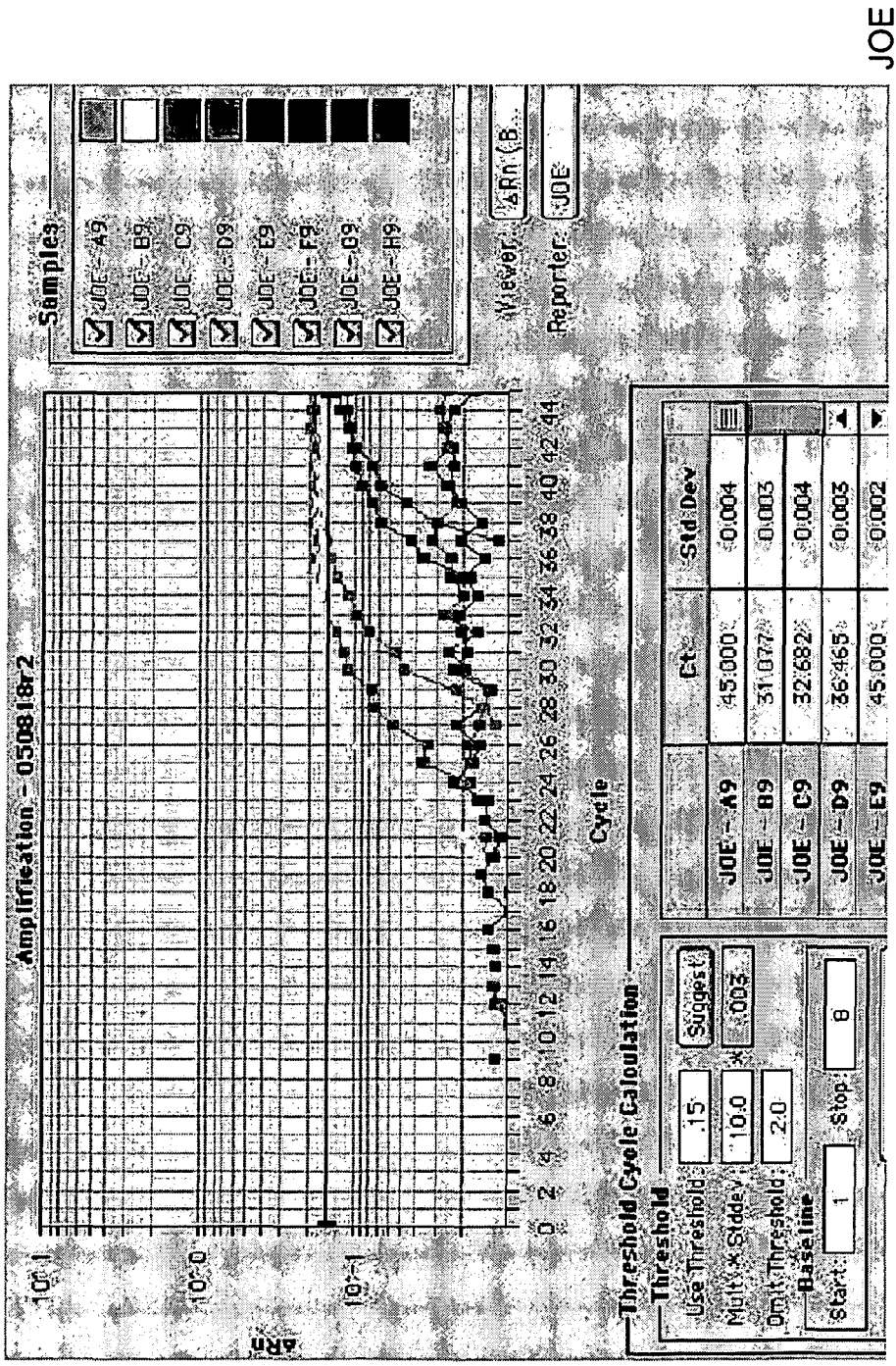
Figure 7C:
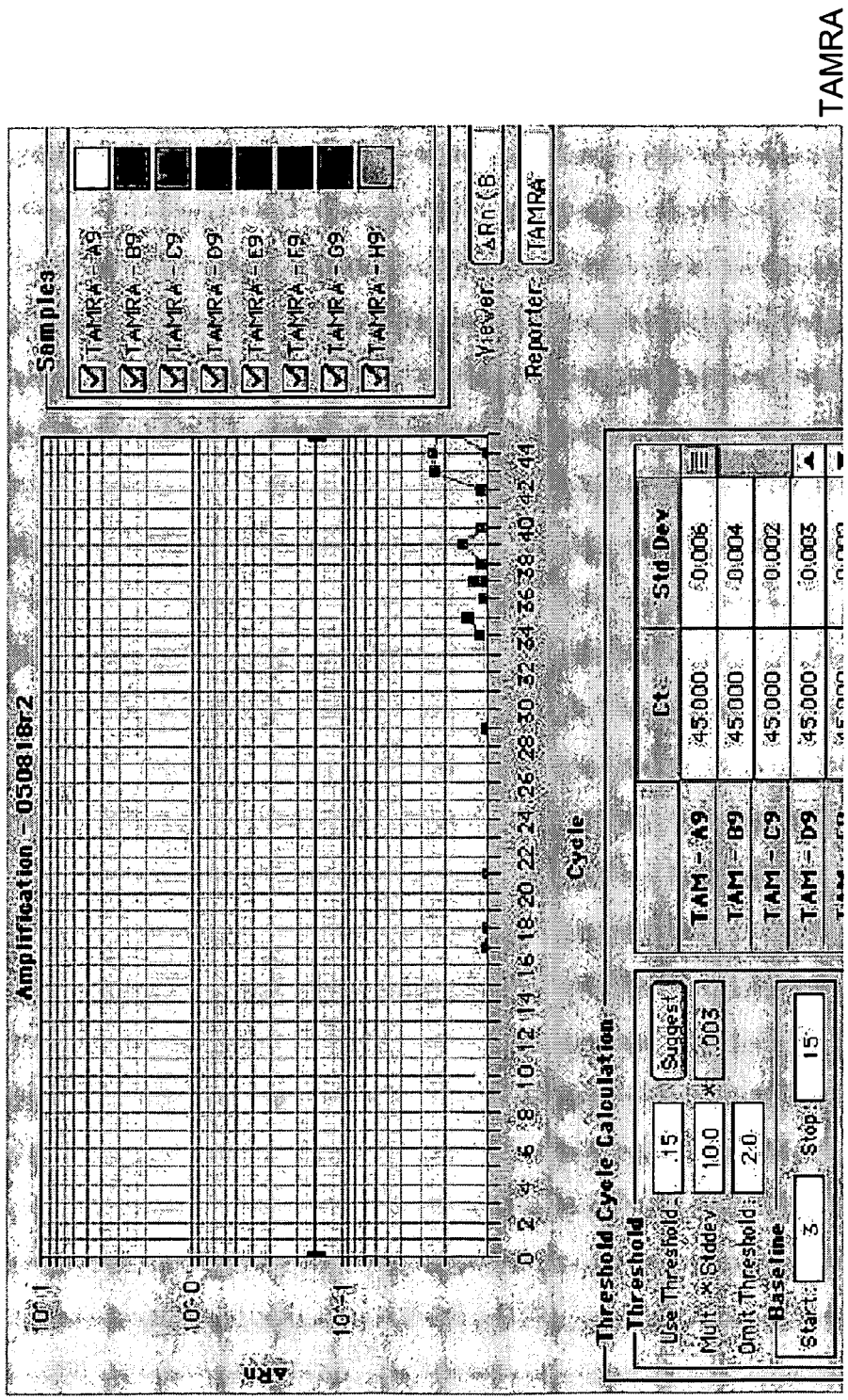

In FIGS. 7a, 7b and 7c, three amplification curves are shown for the templates HIV HXB2D and HIV HXB2D-tagged DNA which were used to co-infect MT4 cells. The primers used were SEQ ID NOs: 7 and 6, and the labels that were used were:
B-FAM for the HIV HXB2D DNA (FIG. 7a)
D-JOE for the HIV HXB2D-tagged DNA (FIG. 7b)
TAMRA for the housekeeping gene (GAPD) (FIG. 7C)

Figure 8A:
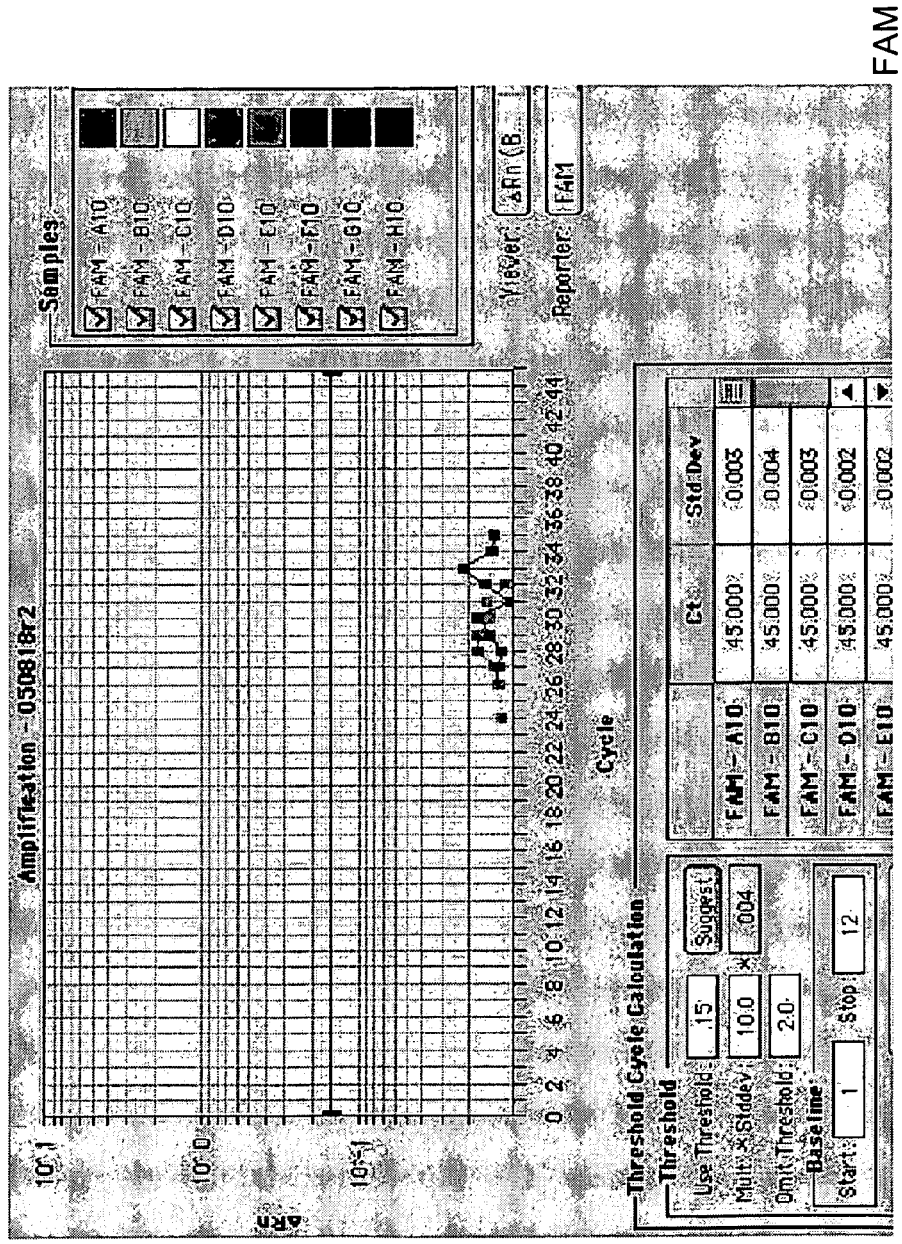
FIGS. 8a, 8b and 8c show the amplification curves for the templates HIV HXB2D and HIV HXB2D-tagged DNA, amplified with primers SEQ ID NOs: 5 and 6. The B-FAM label corresponds to the HIV HXB2D DNA (FIG. 8a), the D-JOE corresponds to the HIV HXB2D-tagged DNA (FIG. 8b) and the TAMRA corresponds to the housekeeping gene (GAPD) (FIG. 8c).
Figure 8B:
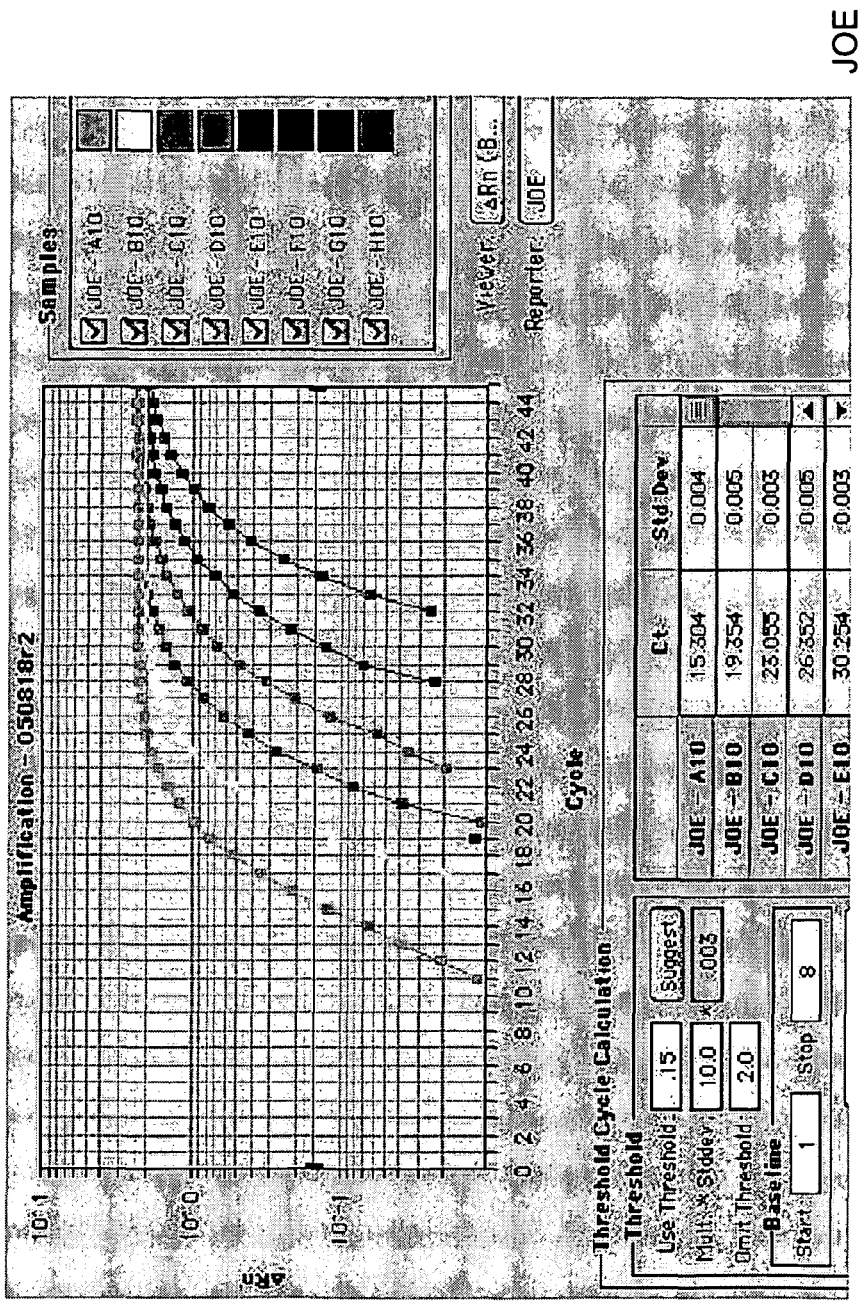
Figure 8C:
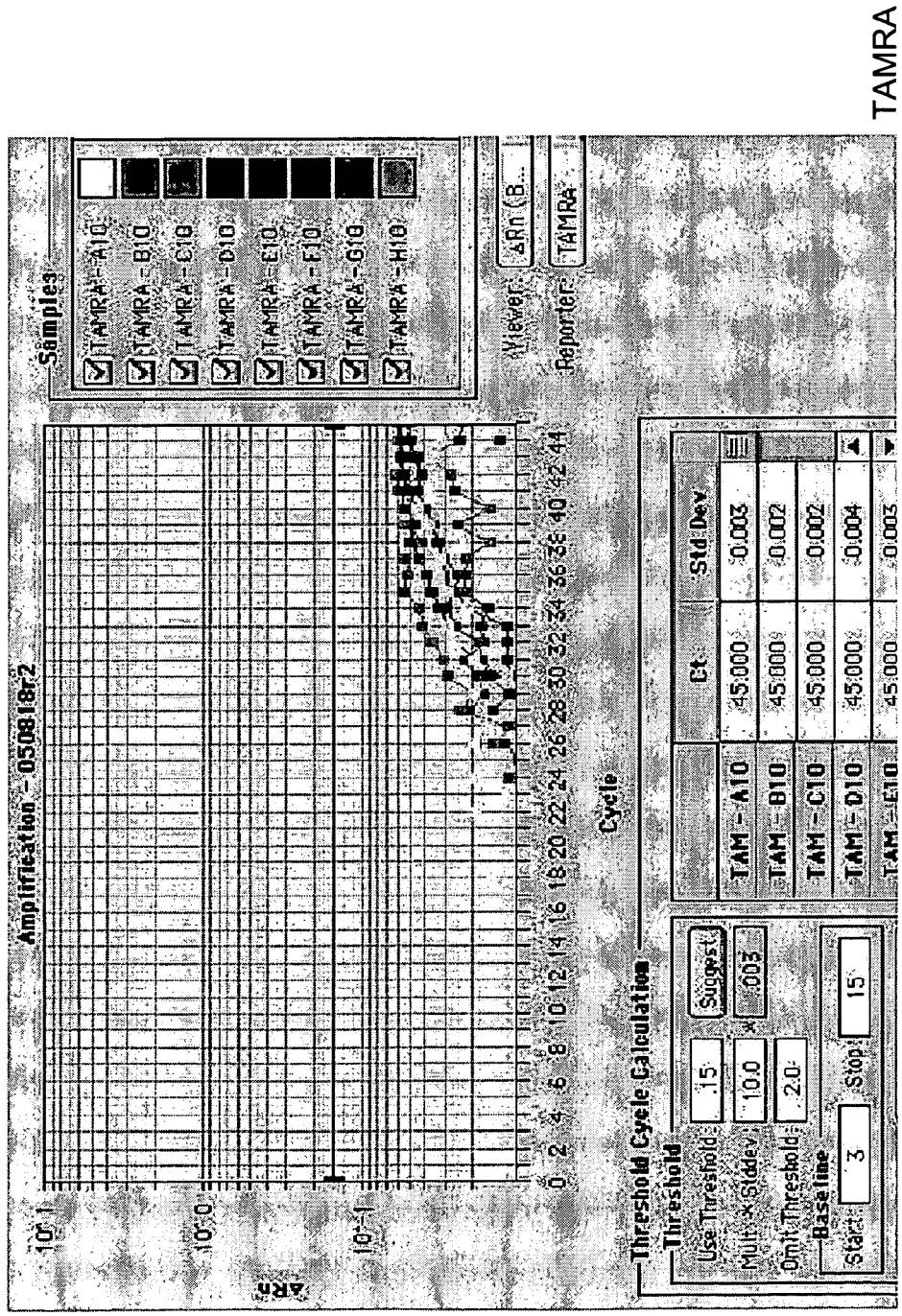

In FIGS. 8a, 8b and 8c, three amplification curves are shown for the templates HIV HXB2D and HIV HXB2D-tagged DNA which were used to co-infect MT4 cells. The primers used were SEQ ID NOs: 5 and 6, and the labels that were used were:
B-FAM for the HIV HXB2D DNA (FIG. 8a)
D-JOE for the HIV HXB2D-tagged DNA (FIG. 8b)
TAMRA for the housekeeping gene (GAPD) (FIG. 8c)

Figure 9A:
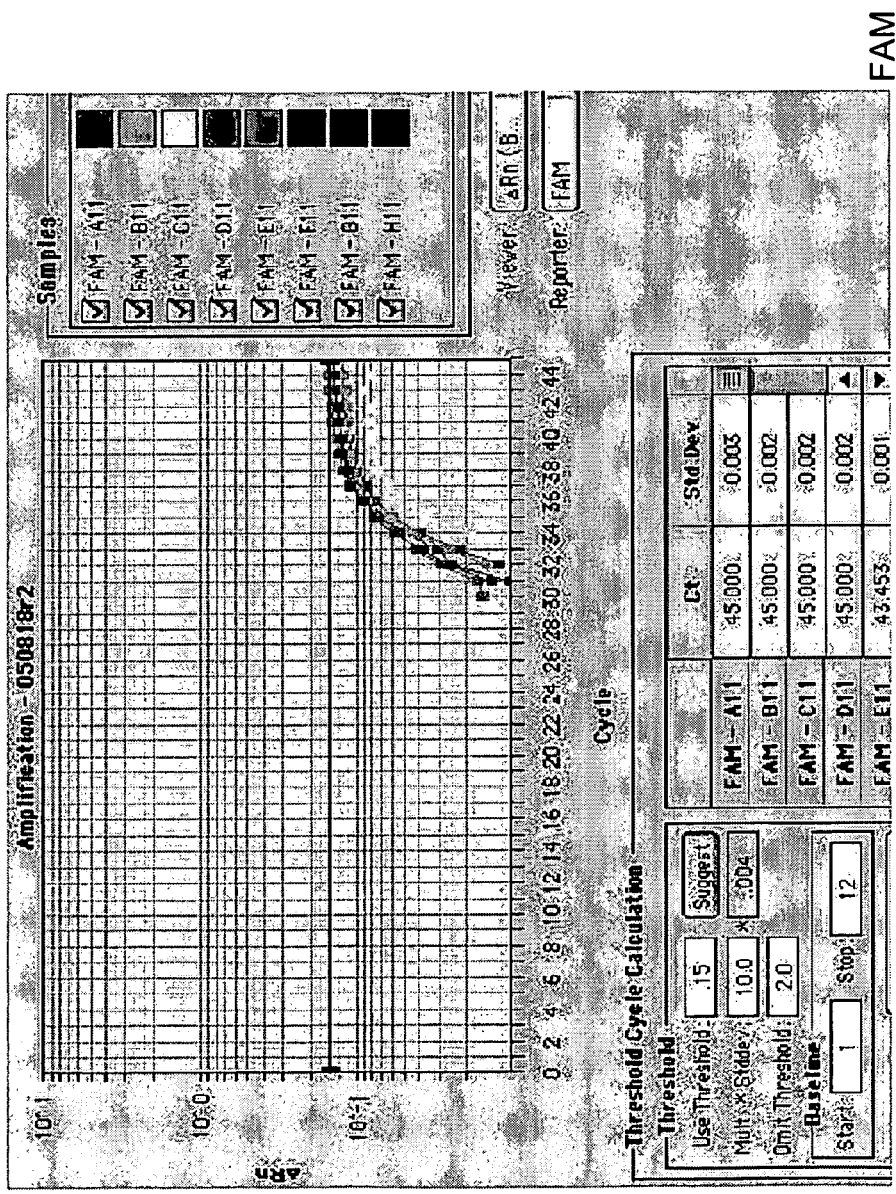
FIGS. 9a, 9b and 9c show the amplification curves for the templates HIV HXB2D and HIV HXB2D-tagged DNA, amplified with primers SEQ ID NOs: 8 and 9. The B-FAM label corresponds to the HIV HXB2D DNA (FIG. 9a), the D-JOE corresponds to the HIV HXB2D-tagged DNA (FIG. 9b) and the TAMRA corresponds to the housekeeping gene (GAPD) (FIG. 9c).
Figure 9B:
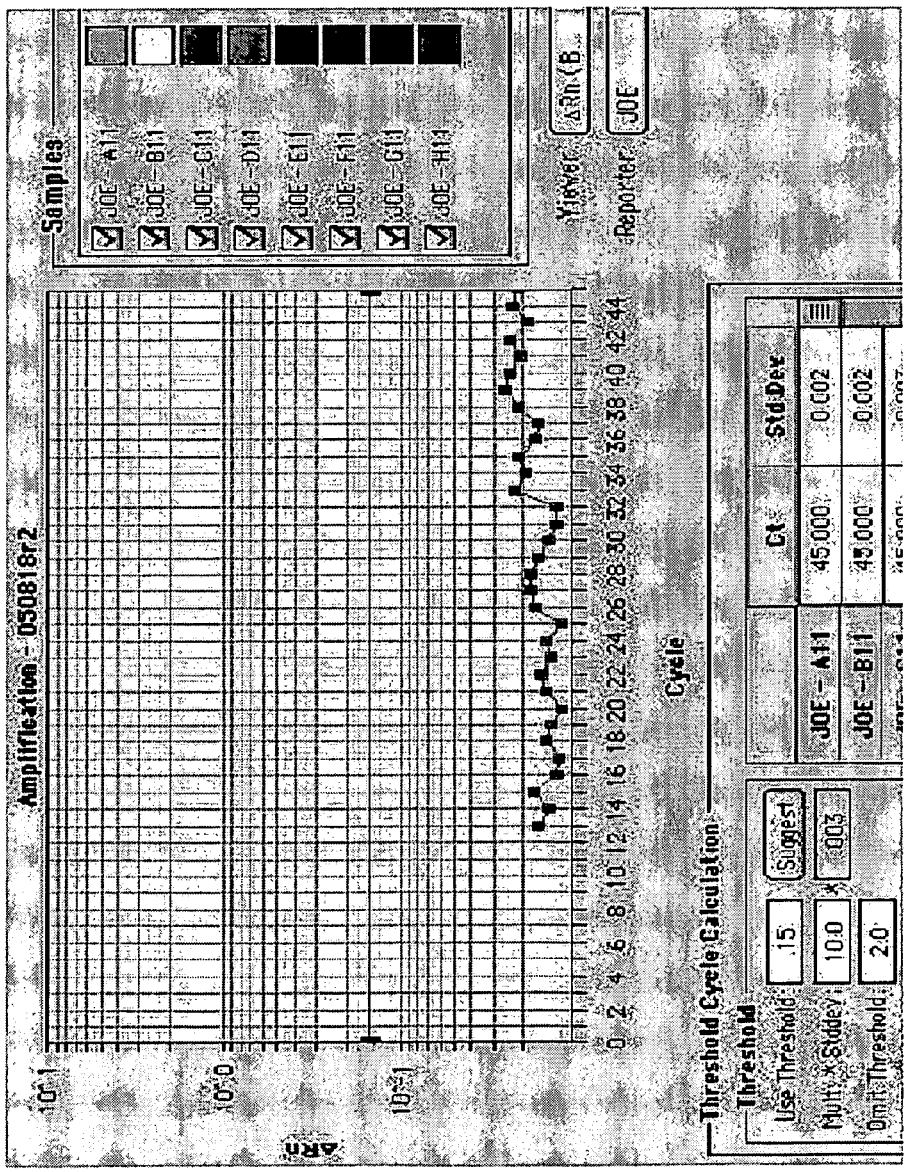
Figure 9C:
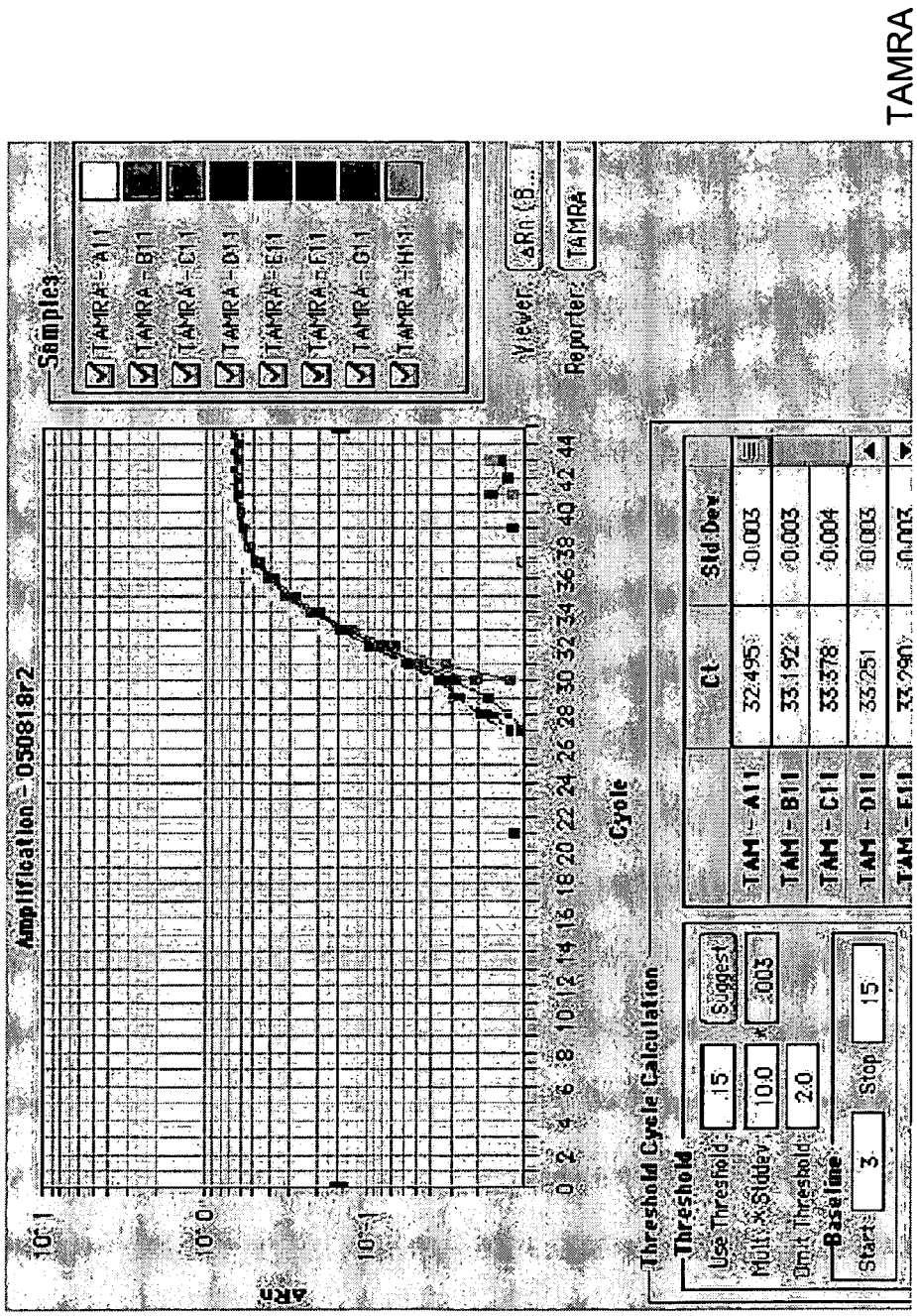

In FIGS. 9a, 9b and 9c, three amplification curves are shown for the templates HIV HXB2D and HIV HXB2D-tagged DNA which were used to co-infect MT4 cells. The primers used were SEQ ID NOs: 8 and 9, and the labels that were used were:
B-FAM for the HIV HXB2D DNA (FIG. 9a)
D-JOE for the HIV HXB2D-tagged DNA (FIG. 9b)
TAMRA for the housekeeping gene (GAPD) (FIG. 9c)

Figure 10A:
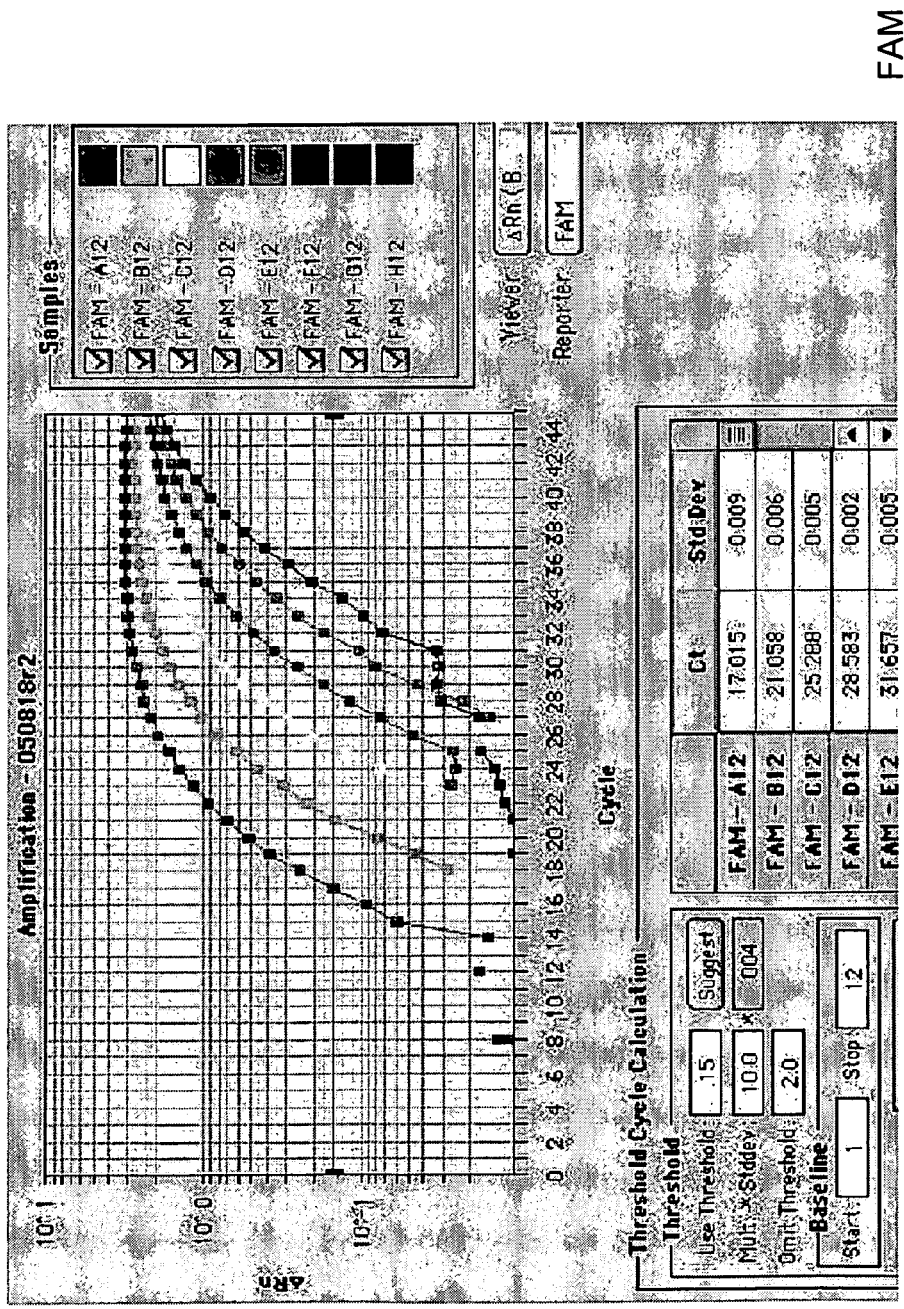
FIGS. 10a, 10b and 10c show the amplification curves for the templates HIV HXB2D and HIV HXB2D-tagged DNA, amplified with primers SEQ ID NOs: 5, 6, 7, 8 and 9. The B-FAM label corresponds to the HIV HXB2D DNA (FIG. 10a), the D-JOE corresponds to the HIV HXB2D-tagged DNA (FIG. 10b) and the TAMRA corresponds to the housekeeping gene (GAPD) (FIG. 10C).
Figure 10B:
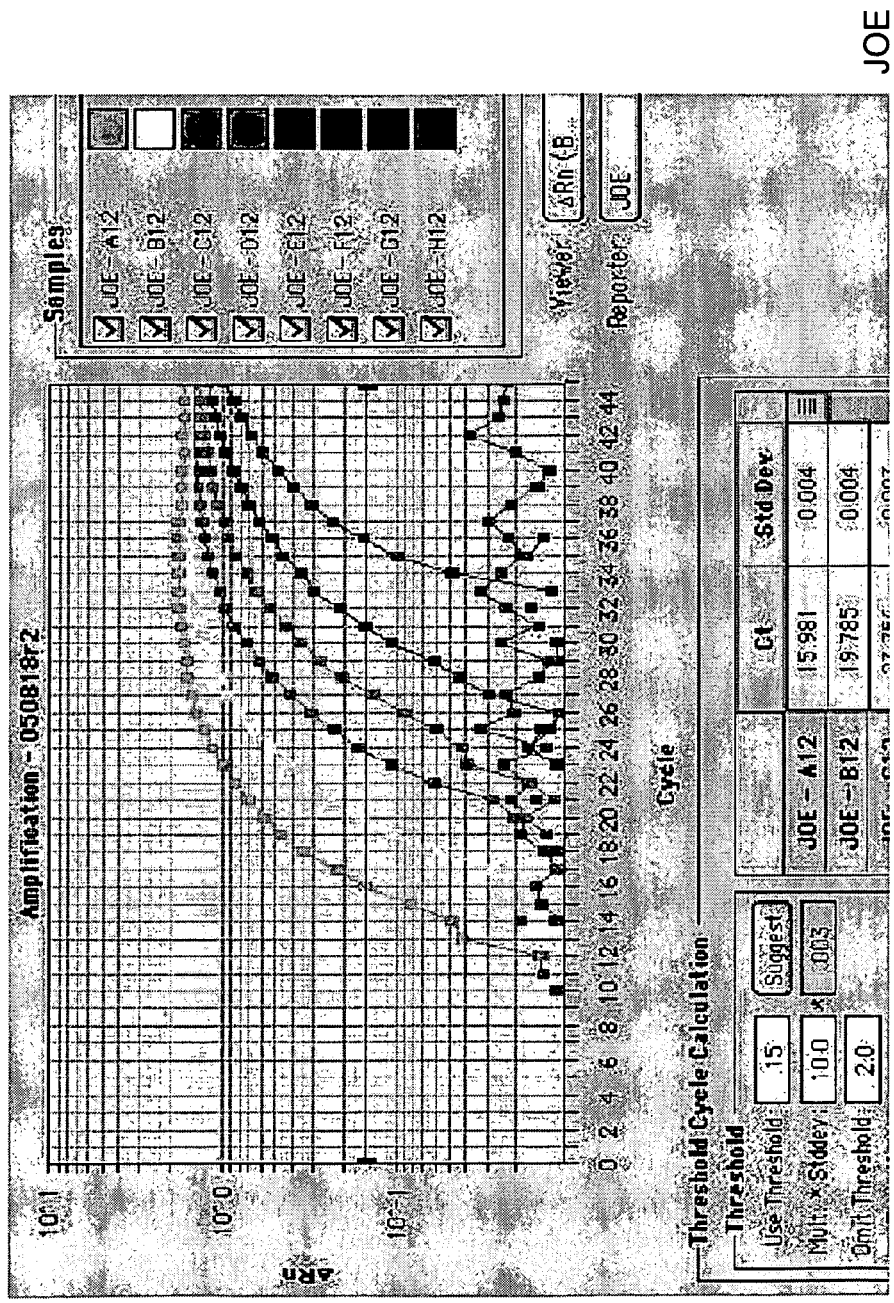
Figure 10C:
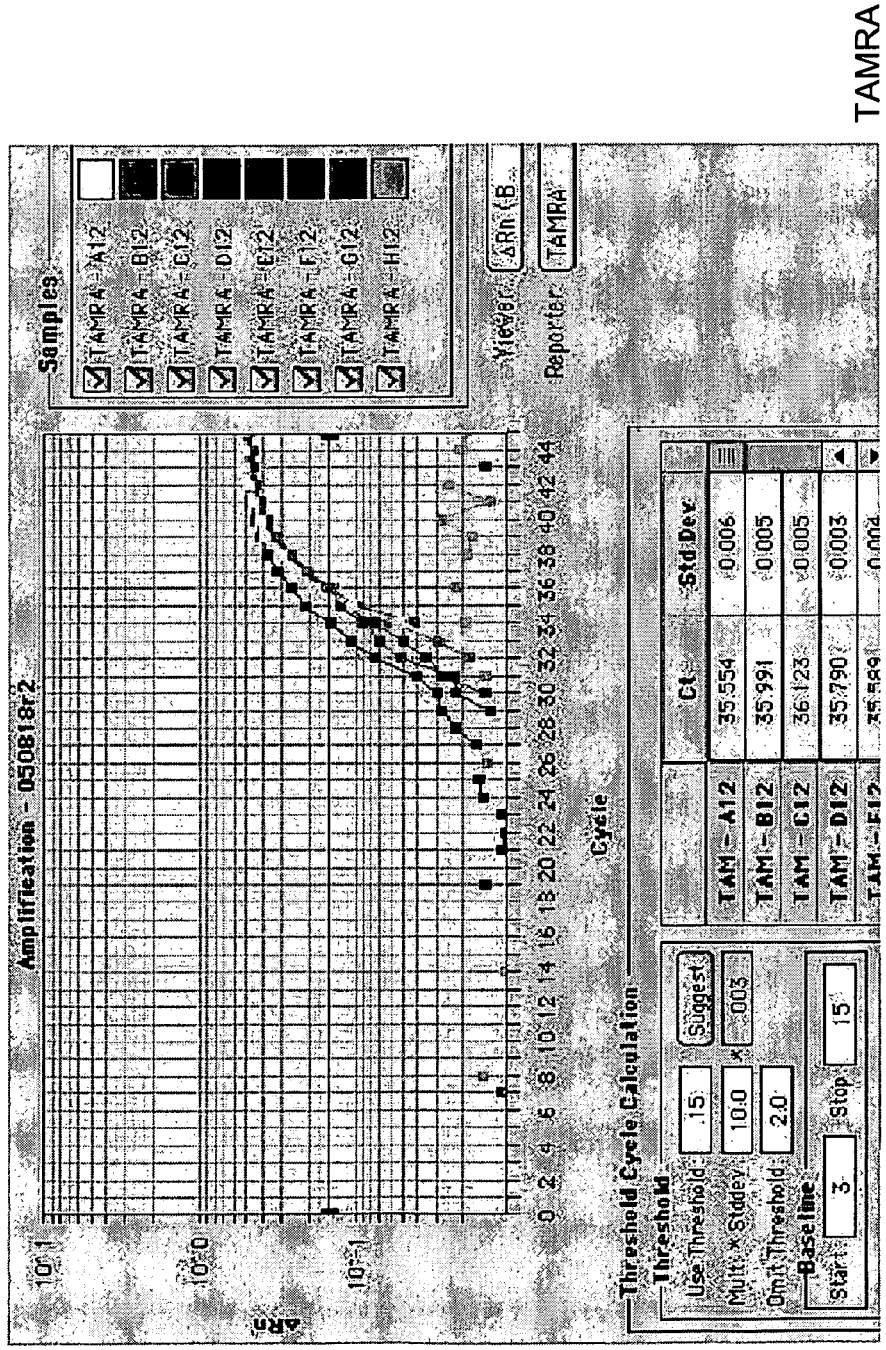

In FIGS. 10a, 10b and 10c, three amplification curves are shown for the templates HIV HXB2D and HIV HXB2D-tagged DNA which were used to co-infect MT4 cells. The primers used were SEQ ID NOs: 5, 6, 7, 8 and 9, and the labels that were used were:
B-FAM for the HIV HXB2D DNA (FIG. 10a)
D-JOE for the HIV HXB2D-tagged DNA (FIG. 10b)
TAMRA for the housekeeping gene (GAPD) (FIG. 10c)

Figure 11:
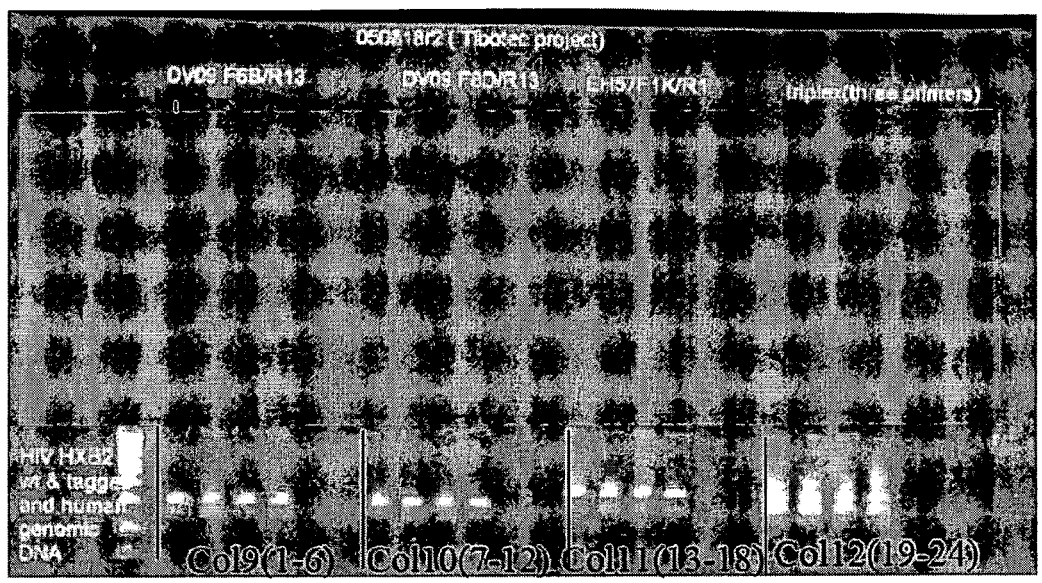
FIG. 11 provides the pictures of the end point gel electrophoresis for the amplified material shown in FIGS. 7-10.

In FIG. 11 there is provided the pictures of the end point gel electrophoresis for the amplified material shown in FIGS. 7-10. The pictures clearly show that a viable triplex assay has been developed which is able to differentiate between non-tagged WT and tagged HIV DNA vector templates (i.e. HIV HXB2D vs. HIV HXB2D-tagged DNA), even in the presence of genomic DNA background. The PCR efficiency is within 90% and 110%, the correlation coefficient of data fit to standard curve is ≥0.99. The ΔCt (i.e. variation of threshold cycle) between 1- and n-plex was ≤1 cycle.

Example 2

Use of MNAzymes for the Quantification of HIV Nucleic Acid Sequences Via Duplex Real Time PCR Multicomponent Nucleic Acid enzymes (MNAzymes) contain (i) sensor regions which specifically recognise and bind an assembly facilitator, for example a target nucleic acid; (ii) catalytic core regions; and (iii) substrate regions which bind a substrate. MNAzymes are composed of two (or more) separate oligonucleotide "partzymes" which form an active enzyme only in the presence of an assembly facilitator. The catalytically active MNAzyme can cleave nucleic acid reporter substrates between fluorophore and quencher dye pairs thus generating fluorescent signal. Examples of assembly facilitators include target analytes such as DNA or RNA sequences. MNAzymes can be used to allow detection of target DNA amplicons generated by the polymerase chain reaction (PCR) or other in vitro amplification techniques. Further, real time monitoring of PCR using MNAzymes allows the amount of target initially present in the reaction to be quantified.

Figure 14:
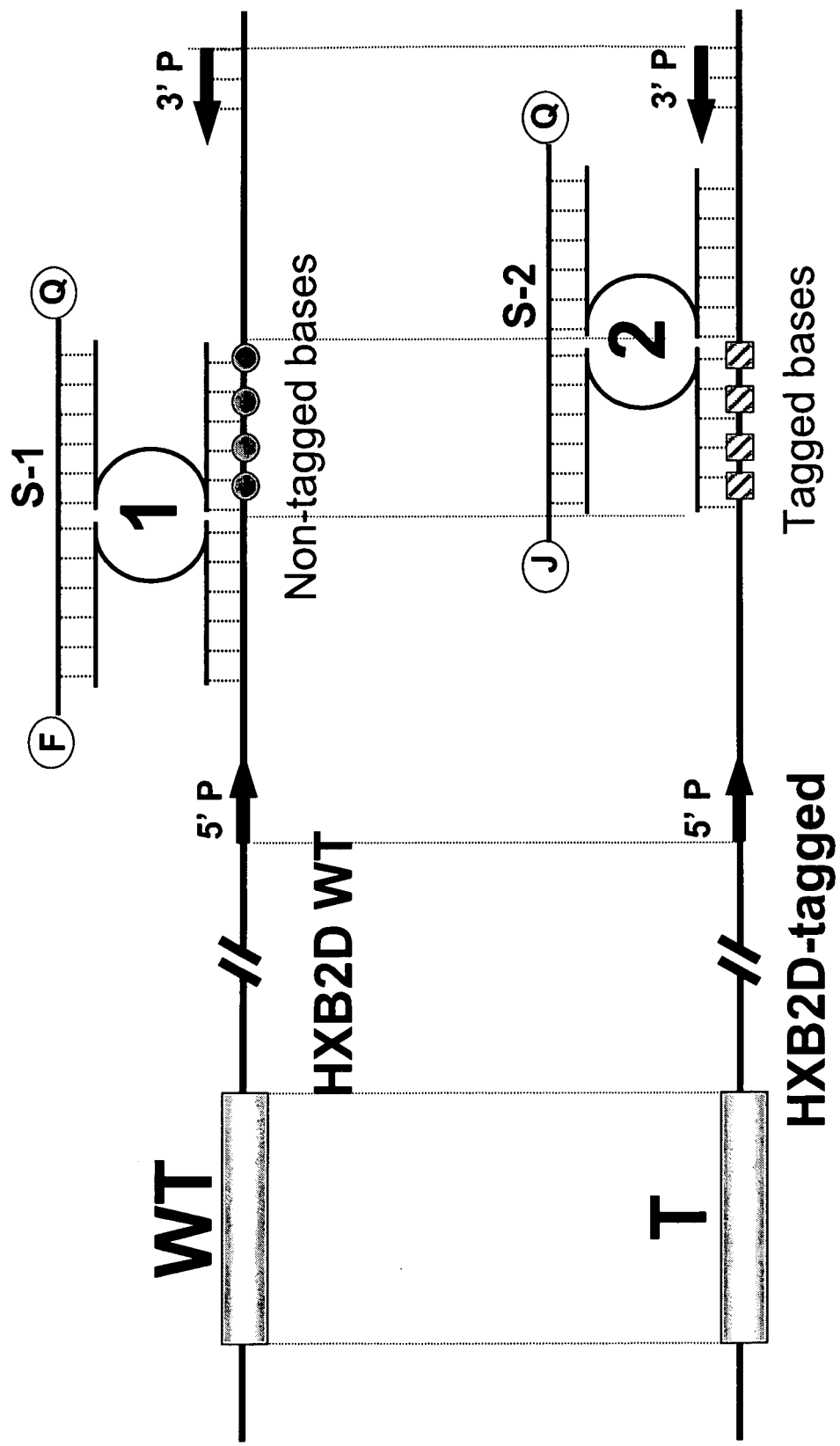
FIG. 14 represents an example of an MNAzyme PCR assay for monitoring HIV Viral Fitness. A duplex PCR assay is illustrated which used two MNAzymes for detection and quantification of two sequences simultaneously. The upper sequence, HIV HXB2D WT, contains wild type (WT) sequence located 5' of a second region which is recognised by MNAzyme 1. The grey circles in the second (3') region correspond to non-tagged wild type bases. The lower sequence, HIV HXB2D-tagged, contains sequences derived by amplification of the HIV target virus of interest (T), which are located 5' of a second region which is recognised by MNAzyme 2. The striped squares in the second (3') region correspond to silent mutations (tagged bases). The forward PCR primer (arrow 5'P) and reverse PCR primer (arrow 3'P) recognise both the upper HXB2D WT and the lower HXB2D-tagged sequences. MNAzyme 1 assembles in the presence of the upper HXB2D WT amplicons creating an active nucleic acid enzyme which cleaves substrate 1 (S-1) between FAM (F) and a quencher (Q). MNAzyme 2 assembles in the presence of the lower HXB2D-tagged sequence creating an active nucleic acid enzyme which cleaves substrate 2 (S-2) between JOE (J) and a quencher (Q).

A duplex PCR assay, which used two MNAzymes to facilitate real time monitoring, was developed for the simultaneous detection and quantification of (i) non-tagged HIV HXB2D WT sequences and (ii) tagged HIV HXB2D sequences that were modified to contain four silent mutations (the tag). The tag bases were designed such that they did not affect replication efficiency but did allow discrimination between the tagged HXB2D sequences and the non-tagged HXB2D WT sequence (FIG. 14). The absence or presence of the tag provided a surrogate marker for the presence of "wild type" sequence (WT) or those derived by amplification of the HIV target virus of interest (T) respectively which were located upstream of the region which was either non-tagged or tagged.

2.1. Partzyme Oligonucleotides for a Duplex PCR Assay

Multiple targets can be simultaneously detected in one multiplexed reaction that comprises multiple unique MNAzymes. Each MNAzyme has sensor arms specific for one target and substrate arms specific for a unique member of a series of generic reporter substrates, each one of which is labeled with a different fluorophore. In the following example, MNAzymes were designed to detect two different target amplicons, namely those amplified from the non-tagged HXB2D WT, and those amplified from the HXB2D-tagged sequences.

The sequences of the partzymes A and B for each target are listed below from 5' to 3'. In the following sequences the bases underlined form part of the catalytic core of the assembled MNAzyme, bases in bold hybridize with the target and bases in italics hybridize to the substrate. The P at the end of each sequences represents a 3' phosphate group.

TABLE 9

| SEQ ID NO: | Partzyme sequences listed in 5' to 3' direction | name |
|---|---|---|
| 13 | ATATCTCCTCCTCCAGGT<u>ACAACG</u> <u>AGAGGCGTGAT</u>-P | Partzyme A HXB2D (wild type) WTA4/6-P |
| 14 | *CTGGGAGGAA*<u>GGCTAGCT</u>CTGAAGA TCTCGGACTCATT-P | Partzyme B HXB2D (wild type) WTB5/6-P |

TABLE 9-continued

| SEQ ID NO: | Partzyme sequences listed in 5' to 3' direction | name |
|---|---|---|
| 15 | CTTCTCCAATTGTCCCTCATACAA CGAGAGGAAACCTT-P | Partzyme A HXB2D (tagged) TgA4/2-P |
| 16 | *TGCCCAGGGAGGCTAGCT*GTCACCTCCTCCGGG-P | Partzyme B HXB2D (tagged) TgB5/2-P |

2.2. Reporter Substrates

In this example, two different reporter substrates, each labeled with a different fluorophore, were used. The sequences of the substrates are written 5' to 3' below. In the current example, a first substrate SubBi-6 was end-labeled with a 6-FAM moiety at the 5' end and a BHQ moiety at the 3' end and was designated SubBi-6-FB. The substrate SubBi-6-FB was used to follow the accumulation of non-tagged HXB2D WT amplicons and cleavage of SubBi-6-FB was monitored at 516 nm with excitation at 492 nm. A second substrate SubBi-2 was end-labeled with a 6-JOE moiety at the 5' end and a BHQ1 moiety at the 3' end and was designated SubBi-2-JB. The substrate SubBi-2-JB was used to follow the accumulation of HXB2D-tagged amplicons and cleavage of SubBi-2-JB was monitored at 555 nm with excitation at 535 nm. The lower case bases represent RNA and the upper case bases represent DNA.

TABLE 10

| SEQ ID NO: | Substrate sequences listed in 5' to 3' direction | name |
|---|---|---|
| 17 | ATCACGCCTCguTCCTCCCAG | SubBi-6-FB |
| 18 | AAGGTTTCCTCguCCCTGGGCA | SubBi-2-JB |

2.3. PCR Primers for Amplification of the Target Sequences

The primers 5HIV and 3HIV were used for the amplification of both the wild type and tagged target HXB2D sequences. The amplicons were generated by PCR using the oligonucleotide PCR primers listed below.

TABLE 11

| SEQ ID NO: | Primer sequence listed in 5' to 3' direction | name |
|---|---|---|
| 19 (forward) | ATTAACAAGAGATGGTGGTAA | 5HIV |
| 20 (reverse) | GTGCTACTCCTAATGGTTCAA | 3HIV |

2.4. Reaction Components: Amplification and Quantification of Target Sequences

Real time amplification and quantification of the target sequences was performed in a total reaction volume of 25 µL. All reactions were conducted on an Mx3005P™ QPCR System (Stratagene). The cycling parameters were, 95° C. for 7 minutes, 10 cycles of 95° C. for 15 seconds and 60° C. for 30 seconds (with a 1° C. decrease in temperature per cycle), and finally 40 cycles of 95° C. for 15 seconds and 50° C. for 120 seconds. The reactions contained 40 nM of 3HIV and 400 nM of 5HIV, 200 nM of each partzyme (WTA4/6-P, WTB5/6-P, TgA4/2-P and TgB5/2-P), 200 nM of each substrate (SubBi-6-FB and SubBi-2-JB), 7 mM MgCl$_2$, 200 µM of each dNTP, 10 units RNASIN® (Promega), 1×IMMOBUFFER™ (Bioline), and 1 unit of IMMOLASE®(Bioline). Duplicate reactions either contained, or lacked, plasmid or genomic DNA template as indicated in the following Table 12.

TABLE 12

Target DNA sequence present in reactions.

| Type of DNA Template present in reactions | Template in reaction |
|---|---|
| Non-tagged HXB2D-WT plasmid and HXB2D-tagged plasmid present at a ratio of 1:1 diluted in a background of 5 ng of control human K562 genomic DNA. | 1E+06 copies (Standard 1) 2E+05 copies (Standard 2) 4E+04 copies (Standard 3) 8E+03 copies (Standard 4) 1.6E+03 copies (Standard 5) |
| Human genomic MT-4 DNA containing proviral sequences from wild type HXB2D WT and/or HXB2D-tagged (estimated percentages in spiked mixtures). | 100% wild type HXB2D WT 80% wild type HXB2D WT with 20% tagged HXB2D 50% wild type HXB2D WT with 50% tagged HXB2D 20% wild type HXB2D WT with 80% tagged HXB2 100% tagged HXB2D |
| No target control lacking genomic MT-4 DNA (dH$_2$O only) | |

2.5. Results: Simultaneous Amplification of the Non-Tagged and Tagged Target Sequences and Detection Via Cleavage of Two Different Reporter Substrates Using Target Specific MNAzymes.

Non-tagged HXB2D WT sequences were detected and quantified in real time by monitoring the increase in fluorescence in the FAM channel due to cleavage of SubBi-6-FB by MNAzyme 1 (comprising partzymes WTA4/6-P and WTB5/6-P). The MNAzyme 1 was only formed in the presence of the appropriate assembly facilitator, namely amplicons resulting from amplification of either HXB2D WT plasmid or proviral HXB2D WT target sequences (Tables 13 and 14 below). There was no increase in fluorescent signal in the FAM channel over time in the absence of HXB2D WT plasmid or proviral DNA. Further, there was no increase in fluorescent signal in the FAM channel over time in the presence of amplicons derived from tagged proviral DNA alone.

Tagged HXB2D sequences were detected and quantified in real time by monitoring the increase in fluorescence in the JOE channel due to cleavage of SubBi-2-JB by MNAzyme 2 (comprising partzymes TgA4/2-P and TgB5/2-P). The MNAzyme 2 was only formed in the presence of the appropriate assembly facilitator, namely amplicons resulting from amplification of either tagged HXB2D plasmid or tagged proviral HXB2D target sequences (Tables 13 and 14 below). There was no increase in fluorescent signal in the JOE channel over time in the absence of tagged plasmid or proviral HXB2D template DNA. Further, there was no increase in fluorescent signal in the JOE channel over time in the presence of amplicons derived from non-tagged HXB2D WT proviral DNA alone.

Standard curves were generated for the non-tagged and tagged HXB2D plasmid targets by plotting the log of the plasmid concentrations against the cycle number (Ct) at which threshold fluorescence was reached. The Ct values for each of the known amount (standards) as shown in Table 13 below are an average of duplicate reactions. The correlation coefficient ($R^2$) and slope of the standard curves, as well as the reaction efficiencies, are shown for both the non-tagged and tagged target sequences.

TABLE 13

Analysis of reactions containing non-tagged
wild type and tagged HXB2D plasmids

| | Threshold Cycle (Ct) | |
|---|---|---|
| | Non-tagged (WT) template (MNAzyme 1/FAM) | Tagged template (MNAzyme 2/JOE) |
| Standard 1 | 14.2 | 12.3 |
| Standard 2 | 16.9 | 15.1 |
| Standard 3 | 20.0 | 18.0 |
| Standard 4 | 22.9 | 20.7 |
| Standard 5 | 25.6 | 23.3 |
| No plasmid (dH₂O only) | No Ct | No Ct |
| Standard Curve | $R^2 = 0.999$ Slope = −4.135 Efficiency = 75% | $R^2 = 1.000$ Slope = −3.951 Efficiency = 79% |

The copy numbers of the non-tagged WT and the tagged HXB2D provirus within the MT-4 genomic DNA mixtures were estimated from the standard curve generated from the non-tagged and the tagged HXB2D plasmids (Table 14). The copy number of each of the non-tagged and the tagged HXB2D proviral sequences was expressed as a percentage of the total copy number (the non-tagged plus the tagged proviral sequences), and the estimates were compared to the percentage in original spiked MT-4 mixtures.

Samples with genomic MT-4 containing 100% non-tagged or 100% tagged proviral sequences were easily distinguished from each other (Table 14). No background increase in fluorescence over time was generated by MNAzyme 1 in the presence of tagged proviral sequence only. Similarly, no background increase in fluorescence over time was generated by MNAzyme 2 in the presence of non-tagged proviral sequence only (Table 14). Mixtures with ratios of non-tagged to tagged sequences of 80%, 50% and 20% of non-tagged were calculated to contain 77%, 47% and 21% of non-tagged respectively using the MNAzyme assay.

TABLE 14

Results of reactions for the amplification and detection of non-tagged
and tagged proviral DNA sequences present in varying percentages

| Percentage of proviral HXB2D sequence (in spiked sample) | | Quantity average of duplicates (Number of Copies) | | | Calculated percent present in spiked sample | |
|---|---|---|---|---|---|---|
| Non-tagged | Tagged | Non-tagged | Tagged | Total | Non-tagged | Tagged |
| 100% | 0% | 1.02E+05 | 0 | 1.02E+05 | 100% | 0% |
| 80% | 20% | 7.88E+04 | 2.35E+04 | 1.02E+05 | 77% | 23% |
| 50% | 50% | 4.96E+04 | 5.55E+04 | 1.05E+05 | 47% | 53% |
| 20% | 80% | 2.55E+04 | 9.48E+04 | 1.20E+05 | 21% | 79% |
| 0% | 100% | 0 | 1.16E+05 | 1.16E+05 | 0% | 100% |

The MNAzyme PCR reaction in this example allowed simultaneous detection and generation of standard curves for the quantification of non-tagged and tagged nucleic acid HXB2D sequences in a duplex reaction. The assay allowed discrimination between the non-tagged and the tagged sequences and vice versa. Further, the MNAzyme assay was able to determine the absolute and relative amounts of non-tagged and tagged proviral HXB2D DNA present in a sample. Thus the MNAzyme PCR provides a method for real time monitoring of the HIV-1 sequences in the HIV viral fitness assay.

Example 3

Use of MNAzymes for the Quantification of HIV and Control Nucleic Acid Sequences Via Triplex Real Time PCR A triplex PCR assay, which used three MNAzymes to facilitate real time monitoring, was developed for the simultaneous detection and quantification of (i) non-tagged HIV HXB2D WT sequences, (ii) tagged HIV HXB2D sequences that were modified to contain four silent mutations (the tag) and (iii) the control human RPLPO gene. The tag bases were designed such that they did not affect replication efficiency but did allow discrimination between the modified tagged HXB2D sequences and the non-tagged HXB2D WT sequence. The absence or presence of the tag provides a surrogate marker for the presence of "wild type" WT sequences or those derived by amplification of the HIV target virus of interest (T) respectively which are located upstream of the region which is either non-tagged or tagged.

3.1. Partzyme Oligonucleotides for a Triplex PCR Assay

Multiple targets can be simultaneously detected in one multiplexed reaction that comprises multiple unique MNAzymes. Each MNAzyme has sensor arms specific for one target and substrate arms specific for a unique member of a series of generic reporter substrates, each one of which is labeled with a different fluorophore. In the following example, MNAzymes were designed to detect three different target amplicons, namely those amplified from the non-tagged HXB2 WT, those amplified from the tagged HXB2D sequences and those amplified from the RPLPO gene.

The sequences of the partzymes A and B for each target are listed below from 5' to 3'. In the following sequences the bases underlined form part of the catalytic core of the assembled MNAzyme, bases in bold hybridize with the target and bases in italics hybridize to the substrate. The P at the end of the sequence indicates a 3' phosphate group.

TABLE 15

| SEQ ID NO: | Partzyme sequence listed in 5' to 3' direction | name |
|---|---|---|
| 13 | ATATCTCCTCCTCCAGGT<u>ACAACG</u> <u>A</u>*GAGGCGTGAT*-P | Partzyme A HXB2D (wild type) WTA4/6-P |
| 14 | *CTGGGAGGAA*<u>GGCTAGCT</u>CTGAAGA TCTCGGACTCATT-P | Partzyme B HXB2D (wild type) WTB5/6-P |

TABLE 15-continued

| SEQ ID NO: | Partzyme sequence listed in 5' to 3' direction | name |
|---|---|---|
| 15 | CTTCTCCAATTGTCCCTCATACAACGAGAGGAAACCTT-P | Partzyme A HXB2D (tagged) TgA4/2-P |
| 16 | *TGCCCAGGGA*GGCTAGCTGTCACCTCCTCCGGG-P | Partzyme B HXB2D (tagged) TgB5/2-P |
| 21 | CAAACGAGTCCTGGCCTTGTCTACAACGAGGTTGTGCTG-P | Partzyme A RPLPO RO5A4/3-P |
| 22 | *CGGTTGGT*GAGGCTAGCTGTGGAGAPartzymeCGGATTACACCTTC-P | Partzyme B RPLPO RO5B5/3-P |

3.2. Reporter Substrates

In this example, three different reporter substrates, each labeled with a different fluorophore, were used. The sequences of the substrates are written 5' to 3' below. In the current example, a first substrate SubBi-6 was end-labeled with a 6-FAM moiety at the 5' end and a BHQ moiety at the 3' end and was designated SubBi-6-FB. The substrate SubBi-6-FB was used to follow the accumulation of non-tagged wild type HXB2D WT amplicons and cleavage of SubBi-6-FB was monitored at 516 nm with excitation at 492 nm. A second substrate SubBi-2 was end-labeled with a 6-JOE moiety at the 5' end and a BHQ1 moiety at the 3' end and was designated SubBi-2-JB. The substrate SubBi-2-JB was used to follow the accumulation of tagged HXB2D amplicons and cleavage of SubBi-2-JB was monitored at 555 nm with excitation at 535 nm. The third substrate SubBi-3 was end-labeled with a Quasar 670 moiety at the 5' end and a BHQ2 moiety at the 3' end and was designated SubBi-3-Q6B2. The substrate SubBi-3-Q6B2 was used to monitor the accumulation of RPLPO amplicons and cleavage of SubBi-3-Q6B2 was monitored at 665 nm with excitation at 635 nm.

The sequences of the three substrates are listed below. The lower case bases represent RNA and the upper case bases represent DNA.

TABLE 16

| SEQ ID NO: | Substrate sequence listed in 5' to 3' direction | Name |
|---|---|---|
| 17 | ATCACGCCTCguTCCTCCCAG | SubBi-6-FB |
| 18 | AAGGTTTCCTCguCCCTGGGCA | SubBi-2-JB |
| 23 | CAGCACAACCguCACCAACCG | SubBi-3-Q6B2 |

3.3. PCR Primers for Amplification of the Target Sequences

The primers 5HIV and 3HIV were used for the amplification of both the wild type and tagged target HXB2D sequences. The primers 5RO5 and 3 RO5 were used to amplify the human genomic RPLPO gene. The sequences of the oligonucleotide PCR primers are listed below.

TABLE 17

| SEQ ID NO: | Primer sequence listed in 5' to 3' direction | name |
|---|---|---|
| 19 (forward) | ATTAACAAGAGATGGTGGTAA | 5HIV |
| 20 (reverse) | GTGCTACTCCTAATGGTTCAA | 3HIV |
| 24 (forward) | CATTCTATCATCAACGGGTA | 5RO5 |
| 25 (reverse) | CAAAGGCAGATGGATCAG | 3RO5 |

3.4. Reaction Components: Amplification and Quantification of Target Sequences Real time amplification and quantification of the target sequences was performed in a total reaction volume of 25 µL. All reactions were conducted on an Mx3005P™ QPCR System (Stratagene). The cycling parameters were, 95° C. for 7 minutes, 10 cycles of 95° C. for 15 seconds and 60° C. for 30 seconds (with a 1° C. decrease in temperature per cycle), and finally 40 cycles of 95° C. for 15 seconds and 50° C. for 120 seconds. The reactions contained 400 nM of 5HIV, 40 nM of 3HIV, 40 nM of 5RO5, 200 nM of 5RO5, 200 nM of each partzyme (WTA4/6-P, WTB5/6-P, TgA4/2-P, TgB5/2-P, RO5A4/3-P and RO5B5/3-P), 200 nM of each substrate (SubBi-6-FB, SubBi-2-JB and SubBi-3-Q6B2), 7 mM $MgCl_2$, 200 µM of each dNTP, 10 units RNASIN® (Promega), 1×IMMOBUFFER™ (Bioline), and 1 unit of IMMOLASE® (Bioline). Duplicate reactions either contained, or lacked, plasmid or genomic DNA template as indicated in the following Table 18.

TABLE 18

Target DNA sequence present in reactions.

| Type of DNA Template present in reactions | Template in reaction |
|---|---|
| Non-tagged HXB2D WT plasmid and tagged HXB2D plasmid present at a ratio of 1:1 diluted in a background of 5 ng of control human K562 genomic DNA. | 1E+06 copies (Standard 1) 2E+05 copies (Standard 2) 4E+04 copies (Standard 3) 8E+03 copies (Standard 4) 1.6E+03 copies (Standard 5) |
| Human genomic MT-4 DNA containing proviral sequences from non-tagged wild type HXB2D WT and/or tagged HXB2D (estimated percentages in spiked mixtures). | 100% non-tagged wild type HXB2D-WT 80% non-tagged wild type HXB2D-WT with 20% tagged HXB2D 50% non-tagged wild type HXB2D-WT with 50% tagged HXB2D 20% non-tagged wild type HXB2D-WT with 80% tagged HXB2D 100% tagged HXB2D No target control lacking genomic MT-4 DNA ($dH_2O$ only) |

3.5. Results: Simultaneous Amplification of the Non-Tagged Wild Type and Tagged Target HXB2D Sequences and Control RPLPO Gene Sequences with Detection Via Cleavage of Three Different Reporter Substrates Using Target Specific MNAzymes.

Non-tagged HXB2D-WT sequences were detected and quantified in real time by monitoring the increase in fluorescence in the FAM channel due to cleavage of SubBi-6-FB by MNAzyme 1 (comprising partzymes WTA4/6-P and WTB5/6-P). The MNAzyme 1 was only formed in the presence of the appropriate assembly facilitator, namely amplicons resulting from amplification of either non-tagged HXB2D WT plasmid or non-tagged proviral HXB2D WT target sequences (Tables 19 and 20 below). There was no increase in fluorescent signal in the FAM channel over time in the absence of non-tagged HXB2D WT plasmid or proviral DNA. Further, there was no increase in fluorescent signal in the FAM channel over time in the presence of amplicons derived from tagged proviral DNA alone.

Tagged HXB2D sequences were detected and quantified in real time by monitoring the increase in fluorescence in the JOE channel due to cleavage of SubBi-2-JB by MNAzyme 2 (comprising partzymes TgA4/2-P and TgB5/2-P). The MNAzyme 2 was only formed in the presence of the appropriate assembly facilitator, namely amplicons resulting from amplification of either tagged HXB2D plasmid or tagged proviral HXB2D target sequences (Tables 19 and 20 below). There was no increase in fluorescent signal in the JOE channel over time in the absence of tagged plasmid or proviral HXB2D template DNA. Further, there was no increase in fluorescent signal in the JOE channel over time in the presence of amplicons derived from non-tagged HXB2D WT proviral DNA alone.

The RPLPO gene was detected and quantified in real time by monitoring the increase in fluorescence in the Quasar channel due to cleavage of SubBi-3-Q6B2 by MNAzyme 3 (comprising partzymes RO5A4/3-P and RO5B5/3-P). The MNAzyme 3 was only formed in the presence of genomic DNA. An increase in fluorescence was observed in the presence of genomic DNA extracted from either K562 or MT-4 cells. There was no increase in fluorescent signal over time in the absence of genomic DNA.

Standard curves were generated for the non-tagged and tagged HXB2D plasmid targets by plotting the log of the plasmid concentrations against the cycle number (Ct) at which threshold fluorescence was reached. The Ct values for each of the known amount of the plasmids (standards) as shown in Table 19 below are an average of duplicate reactions. The Ct values for RPLPO are shown and similar values were obtained for all standards indicating a similar amount of genomic DNA was present in all standards. The correlation coefficient ($R^2$) and slope of the standard curves, as well as the reaction efficiencies, are shown for both the non-tagged and tagged target sequences.

TABLE 19

Results of real time analysis of non-tagged and tagged HXB2D targets and control RPLPO sequences

|  | Threshold (Ct) | | |
| --- | --- | --- | --- |
|  | Non-tagged (FAM) | Tagged (JOE) | RPLPO (Quasar 670) |
| Standard 1 | 18.3 | 16.0 | 23.8 |
| Standard 2 | 21.0 | 19.1 | 24.0 |
| Standard 3 | 24.4 | 21.9 | 24.1 |
| Standard 4 | 27.3 | 24.7 | 24.4 |
| Standard 5 | 31.2 | 27.5 | 24.8 |
| No plasmid (water only) | No Ct | No Ct | No Ct |
| Standard Curve | $R^2 = 0.996$ Slope = −4.59 Efficiency = 65% | $R^2 = 1.000$ Slope = −4.08 Efficiency = 76% | N/A |

The copy numbers of the non-tagged and the tagged HXB2D provirus within the MT-4 genomic DNA mixtures were estimated from the standard curve generated from the non-tagged and the tagged HXB2D plasmids (Table 20). The copy number of each of the non-tagged and the tagged HXB2D proviral sequences was expressed as a percentage of the total copy number (the non-tagged plus the tagged proviral sequences), and the estimates were compared to the percentage in original spiked MT-4 mixtures.

Samples with genomic MT-4 containing 100% non-tagged or 100% tagged proviral sequences were easily distinguished from each other (Table 20). No background increase in fluorescence over time was generated by MNAzyme 1 in the presence of tagged proviral sequence only. Similarly, no background increase in fluorescence over time was generated by MNAzyme 2 in the presence of non-tagged proviral sequences only (Table 20). Mixtures with ratios of non-tagged to tagged sequences of 80%, 50% and 20% of non-tagged were calculated to contain 74%, 47% and 28% of non-tagged respectively using the MNAzyme assay.

TABLE 20

Results of reactions for the amplification and detection of non-tagged and tagged proviral DNA sequences present in varying percentages (in a triplex MNAzyme format)

| Percentage of proviral HXB2D sequence (in spiked sample) | | Quantity average of duplicates (Number of Copies) | | | Calculated percent present in spiked sample | |
| --- | --- | --- | --- | --- | --- | --- |
| Non-tagged | Tagged | Non-tagged | Tagged | Total | Non-tagged | Tagged |
| 100% | 0% | 854750 | 0 | 854750 | 100% | 0% |
| 80% | 20% | 703150 | 239500 | 942650 | 74% | 26% |
| 50% | 50% | 498850 | 557250 | 1056100 | 47% | 53% |
| 20% | 80% | 324550 | 835200 | 1159750 | 28% | 72% |
| 0% | 100% | 0 | 1058000 | 1058000 | 0% | 100% |

The MNAzyme PCR reaction in this example allowed simultaneous detection and generation of standard curves for the quantification of non-tagged and tagged nucleic acid HXB2D sequences in a triplex reaction. The assay allowed discrimination between the non-tagged and the tagged sequences and vice versa. Further, the MNAzyme assay was able to determine the absolute and relative amounts of non-tagged and tagged proviral HXB2D DNA present in a sample. The RPLPO gene sequence can provide an internal control for the amount of genomic DNA present in a standard or test sample. Thus the triplex MNAzyme PCR provides a method for real time monitoring of the HIV-1 sequences in the HIV viral fitness assay.

The invention claimed is:

1. An ex vivo or in vitro method for determining the replicative capacity of two HIVs in an environment, said method comprising the steps of:
   a) generating a recombinant infectious virus comprising a tagged HIV genome having a polynucleotide comprising:
      i) a polynucleotide sequence derived from a first HIV comprising all, or part of, one or more of the gag, pol or env gene(s); and
      ii) polynucleotide sequences encoding the tat, rev, nef, vif, vpr, and vpu genes;
   wherein said polynucleotide further comprises polynucleotide sequences encoding any part of the gag, pol or env gene(s) that is not encoded by the polynucleotide sequence derived from said first HIV, wherein the tagged HIV genome includes one or more silent mutations in one of the HIV genes not comprised by the polynucleotide sequence derived from the first HIV,
      wherein the polynucleotide in subparts i) and ii) are from different HIVs;
   b) generating a non-tagged recombinant infectious virus comprising a non-tagged HIV genome having a polynucleotide comprising:
      i) a polynucleotide sequence derived from a second HIV comprising all, or part of, one or more of the gag, pol or env gene(s); and
      ii) polynucleotide sequences encoding the tat, rev, nef, vif, vpr, and vpu genes;
   wherein said polynucleotide further comprises polynucleotide sequences encoding any part of the gag, pol or env gene(s) that is not encoded by the polynucleotide sequence derived from said second HIV,
      wherein the polynucleotide in subparts i) and ii) are from different HIVs;
   c) mixing the recombinant infectious viruses obtained in steps a) and b) in a cell culture in a given environment; and
   d) performing quantitative amplification to determine the proportion of the tagged recombinant infectious virus and of the non-tagged recombinant infectious virus within the overall viral population, by detecting the one or more silent mutations in the tagged recombinant infectious virus, and by detecting the lack of the one or more silent mutations in the non-tagged recombinant infectious virus.

2. The method according to claim 1 wherein the amplification is performed by polymerase chain reaction (PCR), strand displacement amplification (SDA), transcription-mediated amplification (TMA), nucleic acid sequence based amplification (NASBA), self-sustained sequence replication (3SR), transcription-based amplification (TAS), rolling circle amplification (RCA), loop-mediated isothermal amplification (LAMP) or ligase chain reaction (LCR).

3. The method according to claim 1 where the quantitative amplification is monitored using fluorogenic primers, probes cleavable by deoxyribonucleic acid enzymes (DNAzymes) or multi-component nucleic acid enzymes (MNAzymes), fluorogenic probes, molecular beacons, scorpions or any other fluorescent resonance energy transfer (FRET) probes.

4. The method according to claim 1 wherein the quantitative amplification is performed by polymerase chain reaction, employing primers in the vicinity of MNAzymes, and probes that are cleaved by the MNAzymes.

5. The method according to claim 1 wherein each of the tagged HIV genome and the non-tagged HIV genome comprises the backbone of a wild-type or a mutant strain.

6. The method according to claim 5 wherein each of the tagged HIV genome and the non-tagged HIV genome is obtained from a proviral HIV genome or a HIV genome incorporated into a plasmid.

7. The method according to claim 6 wherein the plasmid comprises the genome of the HXB2D wild-type strain.

8. The method according to claim 1 wherein the polynucleotide sequence derived from the first HIV comprises one of the sequences selected from gag-PR-RT-int, gag-PR-RT, gag-PR, gag, PR-RT-int, RT-int, int, PR-RT, PR, RT, or env, and portions thereof.

9. The method according to claim 1 wherein the environment comprises one or more drugs, one or more binding proteins, or a mixture thereof.

10. The method according to claim 1 wherein the tagged HIV genome is generated by introducing one or more silent mutations in the integrase encoding region of the pol gene and wherein said introduction of one or more silent mutations is performed with primers SEQ ID NOs: 1-2.

* * * * *

UNITED STATES PATENT AND TRADEMARK OFFICE
CERTIFICATE OF CORRECTION

PATENT NO.       : 8,673,551 B2                                                                 Page 1 of 1
APPLICATION NO. : 12/094708
DATED            : March 18, 2014
INVENTOR(S)      : Rimsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 917 days.

Signed and Sealed this

Twenty-ninth Day of September, 2015

Michelle K. Lee
*Director of the United States Patent and Trademark Office*